United States Patent
Milano et al.

(10) Patent No.: US 11,274,121 B2
(45) Date of Patent: Mar. 15, 2022

(54) METHODS FOR ANTIBODY DRUG CONJUGATION, PURIFICATION, AND FORMULATION

(71) Applicant: ImmunoGen, Inc., Waltham, MA (US)

(72) Inventors: Daniel F. Milano, Reading, MA (US); Michael R. Reardon, North Attleboro, MA (US); Richard A. Silva, Needham, MA (US); Benjamin M. Hutchins, Boxborough, MA (US); Robert W. Herbst, Braintree, MA (US)

(73) Assignee: ImmunoGen, Inc., Waltham, MA (US)

( * ) Notice: Subject to any disclaimer, the term of this patent is extended or adjusted under 35 U.S.C. 154(b) by 0 days.

(21) Appl. No.: 16/245,890

(22) Filed: Jan. 11, 2019

(65) Prior Publication Data

US 2019/0270769 A1     Sep. 5, 2019

Related U.S. Application Data

(60) Provisional application No. 62/617,021, filed on Jan. 12, 2018, provisional application No. 62/673,535, filed on May 18, 2018.

(51) Int. Cl.
| | |
|---|---|
| *C07K 1/34* | (2006.01) |
| *A61K 47/68* | (2017.01) |
| *A61K 31/5383* | (2006.01) |
| *A61K 31/5517* | (2006.01) |
| *C07K 1/16* | (2006.01) |
| *G01N 33/68* | (2006.01) |
| *C07K 16/00* | (2006.01) |
| *C07K 16/28* | (2006.01) |

(52) U.S. Cl.
CPC ............ *C07K 1/34* (2013.01); *A61K 31/5383* (2013.01); *A61K 31/5517* (2013.01); *A61K 47/6803* (2017.08); *A61K 47/6849* (2017.08); *C07K 1/16* (2013.01); *C07K 16/00* (2013.01); *G01N 33/6854* (2013.01); *C07K 16/2866* (2013.01)

(58) Field of Classification Search
CPC . C07K 1/34; C07K 16/00; C07K 1/16; C07K 16/2866; A61K 47/6803; A61K 47/6849; A61K 31/5383; A61K 31/5517; G01N 33/6854
See application file for complete search history.

(56) References Cited

U.S. PATENT DOCUMENTS

| | | | |
|---|---|---|---|
| 2013/0281678 A1* | 10/2013 | Dai ................... | C07K 16/2884 530/391.9 |
| 2015/0182635 A1 | 7/2015 | Dai et al. | |

FOREIGN PATENT DOCUMENTS

| | | |
|---|---|---|
| WO | WO 2007/024536 A2 | 3/2007 |
| WO | WO 2010/141566 A1 | 12/2010 |
| WO | WO 2011/106528 A1 | 9/2011 |
| WO | WO 2012/128868 A1 | 9/2012 |
| WO | WO 2012/135517 A2 | 10/2012 |
| WO | WO 2017/004026 A1 | 1/2017 |
| WO | WO 2012/156455 A1 | 11/2017 |
| WO | WO 2018/119196 A1 | 6/2018 |
| WO | WO 2018/129029 A1 | 7/2018 |
| WO | WO 2018/213430 A1 | 11/2018 |

OTHER PUBLICATIONS

Casey et al. (Journal of Membrane Science, 2011,384, 82-88) (Year: 2011).*
Dizon-Maspat et al. (Biotechnology and Bioengineering, vol. 109, No. 4, Apr. 2012) (Year: 2012).*
Ayturk, E., et al., "Understanding single-pass tangential flow filtration and the new Era of bioprocessing," Pall Life Sciences—Biopharm Applications R&D, 10 pages (2016).
Herbst; R.W. Ph.D., "Continuous Processes for Antibody-Drug Conjugate (ADC) Manufacturing," ISPE, Huntington Beach, Dec. 11, 2018.
Nambiar; A.M.K., "Countercurrent staged diafiltration for monoclonal antibody formulation," Department of Chemical Engineering, Pennsylvania State University, Schreyer Honors College, Spring 2017.
Tang; Y. et al.. "Real-time analysis on drug-antibody ratio of antibody-drag conjugates for synthesis, process optimization and quality control," Nature Scientific-Reports 7:7763, Nature Publishing Group, England (2017).
Provisional Application, U.S. Appl. No. 62/691,342, inventors Hicks; S. and Yoder; N.., filed on Jun. 28, 2018.
Sebeika et al., "Protein and Antibody Functionalization Using Continuous Flow Microreactor Technology." J Flow Chem. 5(3):151-4, Springer Nature, Switzerland (2015).
Mohanty et al., "Novel tangential-flow countercurrent cascade ultrafiltration configuration for continuous purification of humanized monoclonal antibody," Journal of Membrane Science 307(1):117-125, Elsevier, Netherlands (2008).
"Continuous Processes for Antibody-Drug Conjugage (ADC) Manufacturing," ImmunoGen, Biotalk USA May 24, 2018, 20 pages.
International Search Report and Written Opinion for International Application No. PCT/US19/13120, International Search Authority, United States, dated May 17, 2019, 21 pages.

* cited by examiner

*Primary Examiner* — Sudhakar Katakam
(74) *Attorney, Agent, or Firm* — Sterne, Kessler, Goldstein & Fox P.L.L.C.

(57) ABSTRACT

Methods of producing, purifying, and formulating antibody drug conjugates (ADCs) are provided herein. The methods use continuous conjugation processes, single-pass tangential flow filtration, countercurrent diafiltration, and/or in-line process automation technologies. The methods decrease process times and costs and improve product consistency.

39 Claims, 14 Drawing Sheets
Specification includes a Sequence Listing.

SEQUENCE LISTING

```
<160> NUMBER OF SEQ ID NOS: 56

<210> SEQ ID NO 1
<211> LENGTH: 5
<212> TYPE: PRT
<213> ORGANISM: Artificial Sequence
<220> FEATURE:
<223> OTHER INFORMATION: huMov19 VH CDR1

<400> SEQUENCE: 1

Gly Tyr Phe Met Asn
1               5

<210> SEQ ID NO 2
<211> LENGTH: 17
<212> TYPE: PRT
<213> ORGANISM: Artificial Sequence
<220> FEATURE:
<223> OTHER INFORMATION: huMov19 VH CDR2

<400> SEQUENCE: 2

Arg Ile His Pro Tyr Asp Gly Asp Thr Phe Tyr Asn Gln Lys Phe Gln
1               5                   10                  15

Gly

<210> SEQ ID NO 3
<211> LENGTH: 9
<212> TYPE: PRT
<213> ORGANISM: Artificial Sequence
<220> FEATURE:
<223> OTHER INFORMATION: huMov19 VH CDR3

<400> SEQUENCE: 3

Tyr Asp Gly Ser Arg Ala Met Asp Tyr
1               5

<210> SEQ ID NO 4
<211> LENGTH: 15
<212> TYPE: PRT
```

```
<213> ORGANISM: Artificial Sequence
<220> FEATURE:
<223> OTHER INFORMATION: huMov19 VL CDR1

<400> SEQUENCE: 4

Lys Ala Ser Gln Ser Val Ser Phe Ala Gly Thr Ser Leu Met His
1               5                   10                  15

<210> SEQ ID NO 5
<211> LENGTH: 7
<212> TYPE: PRT
<213> ORGANISM: Artificial Sequence
<220> FEATURE:
<223> OTHER INFORMATION: huMov19 VL CDR2

<400> SEQUENCE: 5

Arg Ala Ser Asn Leu Glu Ala
1               5

<210> SEQ ID NO 6
<211> LENGTH: 9
<212> TYPE: PRT
<213> ORGANISM: Artificial Sequence
<220> FEATURE:
<223> OTHER INFORMATION: huMov19 VL CDR3

<400> SEQUENCE: 6

Gln Gln Ser Arg Glu Tyr Pro Tyr Thr
1               5

<210> SEQ ID NO 7
<211> LENGTH: 5
<212> TYPE: PRT
<213> ORGANISM: Artificial Sequence
<220> FEATURE:
<223> OTHER INFORMATION: Z4681A VH CDR1

<400> SEQUENCE: 7

Ser Tyr Tyr Ile His
1               5

<210> SEQ ID NO 8
<211> LENGTH: 17
<212> TYPE: PRT
<213> ORGANISM: Artificial Sequence
<220> FEATURE:
<223> OTHER INFORMATION: Z4681A VH CDR2

<400> SEQUENCE: 8

Val Ile Tyr Pro Gly Asn Asp Asp Ile Ser Tyr Asn Gln Lys Phe Gln
1               5                   10                  15

Gly

<210> SEQ ID NO 9
<211> LENGTH: 9
<212> TYPE: PRT
<213> ORGANISM: Artificial Sequence
<220> FEATURE:
<223> OTHER INFORMATION: Z4681A VH CDR3

<400> SEQUENCE: 9

Glu Val Arg Leu Arg Tyr Phe Asp Val
1               5

<210> SEQ ID NO 10
<211> LENGTH: 17
```

```
<212> TYPE: PRT
<213> ORGANISM: Artificial Sequence
<220> FEATURE:
<223> OTHER INFORMATION: Z4681A VL CDR1

<400> SEQUENCE: 10

Lys Ser Ser Gln Ser Val Phe Phe Ser Ser Gln Lys Asn Tyr Leu
1               5                   10                  15

Ala

<210> SEQ ID NO 11
<211> LENGTH: 7
<212> TYPE: PRT
<213> ORGANISM: Artificial Sequence
<220> FEATURE:
<223> OTHER INFORMATION: Z4681A VL CDR2

<400> SEQUENCE: 11

Trp Ala Ser Thr Arg Glu Ser
1               5

<210> SEQ ID NO 12
<211> LENGTH: 8
<212> TYPE: PRT
<213> ORGANISM: Artificial Sequence
<220> FEATURE:
<223> OTHER INFORMATION: Z4681A VL CDR3

<400> SEQUENCE: 12

His Gln Tyr Leu Ser Ser Arg Thr
1               5

<210> SEQ ID NO 13
<211> LENGTH: 5
<212> TYPE: PRT
<213> ORGANISM: Artificial Sequence
<220> FEATURE:
<223> OTHER INFORMATION: G4723A VH CDR1

<400> SEQUENCE: 13

Ser Ser Ile Met His
1               5

<210> SEQ ID NO 14
<211> LENGTH: 17
<212> TYPE: PRT
<213> ORGANISM: Artificial Sequence
<220> FEATURE:
<223> OTHER INFORMATION: G4723A VH CDR2

<400> SEQUENCE: 14

Tyr Ile Lys Pro Tyr Asn Asp Gly Thr Lys Tyr Asn Glu Lys Phe Lys
1               5                   10                  15

Gly

<210> SEQ ID NO 15
<211> LENGTH: 12
<212> TYPE: PRT
<213> ORGANISM: Artificial Sequence
<220> FEATURE:
<223> OTHER INFORMATION: G4723A VH CDR3

<400> SEQUENCE: 15

Glu Gly Gly Asn Asp Tyr Tyr Asp Thr Met Asp Tyr
1               5                   10
```

<210> SEQ ID NO 16
<211> LENGTH: 11
<212> TYPE: PRT
<213> ORGANISM: Artificial Sequence
<220> FEATURE:
<223> OTHER INFORMATION: G4723A VL CDR1

<400> SEQUENCE: 16

Arg Ala Ser Gln Asp Ile Asn Ser Tyr Leu Ser
1               5                   10

<210> SEQ ID NO 17
<211> LENGTH: 7
<212> TYPE: PRT
<213> ORGANISM: Artificial Sequence
<220> FEATURE:
<223> OTHER INFORMATION: G4723A VL CDR2

<400> SEQUENCE: 17

Arg Val Asn Arg Leu Val Asp
1               5

<210> SEQ ID NO 18
<211> LENGTH: 9
<212> TYPE: PRT
<213> ORGANISM: Artificial Sequence
<220> FEATURE:
<223> OTHER INFORMATION: G4723A VL CDR3

<400> SEQUENCE: 18

Leu Gln Tyr Asp Ala Phe Pro Tyr Thr
1               5

<210> SEQ ID NO 19
<211> LENGTH: 5
<212> TYPE: PRT
<213> ORGANISM: Artificial Sequence
<220> FEATURE:
<223> OTHER INFORMATION: huCMET-27 VH CDR1

<400> SEQUENCE: 19

Ser Tyr Asp Met Ser
1               5

<210> SEQ ID NO 20
<211> LENGTH: 17
<212> TYPE: PRT
<213> ORGANISM: Artificial Sequence
<220> FEATURE:
<223> OTHER INFORMATION: huCMET-27 VH CDR2

<400> SEQUENCE: 20

Thr Ile Asn Ser Asn Gly Val Ser Ile Tyr Tyr Pro Asp Ser Val Lys
1               5                   10                  15

Gly

<210> SEQ ID NO 21
<211> LENGTH: 9
<212> TYPE: PRT
<213> ORGANISM: Artificial Sequence
<220> FEATURE:
<223> OTHER INFORMATION: huCMET-27 VH CDR3

<400> SEQUENCE: 21

Glu Glu Ile Thr Thr Glu Met Asp Tyr
1               5

```
<210> SEQ ID NO 22
<211> LENGTH: 15
<212> TYPE: PRT
<213> ORGANISM: Artificial Sequence
<220> FEATURE:
<223> OTHER INFORMATION: huCMET-27 VL CDR1

<400> SEQUENCE: 22

Arg Ala Ser Glu Ser Val Asp Ser Tyr Gly Asn Ser Phe Ile His
1               5                   10                  15

<210> SEQ ID NO 23
<211> LENGTH: 7
<212> TYPE: PRT
<213> ORGANISM: Artificial Sequence
<220> FEATURE:
<223> OTHER INFORMATION: huCMET-27 VL CDR2

<400> SEQUENCE: 23

Arg Ala Ser Asn Leu Glu Ser
1               5

<210> SEQ ID NO 24
<211> LENGTH: 9
<212> TYPE: PRT
<213> ORGANISM: Artificial Sequence
<220> FEATURE:
<223> OTHER INFORMATION: huCMET-27 VL CDR3

<400> SEQUENCE: 24

Gln Gln Ser Asn Glu Glu Pro Leu Thr
1               5

<210> SEQ ID NO 25
<211> LENGTH: 5
<212> TYPE: PRT
<213> ORGANISM: Artificial Sequence
<220> FEATURE:
<223> OTHER INFORMATION: huB4 VH CDR1

<400> SEQUENCE: 25

Ser Asn Trp Met His
1               5

<210> SEQ ID NO 26
<211> LENGTH: 10
<212> TYPE: PRT
<213> ORGANISM: Artificial Sequence
<220> FEATURE:
<223> OTHER INFORMATION: huB4 VH CDR2

<400> SEQUENCE: 26

Glu Ile Asp Pro Ser Asp Ser Tyr Thr Asn
1               5                   10

<210> SEQ ID NO 27
<211> LENGTH: 11
<212> TYPE: PRT
<213> ORGANISM: Artificial Sequence
<220> FEATURE:
<223> OTHER INFORMATION: huB4 VH CDR3

<400> SEQUENCE: 27

Gly Ser Asn Pro Tyr Tyr Tyr Ala Met Asp Tyr
1               5                   10
```

<210> SEQ ID NO 28
<211> LENGTH: 10
<212> TYPE: PRT
<213> ORGANISM: Artificial Sequence
<220> FEATURE:
<223> OTHER INFORMATION: huB4 VL CDR1

<400> SEQUENCE: 28

```
Ser Ala Ser Ser Gly Val Asn Tyr Met His
1               5                   10
```

<210> SEQ ID NO 29
<211> LENGTH: 7
<212> TYPE: PRT
<213> ORGANISM: Artificial Sequence
<220> FEATURE:
<223> OTHER INFORMATION: huB4 VL CDR2

<400> SEQUENCE: 29

```
Asp Thr Ser Lys Leu Ala Ser
1               5
```

<210> SEQ ID NO 30
<211> LENGTH: 7
<212> TYPE: PRT
<213> ORGANISM: Artificial Sequence
<220> FEATURE:
<223> OTHER INFORMATION: huB4 VL CDR3

<400> SEQUENCE: 30

```
His Gln Arg Gly Ser Tyr Thr
1               5
```

<210> SEQ ID NO 31
<211> LENGTH: 5
<212> TYPE: PRT
<213> ORGANISM: Artificial Sequence
<220> FEATURE:
<223> OTHER INFORMATION: huADAM9 VH CDR1

<400> SEQUENCE: 31

```
Ser Tyr Trp Met His
1               5
```

<210> SEQ ID NO 32
<211> LENGTH: 17
<212> TYPE: PRT
<213> ORGANISM: Artificial Sequence
<220> FEATURE:
<223> OTHER INFORMATION: huADAM9 VH CDR2

<400> SEQUENCE: 32

```
Glu Ile Ile Pro Ile Phe Gly His Thr Asn Tyr Asn Glu Lys Phe Lys
1               5                   10                  15

Ser
```

<210> SEQ ID NO 33
<211> LENGTH: 14
<212> TYPE: PRT
<213> ORGANISM: Artificial Sequence
<220> FEATURE:
<223> OTHER INFORMATION: huADAM9 VH CDR3

<400> SEQUENCE: 33

```
Gly Gly Tyr Tyr Tyr Tyr Phe Asn Ser Gly Thr Leu Asp Tyr
1               5                   10
```

<210> SEQ ID NO 34
<211> LENGTH: 15
<212> TYPE: PRT
<213> ORGANISM: Artificial Sequence
<220> FEATURE:
<223> OTHER INFORMATION: huADAM9 VL CDR1

<400> SEQUENCE: 34

Lys Ala Ser Gln Ser Val Asp Tyr Ser Gly Asp Ser Tyr Met Asn
1               5                   10                  15

<210> SEQ ID NO 35
<211> LENGTH: 7
<212> TYPE: PRT
<213> ORGANISM: Artificial Sequence
<220> FEATURE:
<223> OTHER INFORMATION: huADAM9 VL CDR2

<400> SEQUENCE: 35

Ala Ala Ser Asp Leu Glu Ser
1               5

<210> SEQ ID NO 36
<211> LENGTH: 9
<212> TYPE: PRT
<213> ORGANISM: Artificial Sequence
<220> FEATURE:
<223> OTHER INFORMATION: huADAM9 VL CDR3

<400> SEQUENCE: 36

Gln Gln Ser His Glu Asp Pro Phe Thr
1               5

<210> SEQ ID NO 37
<211> LENGTH: 118
<212> TYPE: PRT
<213> ORGANISM: Artificial Sequence
<220> FEATURE:
<223> OTHER INFORMATION: huMov19 VH

<400> SEQUENCE: 37

Gln Val Gln Leu Val Gln Ser Gly Ala Glu Val Val Lys Pro Gly Ala
1               5                   10                  15

Ser Val Lys Ile Ser Cys Lys Ala Ser Gly Tyr Thr Phe Thr Gly Tyr
            20                  25                  30

Phe Met Asn Trp Val Lys Gln Ser Pro Gly Gln Ser Leu Glu Trp Ile
        35                  40                  45

Gly Arg Ile His Pro Tyr Asp Gly Asp Thr Phe Tyr Asn Gln Lys Phe
    50                  55                  60

Gln Gly Lys Ala Thr Leu Thr Val Asp Lys Ser Asn Thr Ala His
65                  70                  75                  80

Met Glu Leu Leu Ser Leu Thr Ser Glu Asp Phe Ala Val Tyr Tyr Cys
                85                  90                  95

Thr Arg Tyr Asp Gly Ser Arg Ala Met Asp Tyr Trp Gly Gln Gly Thr
            100                 105                 110

Thr Val Thr Val Ser Ser
        115

<210> SEQ ID NO 38
<211> LENGTH: 112
<212> TYPE: PRT
<213> ORGANISM: Artificial Sequence
<220> FEATURE:
<223> OTHER INFORMATION: huMov19 VL version 1.00

<400> SEQUENCE: 38

Asp Ile Val Leu Thr Gln Ser Pro Leu Ser Leu Ala Val Ser Leu Gly
1               5                   10                  15

Gln Pro Ala Ile Ile Ser Cys Lys Ala Ser Gln Ser Val Ser Phe Ala
            20                  25                  30

Gly Thr Ser Leu Met His Trp Tyr His Gln Lys Pro Gly Gln Gln Pro
        35                  40                  45

Arg Leu Leu Ile Tyr Arg Ala Ser Asn Leu Glu Ala Gly Val Pro Asp
    50                  55                  60

Arg Phe Ser Gly Ser Gly Ser Lys Thr Asp Phe Thr Leu Asn Ile Ser
65                  70                  75                  80

Pro Val Glu Ala Glu Asp Ala Ala Thr Tyr Tyr Cys Gln Gln Ser Arg
                85                  90                  95

Glu Tyr Pro Tyr Thr Phe Gly Gly Gly Thr Lys Leu Glu Ile Lys Arg
            100                 105                 110

<210> SEQ ID NO 39
<211> LENGTH: 112
<212> TYPE: PRT
<213> ORGANISM: Artificial Sequence
<220> FEATURE:
<223> OTHER INFORMATION: huMov19 VL version 1.60

<400> SEQUENCE: 39

Asp Ile Val Leu Thr Gln Ser Pro Leu Ser Leu Ala Val Ser Leu Gly
1               5                   10                  15

Gln Pro Ala Ile Ile Ser Cys Lys Ala Ser Gln Ser Val Ser Phe Ala
            20                  25                  30

Gly Thr Ser Leu Met His Trp Tyr His Gln Lys Pro Gly Gln Gln Pro
        35                  40                  45

Arg Leu Leu Ile Tyr Arg Ala Ser Asn Leu Glu Ala Gly Val Pro Asp
    50                  55                  60

Arg Phe Ser Gly Ser Gly Ser Lys Thr Asp Phe Thr Leu Thr Ile Ser
65                  70                  75                  80

Pro Val Glu Ala Glu Asp Ala Ala Thr Tyr Tyr Cys Gln Gln Ser Arg
                85                  90                  95

Glu Tyr Pro Tyr Thr Phe Gly Gly Gly Thr Lys Leu Glu Ile Lys Arg
            100                 105                 110

<210> SEQ ID NO 40
<211> LENGTH: 118
<212> TYPE: PRT
<213> ORGANISM: Artificial Sequence
<220> FEATURE:
<223> OTHER INFORMATION: Z4681A VH

<400> SEQUENCE: 40

Gln Val Gln Leu Gln Gln Pro Gly Ala Glu Val Val Lys Pro Gly Ala
1               5                   10                  15

Ser Val Lys Met Ser Cys Lys Ala Ser Gly Tyr Thr Phe Thr Ser Tyr
            20                  25                  30

Tyr Ile His Trp Ile Lys Gln Thr Pro Gly Gln Gly Leu Glu Trp Val
        35                  40                  45

Gly Val Ile Tyr Pro Gly Asn Asp Asp Ile Ser Tyr Asn Gln Lys Phe
    50                  55                  60

```
Gln Gly Lys Ala Thr Leu Thr Ala Asp Lys Ser Thr Thr Ala Tyr
 65                  70                  75                  80

Met Gln Leu Ser Ser Leu Thr Ser Glu Asp Ser Ala Val Tyr Tyr Cys
                 85                  90                  95

Ala Arg Glu Val Arg Leu Arg Tyr Phe Asp Val Trp Gly Gln Gly Thr
            100                 105                 110

Thr Val Thr Val Ser Ser
            115

<210> SEQ ID NO 41
<211> LENGTH: 113
<212> TYPE: PRT
<213> ORGANISM: Artificial Sequence
<220> FEATURE:
<223> OTHER INFORMATION: Z4681A VL

<400> SEQUENCE: 41

Glu Ile Val Leu Thr Gln Ser Pro Gly Ser Leu Ala Val Ser Pro Gly
  1               5                  10                  15

Glu Arg Val Thr Met Ser Cys Lys Ser Ser Gln Ser Val Phe Phe Ser
             20                  25                  30

Ser Ser Gln Lys Asn Tyr Leu Ala Trp Tyr Gln Gln Ile Pro Gly Gln
         35                  40                  45

Ser Pro Arg Leu Leu Ile Tyr Trp Ala Ser Thr Arg Glu Ser Gly Val
 50                  55                  60

Pro Asp Arg Phe Thr Gly Ser Gly Ser Gly Thr Asp Phe Thr Leu Thr
 65                  70                  75                  80

Ile Ser Ser Val Gln Pro Glu Asp Leu Ala Ile Tyr Tyr Cys His Gln
                 85                  90                  95

Tyr Leu Ser Ser Arg Thr Phe Gly Gln Gly Thr Lys Leu Glu Ile Lys
            100                 105                 110

Arg

<210> SEQ ID NO 42
<211> LENGTH: 121
<212> TYPE: PRT
<213> ORGANISM: Artificial Sequence
<220> FEATURE:
<223> OTHER INFORMATION: G4723A VH

<400> SEQUENCE: 42

Gln Val Gln Leu Val Gln Ser Gly Ala Glu Val Lys Lys Pro Gly Ala
  1               5                  10                  15

Ser Val Lys Val Ser Cys Lys Ala Ser Gly Tyr Ile Phe Thr Ser Ser
             20                  25                  30

Ile Met His Trp Val Arg Gln Ala Pro Gly Gln Gly Leu Glu Trp Ile
         35                  40                  45

Gly Tyr Ile Lys Pro Tyr Asn Asp Gly Thr Lys Tyr Asn Glu Lys Phe
 50                  55                  60

Lys Gly Arg Ala Thr Leu Thr Ser Asp Arg Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Glu Gly Gly Asn Asp Tyr Tyr Asp Thr Met Asp Tyr Trp Gly
            100                 105                 110

Gln Gly Thr Leu Val Thr Val Ser Ser
            115                 120
```

<210> SEQ ID NO 43
<211> LENGTH: 108
<212> TYPE: PRT
<213> ORGANISM: Artificial Sequence
<220> FEATURE:
<223> OTHER INFORMATION: G4723A VL

<400> SEQUENCE: 43

Asp Ile Gln Met Thr Gln Ser Pro Ser Leu Ser Ala Ser Val Gly
1               5                   10                  15

Asp Arg Val Thr Ile Thr Cys Arg Ala Ser Gln Asp Ile Asn Ser Tyr
            20                  25                  30

Leu Ser Trp Phe Gln Gln Lys Pro Gly Lys Ala Pro Lys Thr Leu Ile
        35                  40                  45

Tyr Arg Val Asn Arg Leu Val Asp Gly Val Pro Ser Arg Phe Ser Gly
    50                  55                  60

Ser Gly Ser Gly Asn Asp Tyr Thr Leu Thr Ile Ser Ser Leu Gln Pro
65                  70                  75                  80

Glu Asp Phe Ala Thr Tyr Tyr Cys Leu Gln Tyr Asp Ala Phe Pro Tyr
                85                  90                  95

Thr Phe Gly Gln Gly Thr Lys Val Glu Ile Lys Arg
            100                 105

<210> SEQ ID NO 44
<211> LENGTH: 118
<212> TYPE: PRT
<213> ORGANISM: Artificial Sequence
<220> FEATURE:
<223> OTHER INFORMATION: huCMET-27 VH

<400> SEQUENCE: 44

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Gly Leu Glu Trp Val
        35                  40                  45

Ala Thr Ile Asn Ser Asn Gly Val Ser Ile Tyr Tyr Pro Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Glu Ile Thr Thr Glu Met Asp Tyr Trp Gly Gln Gly Thr
            100                 105                 110

Leu Val Thr Val Ser Ser
        115

<210> SEQ ID NO 45
<211> LENGTH: 112
<212> TYPE: PRT
<213> ORGANISM: Artificial Sequence
<220> FEATURE:
<223> OTHER INFORMATION: huCMET-27 VL

<400> SEQUENCE: 45

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Glu Ser Val Asp Ser Tyr

```
                20                  25                  30
Gly Asn Ser Phe Ile His Trp Tyr Gln Gln Lys Pro Gly Gln Ala Pro
            35                  40                  45

Arg Leu Leu Ile Tyr Arg Ala Ser Asn Leu Glu Ser Gly Ile Pro Ala
 50                  55                  60

Arg Phe Ser Gly Ser Gly Ser Gly Thr Asp Phe Thr Leu Thr Ile Ser
 65                  70                  75                  80

Ser Leu Glu Pro Glu Asp Phe Ala Val Tyr Tyr Cys Gln Gln Ser Asn
                85                  90                  95

Glu Glu Pro Leu Thr Phe Gly Gln Gly Thr Lys Val Glu Leu Lys Arg
            100                 105                 110

<210> SEQ ID NO 46
<211> LENGTH: 120
<212> TYPE: PRT
<213> ORGANISM: Artificial Sequence
<220> FEATURE:
<223> OTHER INFORMATION: huB4 VH

<400> SEQUENCE: 46

Gln Val Gln Leu Val Gln Pro Gly Ala Glu Val Val Lys Pro Gly Ala
 1                   5                  10                  15

Ser Val Lys Leu Ser Cys Lys Thr Ser Gly Tyr Thr Phe Thr Ser Asn
                20                  25                  30

Trp Met His Trp Val Lys Gln Ala Pro Gly Gln Gly Leu Glu Trp Ile
            35                  40                  45

Gly Glu Ile Asp Pro Ser Asp Ser Tyr Thr Asn Tyr Asn Gln Asn Phe
 50                  55                  60

Gln Gly Lys Ala Lys Leu Thr Val Asp Lys Ser Thr Ser Thr Ala Tyr
 65                  70                  75                  80

Met Glu Val Ser Ser Leu Arg Ser Asp Asp Thr Ala Val Tyr Tyr Cys
                85                  90                  95

Ala Arg Gly Ser Asn Pro Tyr Tyr Ala Met Asp Tyr Trp Gly Gln
            100                 105                 110

Gly Thr Ser Val Thr Val Ser Ser
        115                 120

<210> SEQ ID NO 47
<211> LENGTH: 105
<212> TYPE: PRT
<213> ORGANISM: Artificial Sequence
<220> FEATURE:
<223> OTHER INFORMATION: huB4 VL

<400> SEQUENCE: 47

Glu Ile Val Leu Thr Gln Ser Pro Ala Ile Met Ser Ala Ser Pro Gly
 1                   5                  10                  15

Glu Arg Val Thr Met Thr Cys Ser Ala Ser Ser Gly Val Asn Tyr Met
                20                  25                  30

His Trp Tyr Gln Gln Lys Pro Gly Thr Ser Pro Arg Arg Trp Ile Tyr
            35                  40                  45

Asp Thr Ser Lys Leu Ala Ser Gly Val Pro Ala Arg Phe Ser Gly Ser
 50                  55                  60

Gly Ser Gly Thr Asp Tyr Ser Leu Thr Ile Ser Ser Met Glu Pro Glu
 65                  70                  75                  80

Asp Ala Ala Thr Tyr Tyr Cys His Gln Arg Gly Ser Tyr Thr Phe Gly
                85                  90                  95
```

```
Gly Gly Thr Lys Leu Glu Ile Lys Arg
            100                 105
```

<210> SEQ ID NO 48
<211> LENGTH: 123
<212> TYPE: PRT
<213> ORGANISM: Artificial Sequence
<220> FEATURE:
<223> OTHER INFORMATION: huADAM9 VH

<400> SEQUENCE: 48

```
Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Trp Met His Trp Val Arg Gln Ala Pro Gly Lys Gly Leu Glu Trp Val
        35                  40                  45

Gly Glu Ile Ile Pro Ile Phe Gly His Thr Asn Tyr Asn Glu Lys Phe
    50                  55                  60

Lys Ser Arg Phe Thr Ile Ser Leu Asp Asn Ser Lys Asn Thr Leu Tyr
65                  70                  75                  80

Leu Gln Met Gly Ser Leu Arg Ala Glu Asp Thr Ala Val Tyr Tyr Cys
                85                  90                  95

Ala Arg Gly Gly Tyr Tyr Tyr Tyr Phe Asn Ser Gly Thr Leu Asp Tyr
            100                 105                 110

Trp Gly Gln Gly Thr Thr Val Thr Val Ser Ser
        115                 120
```

<210> SEQ ID NO 49
<211> LENGTH: 111
<212> TYPE: PRT
<213> ORGANISM: Artificial Sequence
<220> FEATURE:
<223> OTHER INFORMATION: huADAM9 VL

<400> SEQUENCE: 49

```
Asp Ile Val Met Thr Gln Ser Pro Asp Ser Leu Ala Val Ser Leu Gly
1               5                   10                  15

Glu Arg Ala Thr Ile Ser Cys Lys Ala Ser Gln Ser Val Asp Tyr Ser
            20                  25                  30

Gly Asp Ser Tyr Met Asn Trp Tyr Gln Gln Lys Pro Gly Gln Pro Pro
        35                  40                  45

Lys Leu Leu Ile Tyr Ala Ala Ser Asp Leu Glu Ser Gly Ile Pro Ala
    50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Thr Tyr Tyr Cys Gln Gln Ser His
                85                  90                  95

Glu Asp Pro Phe Thr Phe Gly Gln Gly Thr Lys Leu Glu Ile Lys
            100                 105                 110
```

<210> SEQ ID NO 50
<211> LENGTH: 447
<212> TYPE: PRT
<213> ORGANISM: Artificial Sequence
<220> FEATURE:
<223> OTHER INFORMATION: huMov19 Heavy

<400> SEQUENCE: 50

```
Gln Val Gln Leu Val Gln Ser Gly Ala Glu Val Val Lys Pro Gly Ala
```

-continued

```
1               5                   10                  15
Ser Val Lys Ile Ser Cys Lys Ala Ser Gly Tyr Thr Phe Thr Gly Tyr
                20                  25                  30

Phe Met Asn Trp Val Lys Gln Ser Pro Gly Gln Ser Leu Glu Trp Ile
            35                  40                  45

Gly Arg Ile His Pro Tyr Asp Gly Asp Thr Phe Tyr Asn Gln Lys Phe
        50                  55                  60

Gln Gly Lys Ala Thr Leu Thr Val Asp Lys Ser Ser Asn Thr Ala His
65                  70                  75                  80

Met Glu Leu Leu Ser Leu Thr Ser Glu Asp Phe Ala Val Tyr Tyr Cys
                85                  90                  95

Thr Arg Tyr Asp Gly Ser Arg Ala Met Asp Tyr Trp Gly Gln Gly Thr
            100                 105                 110

Thr Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
        130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430
```

Leu His Asn His Tyr Thr Gln Lys Ser Leu Ser Leu Ser Pro Gly
            435                 440                 445

<210> SEQ ID NO 51
<211> LENGTH: 218
<212> TYPE: PRT
<213> ORGANISM: Artificial Sequence
<220> FEATURE:
<223> OTHER INFORMATION: huMov19 Light 1.00

<400> SEQUENCE: 51

Asp Ile Val Leu Thr Gln Ser Pro Leu Ser Leu Ala Val Ser Leu Gly
1               5                   10                  15

Gln Pro Ala Ile Ile Ser Cys Lys Ala Ser Gln Ser Val Ser Phe Ala
            20                  25                  30

Gly Thr Ser Leu Met His Trp Tyr His Gln Lys Pro Gly Gln Gln Pro
        35                  40                  45

Arg Leu Leu Ile Tyr Arg Ala Ser Asn Leu Glu Ala Gly Val Pro Asp
    50                  55                  60

Arg Phe Ser Gly Ser Gly Ser Lys Thr Asp Phe Thr Leu Asn Ile Ser
65                  70                  75                  80

Pro Val Glu Ala Glu Asp Ala Ala Thr Tyr Tyr Cys Gln Gln Ser Arg
                85                  90                  95

Glu Tyr Pro Tyr Thr Phe Gly Gly Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 52
<211> LENGTH: 218
<212> TYPE: PRT
<213> ORGANISM: Artificial Sequence
<220> FEATURE:
<223> OTHER INFORMATION: huMov19 Light 1.60

<400> SEQUENCE: 52

Asp Ile Val Leu Thr Gln Ser Pro Leu Ser Leu Ala Val Ser Leu Gly
1               5                   10                  15

Gln Pro Ala Ile Ile Ser Cys Lys Ala Ser Gln Ser Val Ser Phe Ala
            20                  25                  30

Gly Thr Ser Leu Met His Trp Tyr Gln Gln Lys Pro Gly Gln Gln Pro
        35                  40                  45

Arg Leu Leu Ile Tyr Arg Ala Ser Asn Leu Glu Ala Gly Val Pro Asp
    50                  55                  60

Arg Phe Ser Gly Ser Gly Ser Lys Thr Asp Phe Thr Leu Thr Ile Ser

```
            65                  70                  75                  80
    Pro Val Glu Ala Glu Asp Ala Ala Thr Tyr Tyr Cys Gln Gln Ser Arg
                        85                  90                  95

Glu Tyr Pro Tyr Thr Phe Gly Gly Gly Thr Lys Leu Glu Ile Lys Arg
                100                 105                 110

Thr Val Ala Ala Pro Ser Val Phe Ile Phe Pro Pro Ser Asp Glu Gln
                115                 120                 125

Leu Lys Ser Gly Thr Ala Ser Val Val Cys Leu Leu Asn Asn Phe Tyr
        130                 135                 140

Pro Arg Glu Ala Lys Val Gln Trp Lys Val Asp Asn Ala Leu Gln Ser
    145                 150                 155                 160

Gly Asn Ser Gln Glu Ser Val Thr Glu Gln Asp Ser Lys Asp Ser Thr
                    165                 170                 175

Tyr Ser Leu Ser Ser Thr Leu Thr Leu Ser Lys Ala Asp Tyr Glu Lys
                180                 185                 190

His Lys Val Tyr Ala Cys Glu Val Thr His Gln Gly Leu Ser Ser Pro
                195                 200                 205

Val Thr Lys Ser Phe Asn Arg Gly Glu Cys
                210                 215

<210> SEQ ID NO 53
<211> LENGTH: 447
<212> TYPE: PRT
<213> ORGANISM: Artificial Sequence
<220> FEATURE:
<223> OTHER INFORMATION: Z4681A Heavy

<400> SEQUENCE: 53

Gln Val Gln Leu Gln Gln Pro Gly Ala Glu Val Val Lys Pro Gly Ala
    1               5                   10                  15

Ser Val Lys Met Ser Cys Lys Ala Ser Gly Tyr Thr Phe Thr Ser Tyr
                20                  25                  30

Tyr Ile His Trp Ile Lys Gln Thr Pro Gly Gln Gly Leu Glu Trp Val
                35                  40                  45

Gly Val Ile Tyr Pro Gly Asn Asp Asp Ile Ser Tyr Asn Gln Lys Phe
        50                  55                  60

Gln Gly Lys Ala Thr Leu Thr Ala Asp Lys Ser Ser Thr Thr Ala Tyr
    65                  70                  75                  80

Met Gln Leu Ser Ser Leu Thr Ser Glu Asp Ser Ala Val Tyr Tyr Cys
                    85                  90                  95

Ala Arg Glu Val Arg Leu Arg Tyr Phe Asp Val Trp Gly Gln Gly Thr
                100                 105                 110

Thr Val Thr Val Ser Ser Ala Ser Thr Lys Gly Pro Ser Val Phe Pro
                115                 120                 125

Leu Ala Pro Ser Ser Lys Ser Thr Ser Gly Gly Thr Ala Ala Leu Gly
        130                 135                 140

Cys Leu Val Lys Asp Tyr Phe Pro Glu Pro Val Thr Val Ser Trp Asn
    145                 150                 155                 160

Ser Gly Ala Leu Thr Ser Gly Val His Thr Phe Pro Ala Val Leu Gln
                    165                 170                 175

Ser Ser Gly Leu Tyr Ser Leu Ser Val Val Thr Val Pro Ser Ser
                180                 185                 190

Ser Leu Gly Thr Gln Thr Tyr Ile Cys Asn Val Asn His Lys Pro Ser
                195                 200                 205

Asn Thr Lys Val Asp Lys Lys Val Glu Pro Lys Ser Cys Asp Lys Thr
```

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly
        435                 440                 445

<210> SEQ ID NO 54
<211> LENGTH: 219
<212> TYPE: PRT
<213> ORGANISM: Artificial Sequence
<220> FEATURE:
<223> OTHER INFORMATION: Z4681A Light

<400> SEQUENCE: 54

Glu Ile Val Leu Thr Gln Ser Pro Gly Ser Leu Ala Val Ser Pro Gly
1               5                   10                  15

Glu Arg Val Thr Met Ser Cys Lys Ser Ser Gln Ser Val Phe Phe Ser
            20                  25                  30

Ser Ser Gln Lys Asn Tyr Leu Ala Trp Tyr Gln Gln Ile Pro Gly Gln
        35                  40                  45

Ser Pro Arg Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Pro Glu Asp Leu Ala Ile Tyr Tyr Cys His Gln
                85                  90                  95

Tyr Leu Ser Ser Arg Thr Phe Gly Gln Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe

```
                130                 135                 140
Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 55
<211> LENGTH: 450
<212> TYPE: PRT
<213> ORGANISM: Artificial Sequence
<220> FEATURE:
<223> OTHER INFORMATION: G4723A Heavy

<400> SEQUENCE: 55

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ile Phe Thr Ser Ser
            20                  25                  30

Ile Met His Trp Val Arg Gln Ala Pro Gly Gln Gly Leu Glu Trp Ile
        35                  40                  45

Gly Tyr Ile Lys Pro Tyr Asn Asp Gly Thr Lys Tyr Asn Glu Lys Phe
    50                  55                  60

Lys Gly Arg Ala Thr Leu Thr Ser Asp Arg Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Gly Gly Asn Asp Tyr Tyr Asp Thr Met Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
```

```
                275                 280                 285
His Asn Ala Lys Thr Lys Pro Arg Glu Glu Gln Tyr Asn Ser Thr Tyr
290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly
    450

<210> SEQ ID NO 56
<211> LENGTH: 214
<212> TYPE: PRT
<213> ORGANISM: Artificial Sequence
<220> FEATURE:
<223> OTHER INFORMATION: G4723A Light

<400> SEQUENCE: 56

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Asn Ser Tyr
            20                  25                  30

Leu Ser Trp Phe Gln Gln Lys Pro Gly Lys Ala Pro Lys Thr Leu Ile
        35                  40                  45

Tyr Arg Val Asn Arg Leu Val Asp Gly Val Pro Ser Arg Phe Ser Gly
    50                  55                  60

Ser Gly Ser Gly Asn Asp Tyr Thr Leu Thr Ile Ser Ser Leu Gln Pro
65                  70                  75                  80

Glu Asp Phe Ala Thr Tyr Tyr Cys Leu Gln Tyr Asp Ala Phe Pro Tyr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
```

```
              180                 185                 190
Ala Cys Glu Val Thr His Gln Gly Leu Ser Ser Pro Val Thr Lys Ser
            195                 200                 205

Phe Asn Arg Gly Glu Cys
    210
```

METHODS FOR ANTIBODY DRUG CONJUGATION, PURIFICATION, AND FORMULATION

CROSS-REFERENCE TO RELATED APPLICATIONS

This application claims the benefit of U.S. Provisional Appl. Nos. 62/673,535, filed May 18, 2018 and 62/617,021, filed Jan. 12, 2018, each of which is herein incorporated by reference.

REFERENCE TO SEQUENCE LISTING SUBMITTED ELECTRONICALLY

The content of the electronically submitted sequence listing, file name: 29210990002_ST25.txt; size: 41,189 bytes; and date of creation: Jan. 9, 2019, filed herewith, is incorporated herein by reference in its entirety.

FIELD OF THE INVENTION

The field of the invention generally relates to methods of producing, purifying, and formulating antibody drug conjugates (ADCs) using continuous conjugation processes, single-pass tangential flow filtration, countercurrent diafiltration, and/or in-line process automation technologies.

BACKGROUND

A manufacturing bottleneck associated with antibody drug conjugate (ADC) conjugation is removal of impurities and exchange of the ADC into a stable buffer. This is currently achieved using bind and elute column chromatography or bulk (conventional) diafiltration by tangential flow filtration (TFF). Bulk diafiltration involves priming the TFF system with buffer A (i.e., the buffer that the conjugate is initially in). The ADC (in buffer A) is then added to a retentate vessel where it mixes with the prime volume. A feed pump for the retentate vessel pumps the conjugate from the retentate over the TFF membrane where it is either retained (and returns to the retentate) or discarded to waste. Another pump (the diafiltration pump) would feed from the vessel to buffer B contained in a separate vessel (i.e., the buffer into which the ADC will be exchanged) with a feed line from the vessel into the retentate vessel. Both pumps are started and the conjugate in the retentate vessel begins passing over the TFF membrane. As buffer is removed via the waste stream, the volume in the retentate is maintained by adding Buffer B (in equal volume) to the retentate vessel. As a result, the conjugate slowly is exchanged into Buffer B. This purification method is costly and not optimal for large-scale manufacturing because of the requirement to recirculate the ADC over the TFF membranes for multiple cycles. The recirculation results in high processing volumes and times as well as increased exposure of the ADC to potentially high shear zones. ADC manufacturing using bulk processing takes about 4-5 days to produce a batch of purified, formulated conjugate, often times at low yields. Accordingly, improved ADC conjugation processes are needed.

BRIEF SUMMARY OF THE INVENTION

Single-pass tangential flow filtration (SPTFF) systems such as those available from Pall Life Sciences are used in bioprocessing platforms, often as a way to reduce volume or concentrate biomolecules such as antibodies. However, the present inventors have surprisingly discovered that SPTFF can be linked to antibody drug conjugation reactions to facilitate, not only the concentration of antibody drug conjugates (ADCs), but also to remove unconjugated products from the conjugation reaction and exchange the purified ADC into a formulation buffer, thereby enabling an entirely continuous ADC production and processing method. The present inventors have also discovered that countercurrent diafilitration can also be used in antibody drug conjugation reactions for similar purposes.

In some embodiments, a continuous method for producing an antibody drug conjugate (ADC) composition comprises (i) conjugating an antibody or antigen-binding fragment thereof to a drug to form an ADC, (ii) removing unconjugated drug, and (iii) exchanging the ADC into a stable buffer, wherein (i) to (iii) are performed continuously, and wherein single-pass tangential flow filtration (SPTFF) is used to remove the unconjugated drug and/or exchange the ADC into the stable buffer.

In some embodiments, SPTFF is used to remove the unconjugated drug to exchange the ADC into the stable buffer. In some embodiments, flow-through column chromatography is used to remove the unconjugated drug and SPTFF is used to exchange the ADC into the stable buffer.

In some embodiments, a continuous method for producing an antibody drug conjugate (ADC) composition comprises (i) conjugating an antibody or antigen-binding fragment thereof to a drug to form an ADC, (ii) removing unconjugated drug, and (iii) exchanging the ADC into a stable buffer, wherein (i) to (iii) are performed continuously, and wherein countercurrent diafilitration is used to remove the unconjugated drug and/or exchange the ADC into the stable buffer.

In some embodiments, countercurrent diafilitration is used to remove the unconjugated drug to exchange the ADC into the stable buffer. In some embodiments, flow-through column chromatography is used to remove the unconjugated drug and countercurrent diafilitration is used to exchange the ADC into the stable buffer.

In some embodiments, the method further comprises pre-processing the antibody or antigen-binding fragment thereof. In some embodiments, the pre-processing of the antibody or antigen-binding fragment thereof is performed continuously with (i) to (iii). In some embodiments, the pre-processing of the antibody or antigen-binding fragment thereof is performed using SPTFF. In some embodiments, the pre-processing of the antibody or antigen-binding fragment thereof is performed using countercurrent diafilitration. In some embodiments, only one SPTFF or countercurrent diafilitration step is used in the pre-processing. In some embodiments, the pre-processing of the antibody or antigen-binding fragment thereof is performed in bulk prior to (i) to (iii).

In some embodiments, the method further comprises pre-processing the drug for conjugation.

In some embodiments, a continuous method for producing an antibody drug conjugate (ADC) composition comprises (i) pre-processing an antibody or antigen-binding fragment thereof, (ii) conjugating the antibody or antigen-binding fragment thereof to a drug to form an ADC, (iii) removing unconjugated drug, and (iv) exchanging the ADC into a stable buffer, wherein (i) to (iv) are performed continuously, and wherein single-pass tangential flow filtration (SPTFF) is used to remove the unconjugated drug and/or exchange the ADC into the stable buffer.

In some embodiments, a continuous method for producing an antibody drug conjugate (ADC) composition comprises (i) pre-processing an antibody or antigen-binding fragment thereof, (ii) conjugating the antibody or antigen-binding fragment thereof to a drug to form an ADC, (iii) removing unconjugated drug, and (iv) exchanging the ADC into a stable buffer, wherein (i) to (iv) are performed continuously, and wherein countercurrent diafiltration is used to remove the unconjugated drug and/or exchange the ADC into the stable buffer.

In some embodiments, the pre-processing of the antibody or antigen-binding fragment thereof comprises exchanging the antibody or antigen-binding fragment thereof into a buffer for conjugation. In some embodiments, the pre-processing of the antibody or antigen-binding fragment thereof comprises reducing the antibody or antigen-binding fragment thereof and/or oxidizing the antibody or antigen-binding fragment thereof. In some embodiments, the reducing and/or the oxidizing are achieved without using SPTFF or countercurrent diafiltration. In some embodiments, the reducing and/or the oxidizing are achieved using only one SPTFF or countercurrent diafiltration step. In some embodiments, the reducing and/or the oxidizing are achieved using more than one SPTFF or countercurrent diafiltration step.

In some embodiments, a method for producing an antibody drug conjugate (ADC) in a continuous conjugation process comprises adding one or more conjugation reaction reagents to a conjugation reaction while the conjugation reaction proceeds and after at least one conjugation reaction product (ADC) has formed. In some embodiments, the conjugation reaction reagent comprises an antibody or antigen-binding fragment thereof. In some embodiments, the conjugation reaction reagent comprises a drug attached to a linker. In some embodiments, the conjugation reaction reagent comprises a linker. In some embodiment, the conjugation reaction reagent comprises an antibody or antigen-binding fragment thereof attached to a linker. In some embodiments, the conjugation reaction reagent comprises a drug.

In some embodiments, the conjugation reaction occurs in a flow reactor.

In some embodiments, the method further comprises pre-processing an antibody or antigen-binding fragment thereof. In some embodiments, the pre-processing of the antibody or antigen-binding fragment thereof is performed continuously with the conjugation reaction. In some embodiments, the pre-processing of the antibody or antigen-binding fragment thereof is performed using SPTFF. In some embodiments, the pre-processing of the antibody or antigen-binding fragment thereof is performed using countercurrent diafiltration. In some embodiments, only one SPTFF or countercurrent diafiltration step is used in the pre-processing. In some embodiments, the pre-processing of the antibody or antigen-binding fragment thereof is performed in bulk prior to the conjugation reaction. In some embodiments, the pre-processing of the antibody or antigen-binding fragment thereof comprises exchanging the antibody or antigen-binding fragment thereof into a buffer for conjugation. In some embodiments, the pre-processing of the antibody or antigen-binding fragment thereof comprises reducing the antibody or antigen-binding fragment thereof and/or oxidizing the antibody or antigen-binding fragment thereof.

In some embodiments, the ADC is concentrated using single-pass tangential flow filtration. In some embodiments, the ADC is purified using single-pass tangential flow filtration. In some embodiments, the ADC is transferred to a formulation buffer using single-pass tangential flow filtration.

In some embodiments, the ADC is concentrated using countercurrent diafiltration. In some embodiments, the ADC is purified using countercurrent diafiltration. In some embodiments, the ADC is transferred to a formulation buffer using countercurrent diafiltration.

In some embodiments, the ADC is concentrated, purified, and/or transferred to a formulation buffer using flow-through chromatography.

In some embodiments, a method for concentrating an antibody drug conjugate (ADC) comprises using single-pass tangential flow filtration. In some embodiments, a method for purifying an antibody drug conjugate (ADC) comprises using single-pass tangential flow filtration. In some embodiments, a method for transferring an antibody drug conjugate (ADC) to a formulation buffer comprises using single-pass tangential flow filtration. In some embodiments, a method for concentrating an antibody drug conjugate (ADC) comprises using countercurrent diafiltration. In some embodiments, a method for purifying an antibody drug conjugate (ADC) comprises using countercurrent diafiltration. In some embodiments, a method for transferring an antibody drug conjugate (ADC) to a formulation buffer comprises using countercurrent diafiltration. In some embodiments, the ADC was produced in a batch conjugation process. In some embodiments, the ADC was produced in a continuous conjugation process.

In some embodiments, the single-pass tangential flow filtration uses an ultrafiltration membrane. In some embodiments, the single-pass tangential flow filtration uses a diafiltration membrane.

In some embodiments, the method improves the consistency of the ADC production. In some embodiments, the method decreases the time for ADC production.

In some embodiments, the single-pass tangential flow filtration improves the consistency of the ADC production. In some embodiments, the single-pass tangential flow filtration decreases the time for ADC concentration, purification, or transfer. In some embodiments, the single-pass tangential flow filtration decreases the amount of buffer used.

In some embodiments, the countercurrent diafiltration improves the consistency of the ADC production. In some embodiments, the countercurrent diafiltration decreases the time for ADC concentration, purification, or transfer. In some embodiments, the countercurrent diafiltration decreases the amount of buffer used.

In some embodiments, the method further comprises in-line monitoring of an analyte.

In some embodiments, a method for producing an antibody drug conjugate (ADC) comprising using in-line monitoring to measure the addition of a component to an ADC conjugation reaction.

In some embodiments, the in-line monitoring measures the concentration of a component added to the ADC conjugation reaction.

In some embodiments, the in-line monitoring measures the flow rate of a component added to the ADC conjugation reaction. In some embodiments, the component is an antibody or antigen-binding fragment thereof, a drug, a linker, drug attached to a linker, an antibody or antigen-binding fragment thereof attached to a linker, and/or a conjugation buffer.

In some embodiments, the method further comprises in-line monitoring to measure the addition of a component to an in-situ reaction. In some embodiments, the component is a drug, a linker, and/or an in-situ reaction buffer.

In some embodiments, a method for producing an antibody drug conjugate (ADC) comprises in-line monitoring of an analyte to determine when (i) to stop adding conjugation buffer to an ADC conjugation reaction (ii) to stop recirculating conjugation buffer in an ADC conjugation reaction, and/or (iii) to start rinsing conjugation buffer from an ADC conjugation reaction. In some embodiments, the analyte is unconjugated drug or unconjugated drug attached to linker.

In some embodiments, a method for purifying an antibody drug conjugate (ADC) after an ADC conjugation process comprises in-line monitoring of an analyte. In some embodiments, the purification comprises filtration. In some embodiments, the filtration is ultrafiltration or diafiltration. In some embodiments, the filtration is tangential flow filtration. In some embodiments, the tangential flow filtration is single-pass tangential flow filtration. In some embodiments, the filtration is countercurrent diafiltration.

In some embodiments, the analyte is in the retentate. In some embodiments, the analyte is the concentration of unconjugated drug or unconjugated drug attached to linker. In some embodiments, the analyte is the concentration of an ADC or an antibody or antigen-binding fragment thereof. In some embodiments, the analyte is the concentration of a component of a conjugation reaction buffer or a filtration buffer.

In some embodiments, the analyte is the pH.

In some embodiments, the analyte is in the permeate. In some embodiments, the analyte is the concentration of an ADC or an antibody or antigen-binding fragment thereof. In some embodiments, the analyte is the concentration of unconjugated drug or unconjugated drug attached to linker.

In some embodiments, the purification comprises chromatography, and the analyte is measured at the end of a chromatography column. In some embodiments, the analyte is an ADC or an antibody or antigen-binding fragment thereof. In some embodiments, the analyte is unconjugated drug, unconjugated drug attached to linker, a component of a conjugation reaction buffer, or a component of a chromatography buffer.

In some embodiments, the conjugation reaction is a batch conjugation reaction. In some embodiments, the conjugation reaction is a continuous conjugation reaction.

In some embodiments, the in-line monitoring is performed using variable path-length technology, a flow cell device, a UV sensor, Raman spectroscopy, or Fourier Transform Infrared spectroscopy (FITR).

In some embodiments, the in-line monitoring of the analyte is performed using a FlowVPE.

In some embodiments, the in-line monitoring improves ADC yield. In some embodiments, the in-line monitoring improves ADC recovery. In some embodiments, the in-line monitoring decreases time for ADC production. In some embodiments, the in-line monitoring decreases the amount of buffer used.

In some embodiments, a method for producing an antibody drug conjugate (ADC) comprises in-line monitoring of an analyte to determine when to stop adding a conjugation reaction component to an ADC conjugation reaction. In some embodiments, the component is an antibody or antigen-binding fragment thereof, a drug, a linker, a drug attached to a linker, and/or a conjugation reaction buffer.

In some embodiments, the ADC comprises an antibody. In some embodiments, wherein the ADC comprises an antigen-binding fragment of an antibody. In some embodiments, the ADC comprises an antibody or antigen-binding fragment that specifically binds to CD37, CD33, FOLR1, CD123, CD19, cMET, ADAMS, or HER2. In some embodiments, the antibody or antigen-binding fragment thereof comprises the VH CDR1, VH CDR2, VH CDR3, VL CDR1, VL CDR2, and VL CDR3 of huMov19, Z4681A, or G4732A. In some embodiments, the CDRs are the Kabat-defined CDRs, the Chothia-defined CDRs, or the AbM-defined CDRs. In some embodiments, the antibody or antigen-binding fragment thereof comprises VH CDR1, VH CDR2, VH CDR3, VL CDR1, VL CDR2, and VL CDR3 sequences comprising the sequences of SEQ ID NOs:1-6, respectively, SEQ ID NOs:7-12, respectively, SEQ ID NOs:13-18, respectively, SEQ ID NOs:19-24, respectively, SEQ ID NOs:25-30, or respectively, SEQ ID NOs:31-36, respectively. In some embodiments, the antibody or antigen-binding fragment thereof comprises VH and VL sequences comprising the sequence of SEQ ID NOs:37 and 38, respectively, SEQ ID NOs:37 and 39, respectively, SEQ ID NOs:40 and 41, respectively, SEQ ID NOs:42 and 43, respectively, SEQ ID NOs:44 and 45, respectively, SEQ ID NOs: 46 and 47, respectively, or SEQ ID NOs:48 and 49, respectively. In some embodiments, the antibody comprises heavy and light chain sequences comprising the sequences of SEQ ID NOs: 50 and 51, respectively, SEQ ID NOs:50 and 52, respectively, SEQ ID NOs:53 and 54, respectively, or SEQ ID NOs:55 and 56, respectively.

In some embodiments, the ADC comprises a linker selected from the group consisting of SMCC, sSPDB, and a peptide linker. In some embodiments, the ADC comprises a maytansinoid or an indolino-benzodiazepine. In some embodiments, the maytansinoid is DM1 or DM4. In some embodiments, the indolino-benzodiazepine is DGN462 or DGN549.

In some embodiments, the ADC is IMGN529, IMGN779, IMGN853, IMGN632, or Kadcyla.

In some embodiments, a method for producing IMGN853 comprises (i) mixing huMov19 antibody and DM4-linked to sulfo-SPDB in a continuous conjugation process to form IMGN853, optionally wherein in-line monitoring is used to measure the concentration of huMov19 antibody added to the conjugation reaction, (ii) optionally concentrating IMGN853 using single-pass tangential flow filtration, optionally wherein in-line monitoring is used to measure the concentration of unconjugated drug in the retentate, (iii) purifying IMGN853 using single-pass tangential flow filtration, optionally wherein in-line monitoring is used to measure the concentration of unconjugated drug in the retentate, and (iv) exchanging the IMGN853 into a formulation buffer using single-pass tangential flow filtration, optionally wherein in-line monitoring is used to measure the concentration of impurities in the retentate.

In some embodiments, a method for producing IMGN853 comprises (i) mixing huMov19 antibody and DM4-linked to sulfo-SPDB in a continuous conjugation process to form IMGN853, optionally wherein in-line monitoring is used to measure the concentration of huMov19 antibody added to the conjugation reaction, (ii) optionally concentrating IMGN853 using single-pass tangential flow filtration and/or countercurrent diafiltration, optionally wherein in-line monitoring is used to measure the concentration of unconjugated drug in the retentate, (iii) purifying IMGN853 using single-pass tangential flow filtration and/or countercurrent diafiltration, optionally wherein in-line monitoring is used to measure the concentration of unconjugated drug in the retentate, and (iv) exchanging the IMGN853 into a formulation buffer using single-pass tangential flow filtration and/or countercurrent diafiltration, optionally wherein in-line monitoring is used to measure the concentration of impurities in the retentate.

In some embodiments, a method for producing IMGN779 comprises (i) mixing Z4681A antibody and DGN462-linked to sulfo-SPDB in a continuous conjugation process to form IMGN779, optionally wherein in-line monitoring is used to measure the concentration of Z4681A antibody added to the conjugation reaction, (ii) optionally concentrating IMGN779 using single-pass tangential flow filtration, optionally wherein in-line monitoring is used to measure the concentration of unconjugated drug in the retentate, (iii) purifying IMGN779 using single-pass tangential flow filtration, optionally wherein in-line monitoring is used to measure the concentration of unconjugated drug in the retentate, and (iv) exchanging the IMGN779 into a formulation buffer using single-pass tangential flow filtration, optionally wherein in-line monitoring is used to measure the concentration of impurities in the retentate.

In some embodiments, a method for producing IMGN779 comprises (i) mixing Z4681A antibody and DGN462-linked to sulfo-SPDB in a continuous conjugation process to form IMGN779, optionally wherein in-line monitoring is used to measure the concentration of Z4681A antibody added to the conjugation reaction, (ii) optionally concentrating IMGN779 using single-pass tangential flow filtration and/or countercurrent diafiltration, optionally wherein in-line monitoring is used to measure the concentration of unconjugated drug in the retentate, (iii) purifying IMGN779 using single-pass tangential flow filtration and/or countercurrent diafiltration, optionally wherein in-line monitoring is used to measure the concentration of unconjugated drug in the retentate, and (iv) exchanging the IMGN779 into a formulation buffer using single-pass tangential flow filtration and/or countercurrent diafiltration, optionally wherein in-line monitoring is used to measure the concentration of impurities in the retentate.

In some embodiments, a method for producing IMGN632 comprises (i) mixing G4732A antibody and sulfonated DNG549C in a continuous conjugation process to form IMGN632, (ii) optionally concentrating IMGN632 using single-pass tangential flow filtration, optionally wherein in-line monitoring is used to measure the concentration of unconjugated drug in the retentate, (iii) purifying IMGN632 using single-pass tangential flow filtration, optionally wherein in-line monitoring is used to measure the concentration of unconjugated drug in the retentate, and (iv) exchanging the IMGN632 into a formulation buffer using single-pass tangential flow filtration, optionally wherein in-line monitoring is used to measure the concentration of impurities in the retentate. In some embodiments, the G4732A antibody is reduced and oxidized in only one SPTFF step prior the conjugation process.

In some embodiments, a method for producing IMGN632 comprises (i) mixing G4732A antibody and sulfonated DNG549C in a continuous conjugation process to form IMGN632, (ii) optionally concentrating IMGN632 using single-pass tangential flow filtration and/or countercurrent diafiltration, optionally wherein in-line monitoring is used to measure the concentration of unconjugated drug in the retentate, (iii) purifying IMGN632 using single-pass tangential flow filtration and/or countercurrent diafiltration, optionally wherein in-line monitoring is used to measure the concentration of unconjugated drug in the retentate, and (iv) exchanging the IMGN632 into a formulation buffer using single-pass tangential flow filtration and/or countercurrent diafiltration, optionally wherein in-line monitoring is used to measure the concentration of impurities in the retentate. In some embodiments, the G4732A antibody is reduced and oxidized in only one SPTFF or countercurrent diafiltration step prior the conjugation process.

In some embodiments, the method comprises increasing a first temperature of a conjugation process by at least 5° C. to an elevated temperature, wherein the elevated temperature is maintained for no more than 20 minutes.

In some embodiments, a method of producing an ADC comprises increasing a first temperature of a conjugation process by at least 5° C. to an elevated temperature, wherein the elevated temperature is maintained for no more than 20 minutes.

In some embodiments, the elevated temperature is no more than 55° C. In some embodiments, the first temperature is increased by at least 10° C., by at least 15° C., by at least 20° C., or by at least 30° C.

In some embodiments, the elevated temperature is 35° C. to 55° C. or is 40° C. to 50° C.

In some embodiments, increasing the first temperature to the elevated temperature does not take longer than 2 minutes or does not take longer than 1 minute.

In some embodiments, the method further comprises decreasing the elevated temperature, optionally to the first temperature. In some embodiments, decreasing the elevated temperature, optionally to the first temperature, does not take longer than 2 minutes or does not take longer than 1 minute.

In some embodiments, the steps of increasing the first temperature to the elevated temperature and then decreasing the elevated temperature are repeated at least twice or at least three times. In some embodiments, the steps of increasing the first temperature to the elevated temperature and then decreasing the elevated temperature are repeated 2-20 times or 5-10 times.

In some embodiments, the method comprises decreasing a first temperature of a conjugation process by at least 5° C. to a reduced temperature, wherein the reduced temperature is maintained for no more than 20 minutes.

In some embodiments, a method of producing an ADC comprises decreasing a first temperature of a conjugation process by at least 5° C. to a reduced temperature, wherein the reduced temperature is maintained for no more than 20 minutes. In some embodiments, the first temperature is decreased by no more than 30° C. In some embodiments, the temperature is decreased by at least 10° C., by at least 15° C., or by at least 20° C.

In some embodiments, decreasing the first temperature to the reduced temperature does not take longer than 2 minutes or does not take longer than 1 minute.

In some embodiments, the method further comprises increasing the reduced temperature, optionally to the first temperature. In some embodiments, increasing the reduced temperature, optionally to the first temperature, does not take longer than 2 minutes or does not take longer than 1 minute.

In some embodiments, the steps of decreasing the first temperature to the reduced temperature and then increasing the reduced temperature are repeated at least twice or at least three times. In some embodiments, the steps of decreasing the first temperature to the reduced temperature and then increasing the reduced temperature are repeated 2-20 times or 5-10 times.

In some embodiments, wherein the elevated temperature or reduced temperature is maintained for no more than 15 minutes. In some embodiments, the elevated temperature or reduced temperature is maintained for 30 seconds to 15 minutes. In some embodiments, the elevated temperature or reduced temperature is maintained for 15 to 20 minutes. In some embodiments, the elevated temperature or reduced temperature is maintained for 10 to 15 minutes. In some embodiments, the elevated temperature or reduced temperature is maintained for 5 to 10 minutes. In some embodiments, the elevated temperature or reduced temperature is maintained for 1 to 5 minutes.

In some embodiments, the method comprises changing a first pH of a conjugation process by at least 0.5 to an altered pH, wherein the altered pH is maintained for no more than 20 minutes.

In some embodiments, a method of producing an ADC comprises changing a first pH of a conjugation process by at least 0.5 to an altered pH, wherein the altered pH is maintained for no more than 20 minutes.

In some embodiments, the first pH is increased by at least 1, optionally wherein the altered pH does not exceed 9. In some embodiments, the first pH is increased by at least 2 or by at least 3.

In some embodiments, the first pH is decreased by at least 1, optionally wherein the altered pH does not go below 4. In some embodiments, the first pH is decreased by at least 2 or by at least 3.

In some embodiments, the method further comprises changing the altered pH, optionally to the first pH. In some embodiments, the steps of changing the first pH to the altered pH and then changing the altered pH are repeated at least twice or at least three times. In some embodiments, the steps of changing the first pH to the altered pH and then changing the altered pH are repeated 2-20 times or 5-10 times.

In some embodiments, the altered pH is maintained for no more than 15 minutes. In some embodiments, the altered pH is maintained for 30 seconds to 15 minutes. In some embodiments, the altered pH is maintained for 15 to 20 minutes. In some embodiments, the altered pH is maintained for 10 to 15 minutes. In some embodiments, the altered pH is maintained for 5 to 10 minutes. In some embodiments, the altered pH is maintained for 1 to 5 minutes.

Also provided herein are ADCs produced according to the methods provided herein.

BRIEF DESCRIPTION OF THE DRAWINGS/FIGURES

Figure 5:
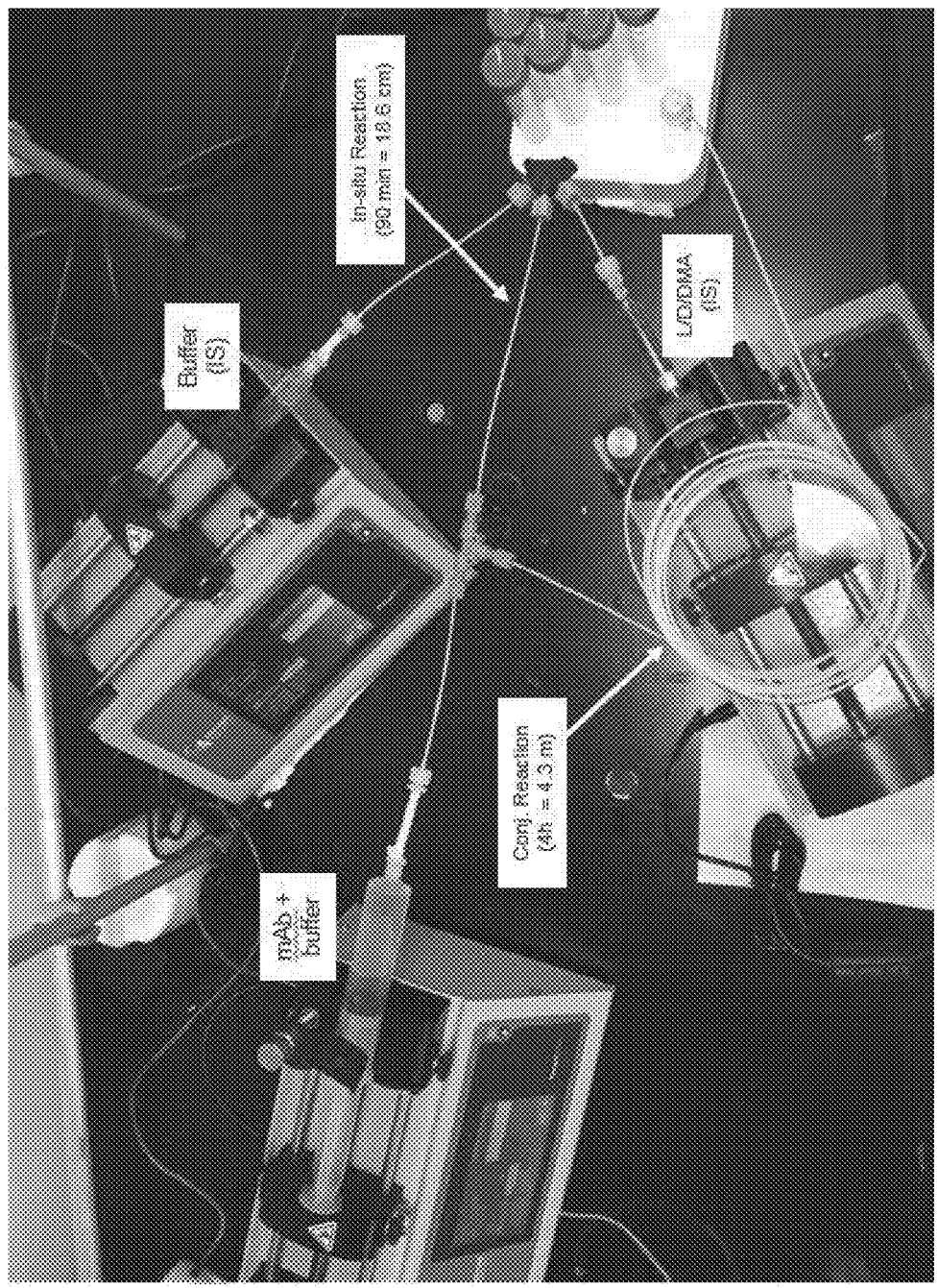

FIG. 5 shows the setup for continuous conjugation studies described in Example 1A. The first syringe pump (L/D/DMA) feeds the in-situ components dissolved in DMA. The Buffer (IS) syringe pump feeds the in-situ reaction buffer (same as conjugation reaction buffer, but pH is 7.6 for in-situ reaction). The third syringe feeds the antibody and pH 8.7 conjugation reaction buffer. "mAb" refers to monoclonal antibody (i.e., huMov19). "D" refers to drug (i.e., the maytansinoid DM4), and "L" refers to linker (i.e., sSPDB. "IS" refers to in-situ.

Figure 6:
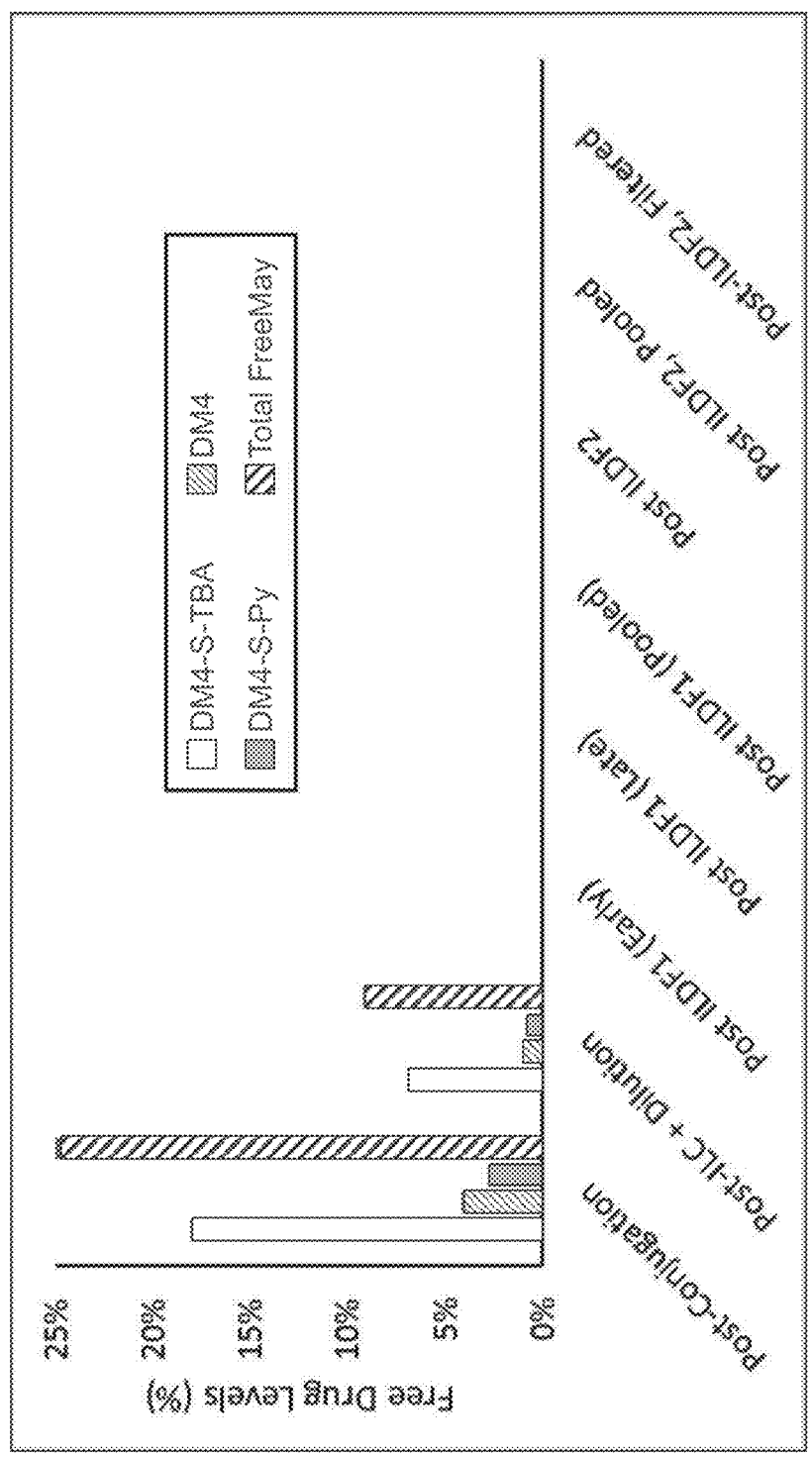

FIG. 6 shows free drug impurity levels for the four main impurity species in samples taken at the ILC, ILDF1 and ILDF2 stages described in Example 1B.

Figure 7:
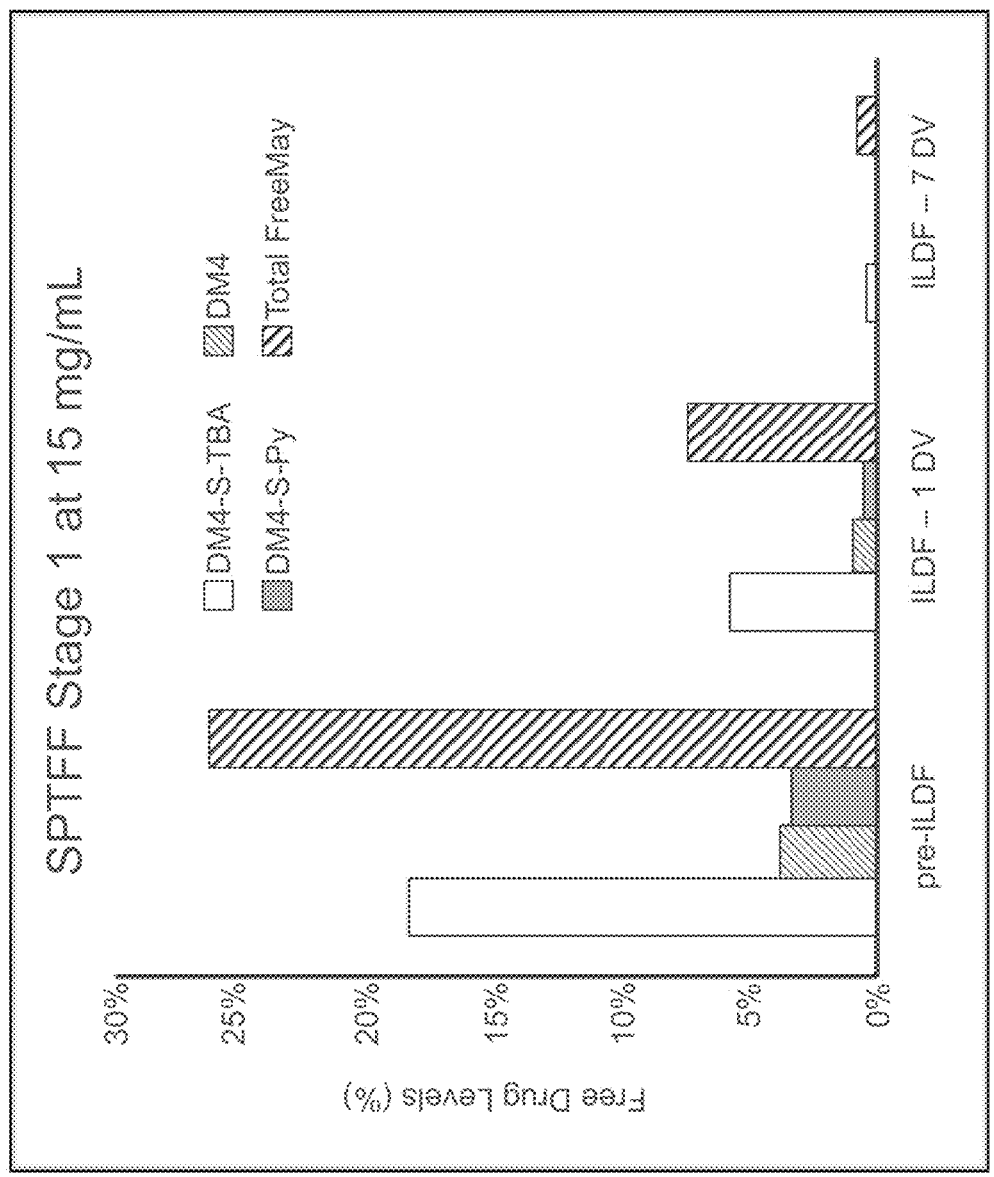

FIG. 7 shows free drug impurity levels for the four main impurity species in samples taken at ILDF1 at 15 mg/mL feed concentration as described in Example 1B.

Figure 8:
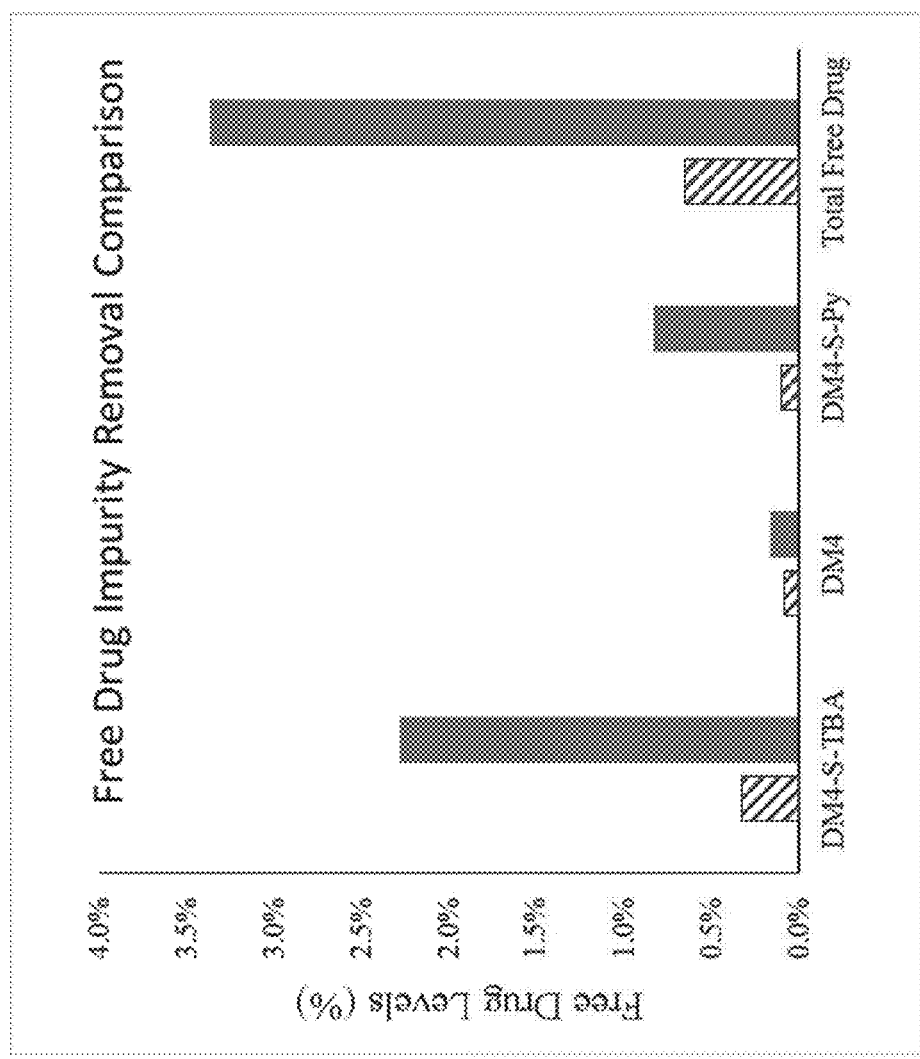

FIG. 8 shows a comparison of free drug impurity levels for continuous and batch TFF purification processes. The continuous (striped bars) conjugate material was processed at 15 g/L starting concentration whereas the batch (solid bars) material was processed at 30 g/L as described in Example 1B.

Figure 9:
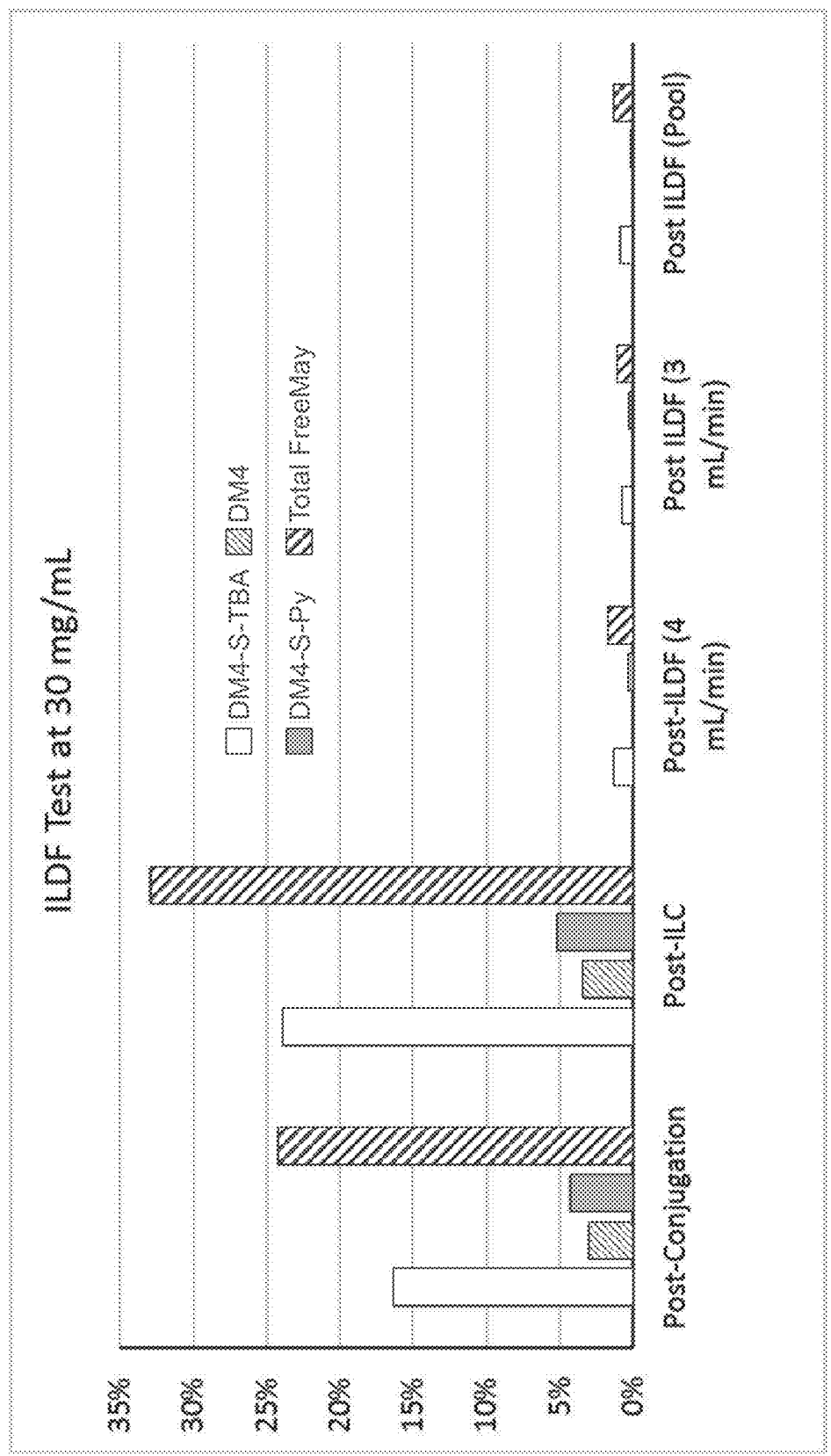

FIG. 9 shows free drug impurity levels for the four main impurity species in samples taken at ILDF1 at 30 mg/mL feed concentration as described in Example 1B.

Figure 10:
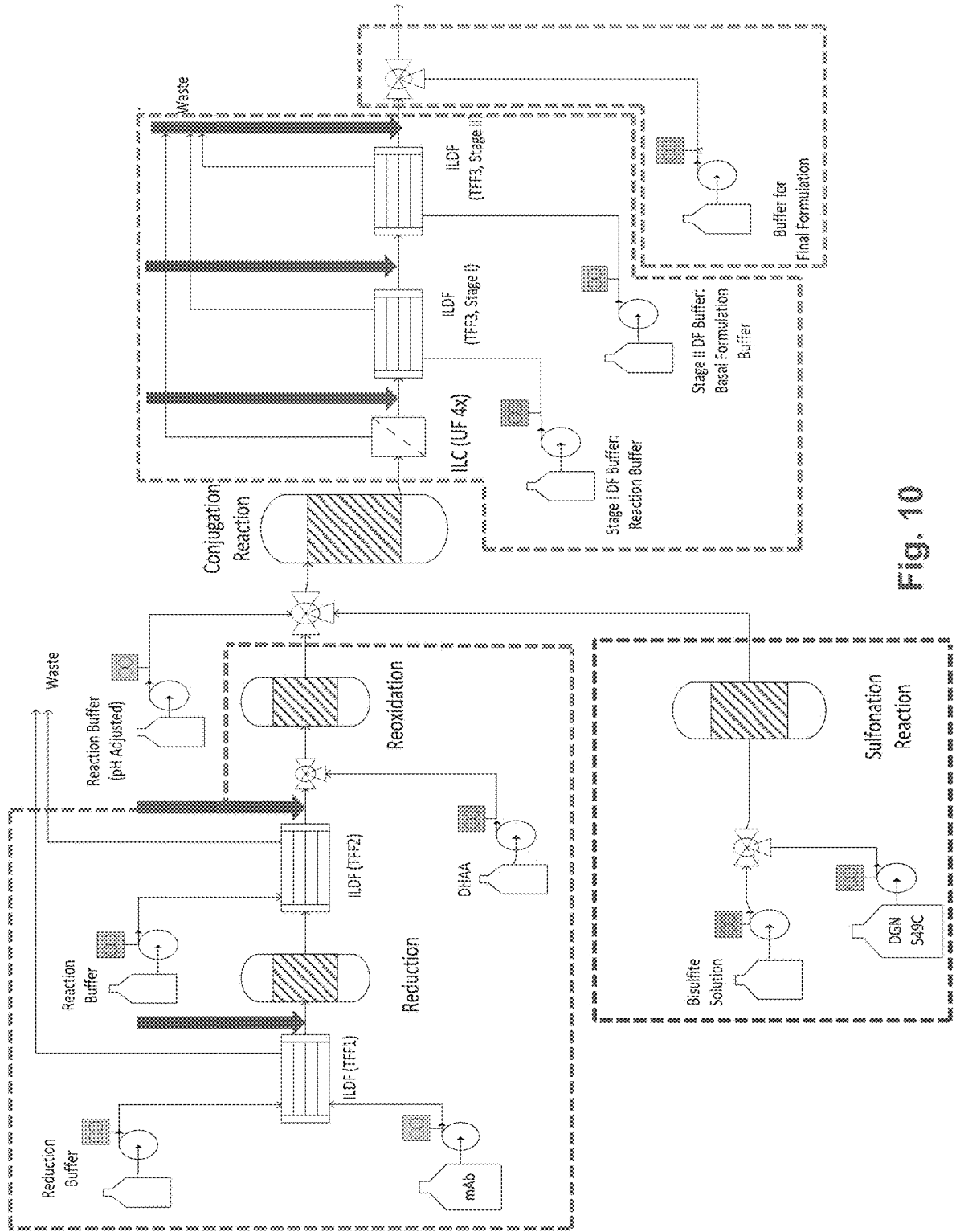

FIG. 10 is a flow diagram showing the continuous conjugation process for the conjugation of the antibody drug conjugate (ADC) "IMGN632" described in Example 2. "mAb" refers to monoclonal antibody (i.e., G4723A).

Figure 11:
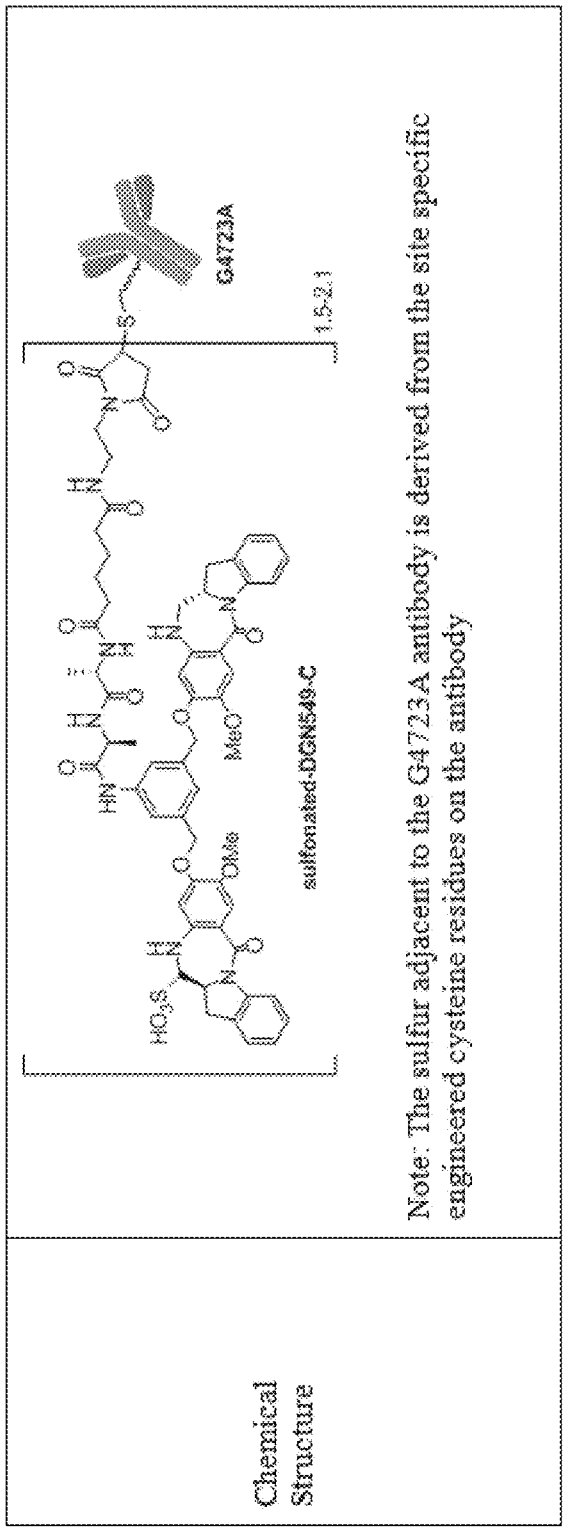
Figure 11:
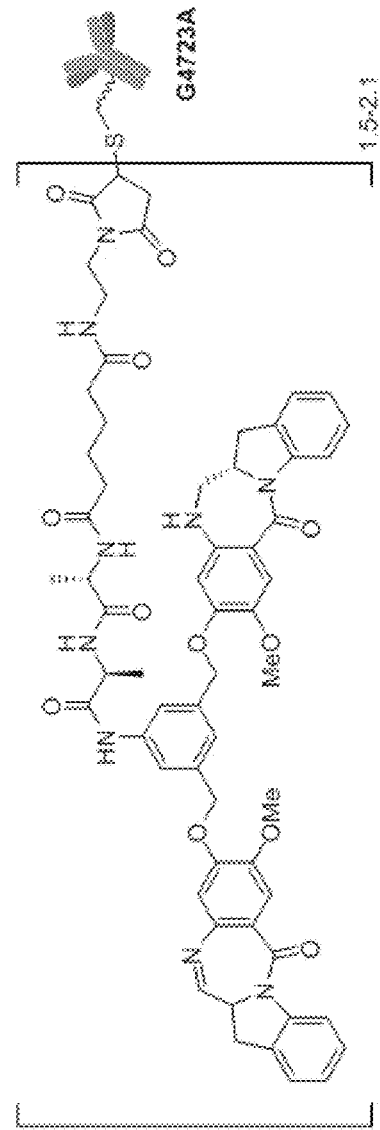

FIG. 11 shows the chemical structure for IMGN632. IMGN632 is a composition comprising ADCs containing the anti-CD123 G4723 antibody linked to the cytotoxic payload DGN549-C in sodium bisulfite. The majority of the ADC in the composition is in the sulfonated version shown in the top panel. The bottom panel shows an unsulfonated form of the ADC containing the anti-CD123 G4723 antibody linked to the cytotoxic payload DGN549-C (the monoimine structure), which can also be present in an IMGN632 composition.

Figure 12:
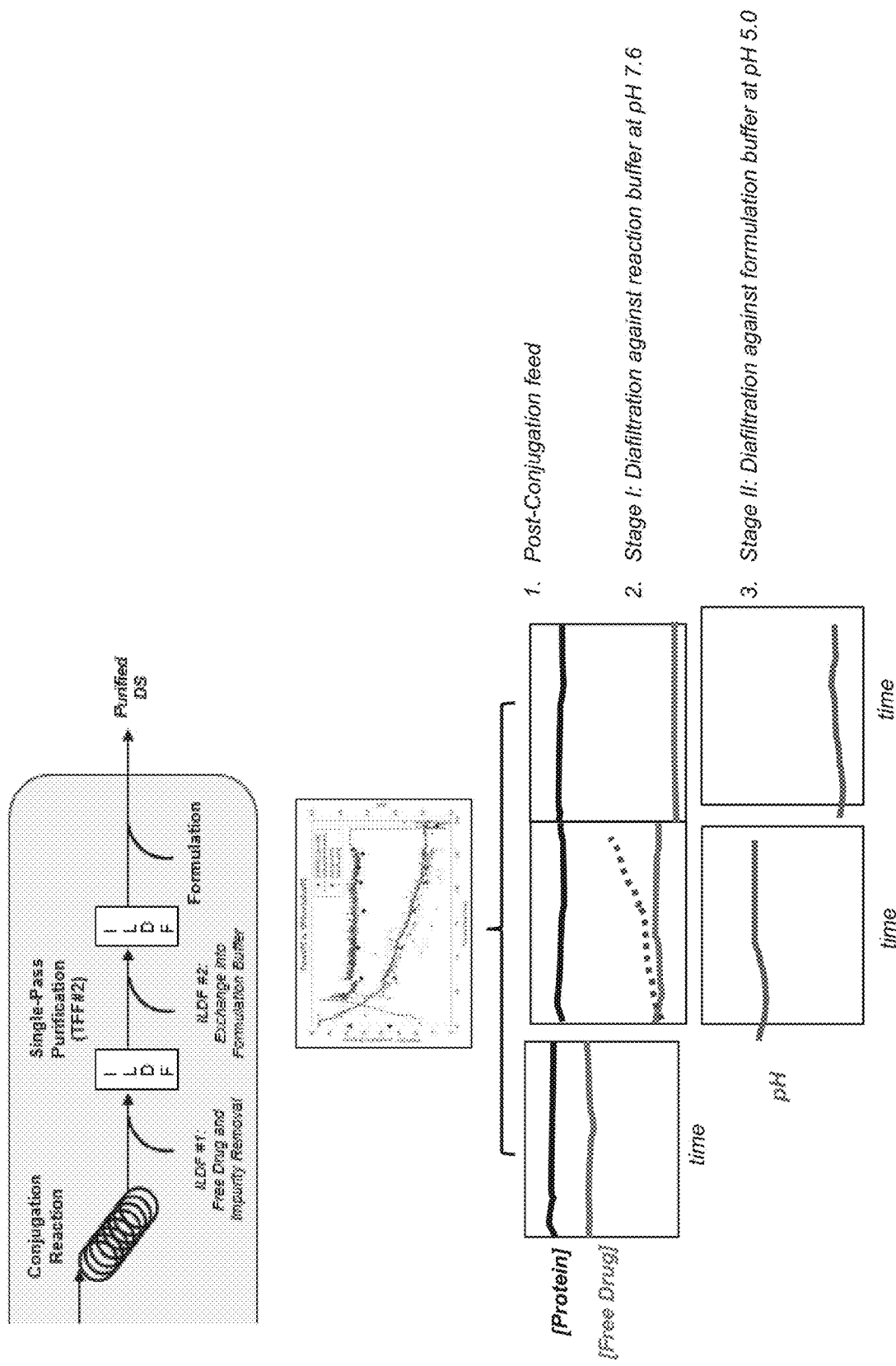

FIG. 12 shows how the use of in-line process automation technology (PAT) can be used to increase control and detectability. Changes during steady-state operation are used to detect issues before product quality is impacted. Ensure robust process performance across individual unit operations with multiple PAT modules used in combination. TFF: FlowVPE, UV sensors, pH meter, conductivity meter, pressure sensors, and flow meters. 1. Post-Conjugation feed: protein concentration at expected reaction concentration with high free drug levels. 2. Stage I: Diafiltration against reaction buffer at pH 7.6, Free drug drops and [Protein] remains constant, pH high. 3. Stage II: Diafiltration against formulation buffer at pH 5.0, [Protein] remains constant, slight drop in Free Drug, and pH drops to ensure buffer-exchange.

Figure 13:
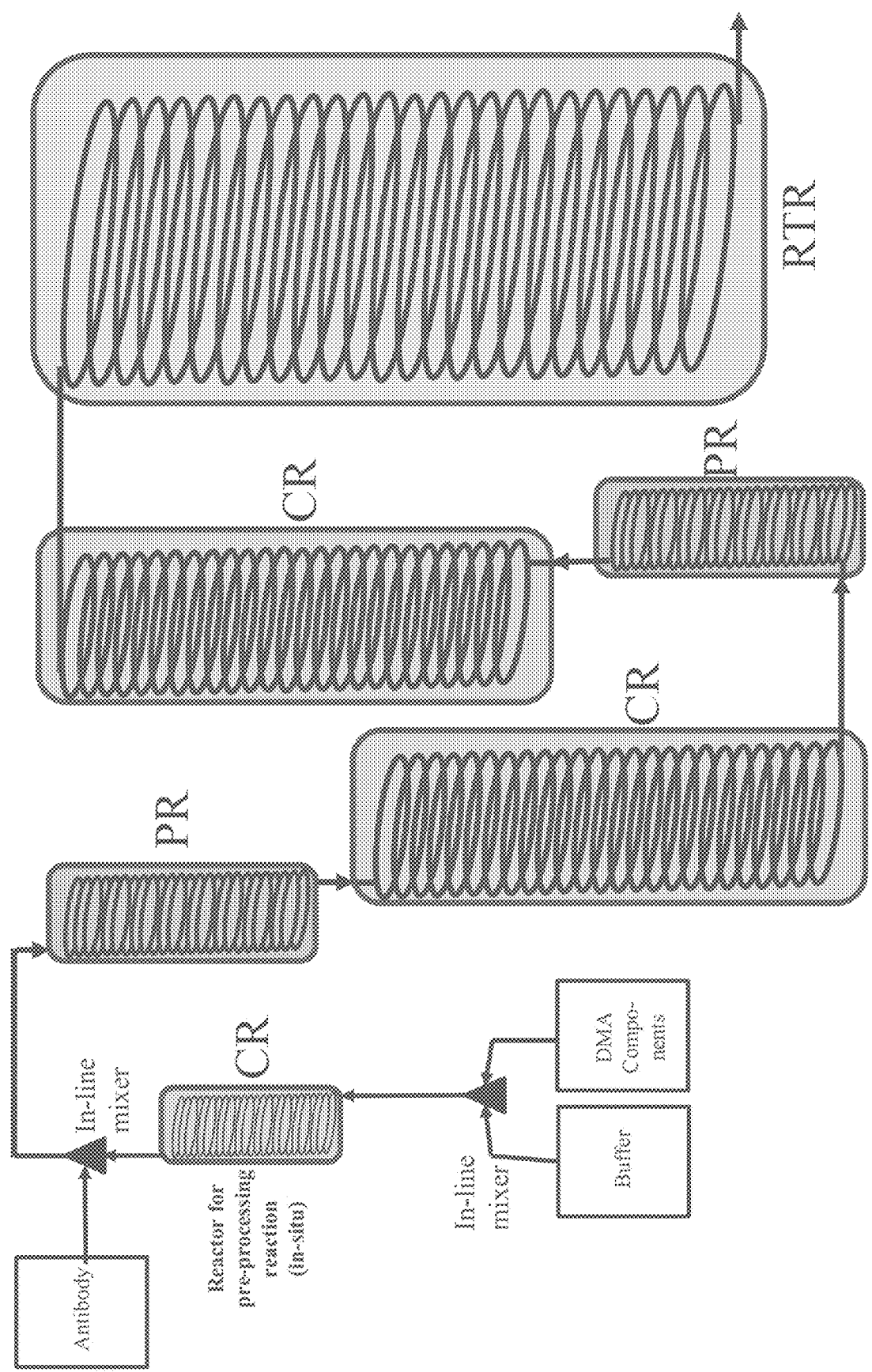

FIG. 13 shows a schematic of heating and cooling reactors that could be used to pulse a conjugation reaction with an elevated temperature. In the Pulsing Reactors (labeled "PR"), the jacket temperature is elevated so that the reaction components contained within the coil are heated temporarily to induce a short temperature excursion. Then, in the Cooling Reactors (labeled "CR"), the jacket temperature is kept at a cooler temperature to let the reaction components within the coil cool back down from the elevated temperature. This can reduce the amount of aggregation occurring during the reaction. The Residence Time Reactor (RTR) maintains the desired reaction temperature after pulsing is complete, and its volume can be based on the desired reaction time.

Figure 14:
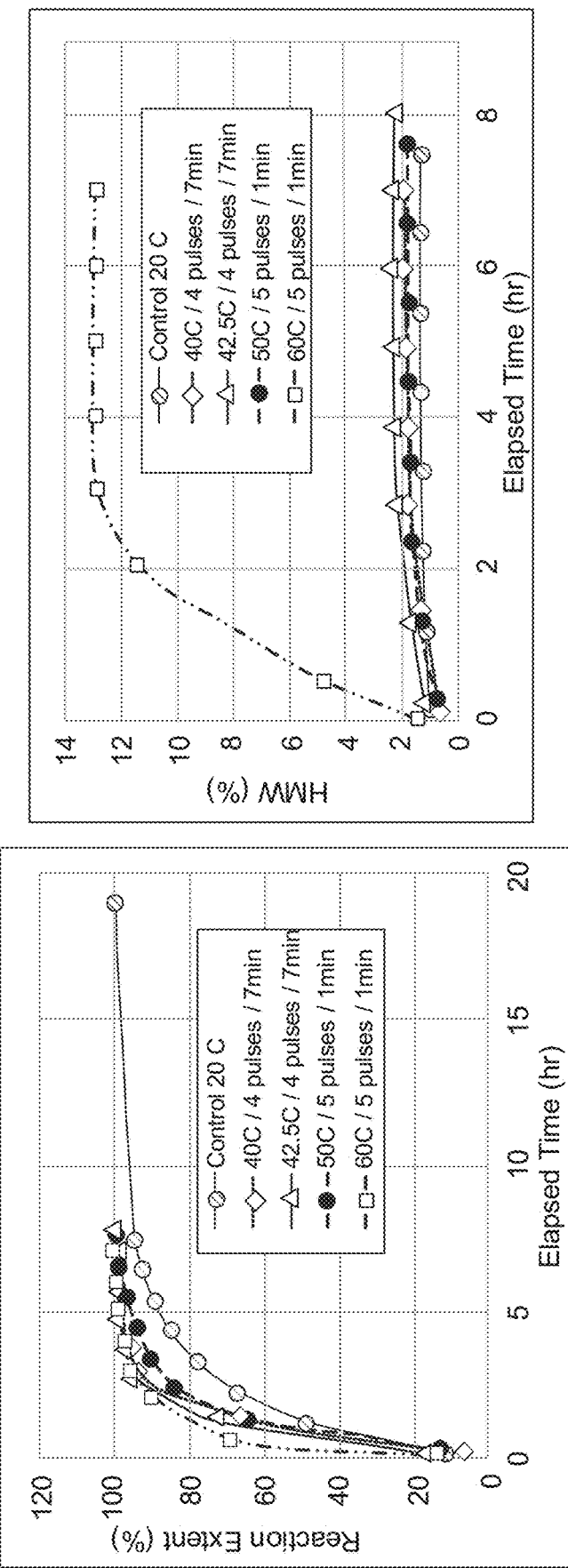

FIG. 14 shows the rate of IMGN853 conjugation (left panel) and the accumulation of high molecular weight (HMW; aggregate) species in conjugation reactions exposed to either a continuous 20° C. temperature or to repeated pulses at higher temperatures.

DETAILED DESCRIPTION OF THE INVENTION

I. Definitions

The terms "antibody drug conjugate" (ADC) and "immunoconjugate" as used herein refer to a compound or a derivative thereof that is linked to a cell binding agent (e.g., an antibody or antigen-binding fragment thereof) and is defined by a generic formula: D-L-A, wherein D=cytotoxic drug, L=linker, and A=antibody or antibody fragment. ADCs can also be defined by the generic formula in reverse order: A-L-D. An ADC can comprise multiple drugs and linkers per antibody or antigen-binding fragment thereof, e.g., $(D-L)_4$-A or A-$(L-D)_2$. The terms "antibody drug conjugate" and "immunoconjugate" are used interchangeably herein.

A "linker" is any chemical moiety that is capable of linking a drug to a cell-binding agent (e.g., antibody or antigen-binding fragment thereof) in a stable, covalent manner. Linkers can be susceptible to or be substantially resistant to acid-induced cleavage, light-induced cleavage, peptidase-induced cleavage, esterase-induced cleavage, and disulfide bond cleavage, at conditions under which the compound or the antibody remains active. Suitable linkers are well known in the art and include, for example, disulfide groups, thioether groups, and peptide linkers.

The term "antibody" means an immunoglobulin molecule that recognizes and specifically binds to a target, such as a protein, polypeptide, peptide, carbohydrate, polynucleotide, lipid, or combinations of the foregoing through at least one antigen recognition site within the variable region of the immunoglobulin molecule. As used herein, the term "antibody" encompasses intact polyclonal antibodies, intact monoclonal antibodies, chimeric antibodies, humanized antibodies, human antibodies, fusion proteins comprising an antibody, and any other modified immunoglobulin molecule so long as the antibodies exhibit the desired biological activity. An antibody can be of any the five major classes of immunoglobulins: IgA, IgD, IgE, IgG, and IgM, or subclasses (isotypes) thereof (e.g. IgG1, IgG2, IgG3, IgG4, IgA1 and IgA2), based on the identity of their heavy-chain constant domains referred to as alpha, delta, epsilon, gamma, and mu, respectively. The different classes of immunoglobulins have different and well known subunit structures and three-dimensional configurations. Antibodies can be naked or conjugated to other molecules such as toxins, radioisotopes, etc.

The term "antibody fragment" refers to a portion of an intact antibody. An "antigen-binding fragment" refers to a portion of an intact antibody that binds to an antigen. An antigen-binding fragment can contain the antigenic determining variable regions of an intact antibody. Examples of antibody fragments include, but are not limited to Fab, Fab', F(ab')2, and Fv fragments, linear antibodies, and single chain antibodies. Antibody fragments can be naked or conjugated to other molecules such as toxins, radioisotopes, etc.

As used herein, the terms "variable region" or "variable domain" are used interchangeably and are common in the art. The variable region typically refers to a portion of an antibody, generally, a portion of a light or heavy chain, typically about the amino-terminal 110 to 120 amino acids or 110 to 125 amino acids in the mature heavy chain and about 90 to 115 amino acids in the mature light chain, which differ extensively in sequence among antibodies and are used in the binding and specificity of a particular antibody for its particular antigen. The variability in sequence is concentrated in those regions called complementarity determining regions (CDRs) while the more highly conserved regions in the variable domain are called framework regions (FR). Without wishing to be bound by any particular mechanism or theory, it is believed that the CDRs of the light and heavy chains are primarily responsible for the interaction and specificity of the antibody with antigen. In certain embodiments, the variable region is a human variable region. In certain embodiments, the variable region comprises rodent or murine CDRs and human framework regions (FRs). In particular embodiments, the variable region is a primate (e.g., non-human primate) variable region. In certain embodiments, the variable region comprises rodent or murine CDRs and primate (e.g., non-human primate) framework regions (FRs).

The terms "VL" and "VL domain" are used interchangeably to refer to the light chain variable region of an antibody.

The terms "VH" and "VH domain" are used interchangeably to refer to the heavy chain variable region of an antibody.

The term "Kabat numbering" and like terms are recognized in the art and refer to a system of numbering amino acid residues in the heavy and light chain variable regions of an antibody or an antigen-binding fragment thereof. In certain aspects, CDRs can be determined according to the Kabat numbering system (see, e.g., Kabat E A & Wu T T (1971) Ann NY Acad Sci 190: 382-391 and Kabat E A et al., (1991) Sequences of Proteins of Immunological Interest, Fifth Edition, U.S. Department of Health and Human Services, NIH Publication No. 91-3242). Using the Kabat numbering system, CDRs within an antibody heavy chain molecule are typically present at amino acid positions 31 to 35, which optionally can include one or two additional amino acids, following 35 (referred to in the Kabat numbering scheme as 35A and 35B) (CDR1), amino acid positions 50 to 65 (CDR2), and amino acid positions 95 to 102 (CDR3). Using the Kabat numbering system, CDRs within an antibody light chain molecule are typically present at amino acid positions 24 to 34 (CDR1), amino acid positions 50 to 56 (CDR2), and amino acid positions 89 to 97 (CDR3). In a specific embodiment, the CDRs of the antibodies described herein have been determined according to the Kabat numbering scheme.

Chothia refers instead to the location of the structural loops (Chothia and Lesk, J. Mol. Biol. 196:901-917 (1987)). The end of the Chothia CDR-H1 loop when numbered using the Kabat numbering convention varies between H32 and H34 depending on the length of the loop (this is because the Kabat numbering scheme places the insertions at H35A and H35B; if neither 35A nor 35B is present, the loop ends at 32; if only 35A is present, the loop ends at 33; if both 35A and 35B are present, the loop ends at 34). The AbM hypervariable regions represent a compromise between the Kabat CDRs and Chothia structural loops, and are used by Oxford Molecular's AbM antibody modeling software.

| Loop | Kabat | AbM | Chothia |
|---|---|---|---|
| L1 | L24-L34 | L24-L34 | L24-L34 |
| L2 | L50-L56 | L50-L56 | L50-L56 |
| L3 | L89-L97 | L89-L97 | L89-L97 |
| H1 | H31-H35B | H26-H35B | H26-H32 . . . 34 |
| | | | (Kabat Numbering) |
| H1 | H31-H35 | H26-H35 | H26-H32 |
| | | | (Chothia Numbering) |
| H2 | H50-H65 | H50-H58 | H52-H56 |
| H3 | H95-H102 | H95-H102 | H95-H102 |

As used herein, the term "constant region" or "constant domain" are interchangeable and have its meaning common in the art. The constant region is an antibody portion, e.g., a carboxyl terminal portion of a light and/or heavy chain which is not directly involved in binding of an antibody to antigen but which can exhibit various effector functions, such as interaction with the Fc receptor. The constant region of an immunoglobulin molecule generally has a more conserved amino acid sequence relative to an immunoglobulin variable domain. In certain aspects, an antibody or antigen-binding fragment comprises a constant region or portion thereof that is sufficient for antibody-dependent cell-mediated cytotoxicity (ADCC).

As used herein, the term "heavy chain" when used in reference to an antibody can refer to any distinct type, e.g., alpha ($\alpha$), delta ($\delta$), epsilon ($\epsilon$), gamma ($\gamma$), and mu ($\mu$), based on the amino acid sequence of the constant domain, which give rise to IgA, IgD, IgE, IgG, and IgM classes of antibodies, respectively, including subclasses of IgG, e.g., $IgG_1$, $IgG_2$, $IgG_3$, and $IgG_4$. Heavy chain amino acid sequences are well known in the art. In specific embodiments, the heavy chain is a human heavy chain.

As used herein, the term "light chain" when used in reference to an antibody can refer to any distinct type, e.g., kappa ($\kappa$) or lambda ($\lambda$) based on the amino acid sequence of the constant domains. Light chain amino acid sequences are well known in the art. In specific embodiments, the light chain is a human light chain.

The term "conjugation process" as used herein refers to a process in which conjugation reaction reagents (e.g., a cell-binding agent, drug, and linker; a cell-binding agent and a drug attached to a linker; or a cell-binding agent attached to a linker and a drug) are mixed under conditions which allow the reagents to react and form ADCs.

The term "batch conjugation process" as used herein refers to a conjugation process in which the conjugation reaction reagents are mixed together in bulk, the conjugation reaction occurs to form conjugation reaction products (ADCs), and the conjugation reaction products (ADCs) are then removed in bulk.

The term "continuous conjugation process" as used herein refers to a conjugation process in which one or more conjugation reaction reagents continue to be added to a conjugation reaction while the conjugation reaction proceeds and after at least one conjugation reaction product (ADC) has formed. The conjugation reaction products (ADCs) can continue to be removed from the conjugation reaction as the conjugation reaction proceeds.

The term "in-situ reaction" as used herein refers to a process in which a drug and linker are mixed to form a drug attached to a linker. The drug attached to the linker can then be used in a conjugation reaction with an cell-binding agent (e.g., an antibody) to form an ADC.

The term "flow reactor" as used herein refers to any reactor vessel, typically tube like, that is used for continuous reaction chemistry. Flow reactors can be made of stainless steel, glass, polymers, etc.

The term "in-line monitoring" as used herein refers to monitoring an analyte in real time, e.g., while a conjugation reaction, concentration process, purification process, or buffer exchange process is occurring.

The term "filter" as used herein refers to a selective barrier that permits the separation of species in a fluid. Separation is achieved by selectively passing (permeating) one or more species of the fluid through the filter while retarding the passage of one or more other species.

The term "feed stream" as used herein refers to a fluid being fed to a filter or membrane for separation of components in the filter or membrane.

The term "retentate" as used herein refers to the portion of the feed stream that does not pass through the filter.

The term "permeate" as used herein refers to the portion of the feed stream that does pass through the filter.

The term "tangential flow filtration" (TFF) as used herein refers to a membrane-based filtration process in which a feed stream passes parallel to a membrane face. One portion of the feed stream passes through the membrane (permeate) while the remainder (retentate) is recirculated back to the feed reservoir. TFF is also referred to as cross-flow filtration. Systems for performing TFF are known and include, for example, a Pellicon-type system (Millipore, Billerica, Mass.), a Sartocon Cassette system (Sartorius AG, Edgewood, N.Y.), and a Centrasette-type system (Pall Corporation, East Hills, N.Y.).

The term "single-pass tangential flow filtration" (SPTFF) as used herein refers to a tangential flow filtration process in which a feedstream passes over the filtration membrane only once. Systems for performing SPTFF are know and include, for example, a Cadance-type system (Pall Corporation, Westborough, Mass.). Systems and methods for performing SPTFF are disclosed, for example, in U.S. Pat. Nos. 7,384,549, 7,510,654, 7,682,511, 7,967,987, 8,157,999, and 8,231,787, each of which is herein incorporated by reference in its entirety.

The term "continuous diafiltration" as used herein refers to a diafiltration process in which selective separation of solutes is achieved in a continuous fashion by mixing a feed stream with a diluent and pumping it across a membrane with the permeate and retentate being removed. The product is not formed in a vessel as filtration progresses; instead it is continuously withdrawn from the system during the course of the filtration. "Countercurrent diafiltration" refers to a continuous diafiltration process in which a process stream (e.g., permeate or retentate) is recycled in diafiltration steps.

The term "in-line monitoring" refers to monitoring an analyte in real-time, e.g., during a production or purification process. In-line monitoring is distinguished from in-process sampling or offline analysis, which do not provide real-time feedback.

The term "in-line process automation technology" refers to any in-line measurement device used to monitor an analyte during a process.

The term "analyte" as used herein is a broad term, and it refers without limitation to a substance or chemical constituent in a fluid that can be analyzed. Analytes may include naturally occurring substances, artificial substances, metabolites, and/or reaction products. In some embodiments, the analyte for measurement in the methods disclosed herein is an antibody or antigen-binding fragment thereof, drug, linker, linker bound to antibody or antigen-binding fragment thereof, linker bound to drug, antibody-drug conjugate (ADC), drug-to-antibody ratio (DAR), and/or impurity.

The term "reaction buffer" as used herein refers to a buffer in which the reaction can take place. Thus, the terms "conjugation reaction buffer" or "conjugation buffer" as used herein refer to a buffer in which a conjugation reaction (a continuous conjugation reaction or a batch conjugation reaction) can take place. Similarly, the terms "in-situ reaction buffer" or "in-situ buffer" as used herein refer a buffer in which an in-situ reaction can take place.

The term "formulation buffer" as used herein refers to a buffer that permits biological activity of the active ingredient and which contains no additional components that are unacceptably toxic to a subject to which the formulation would be administered.

The term "indolinobenzodiazepine" (IGN) as used herein refers to a compound having an indolinobenzodiazepine core structure. The indolinobenzodiazepine can be substituted or unsubstituted. It also includes a compound having two indolinobenzodiazepine core linked by a linker. The imine functionality (—C═N—) as part of indolinobenzodiazepine core can be reduced. In certain embodiments, the indolinobenzodiazepine compound comprises a core structure represented by

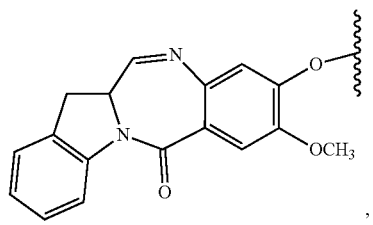 [SMILES: *Oc1cc2c(cc1OC)C(=O)N1c3ccccc3CC1C=N2]

which can be optionally substituted.

In some embodiments, the indolinobenzodiazepine compound comprises a core structure represented by

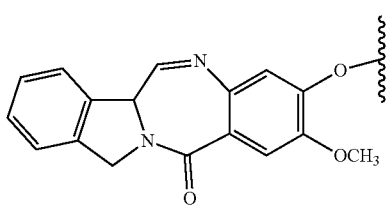

which can be further substituted.

The term "pyrrolobenzodiazepine" (PBD) as used herein refers to a compound having a pyrrolobenzodiazepine core structure. The pyrrolobenzodiazepine can be substituted or unsubstituted. It also includes a compound having two pyrrolobenzodiazepine core linked by a linker. The imine functionality (—C═N—) as part of indolinobenzodiazepine core can be reduced. In certain embodiments, the pyrrolobenzodiazepine compound comprises a core structure represented by

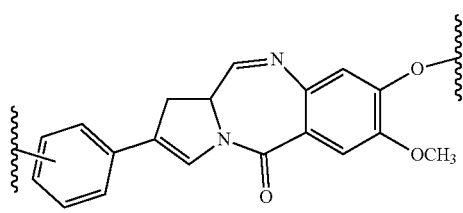

which can be optionally substituted. In certain embodiments, the pyrrolobenzodiazepine compounds comprises a core structure represented by

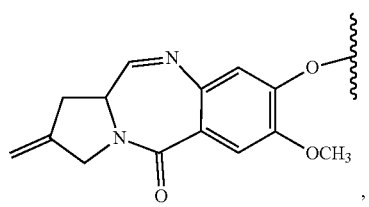 [SMILES: *Oc1cc2c(cc1OC)C(=O)N1CC(=C)CC1C=N2]

which can be optionally substituted.

As used in the present disclosure and claims, the singular forms "a," "an," and "the" include plural forms unless the context clearly dictates otherwise.

It is understood that wherever embodiments are described herein with the language "comprising," otherwise analogous embodiments described in terms of "consisting of" and/or "consisting essentially of" are also provided.

The term "and/or" as used in a phrase such as "A and/or B" herein is intended to include both "A and B," "A or B," "A," and "B." Likewise, the term "and/or" as used in a phrase such as "A, B, and/or C" is intended to encompass each of the following embodiments: A, B, and C; A, B, or C; A or C; A or B; B or C; A and C; A and B; B and C; A (alone); B (alone); and C (alone).

II. Continuous Conjugation, Single-Pass Tangential Flow Filtration, and Countercurrent Diafiltraion Provided herein are continuous methods for forming and/or processing antibody drug conjugates (ADC). In batch formation and processing, components are added to a process, the process proceeds for a period of time, and then the products of the process are removed in bulk. In contrast, in the continuous methods provided herein components continue to be added to an ongoing process, and products can be removed throughout the process instead of in bulk at the end of the process. For example, in a continuous conjugation process, one or more conjugation reaction reagents continue to be added to a conjugation reaction while the reaction proceeds and after at least one conjugation reaction product (ADC) has formed. Similarly, in downstream continuous concentration, purification, and/or buffer exchange processes, ADCs, buffers, and/or other components continue to be added to the concentration purification, and/or buffer exchanges processes as those processes proceed, and concentrated, purified, and buffer exchanged ADCs can be continuously removed from those ongoing processes. Accordingly, an entire ADC process from ADC conjugation to ADC formulation can be continuous (see e.g., FIG. 1 (bottom)).

The present inventors have demonstrated that a conjugation process can be performed continuously using flow reactors. Flow reactors allow one or more conjugation reaction reagents to be continuously added to a conjugation reaction while the conjugation reaction proceeds and after at least one conjugation reaction product (ADC) has formed. The use of flow reactors in the conjugation process allows for control of the conjugation reaction and versatility of the conjugation process (e.g., rapid temperature changes/tighter temperature control, mixing mediated by diffusion therefore more uniform, and no constraints by vessels or suite limitations) and improved scalability of the ADC conjugation process (i.e., the conventional scale-up risks of batch processing do not apply and space-time yield is optimized (e.g., performing a pseudo scale up (increase output) by running the current process for a longer time)).

The present inventors have further demonstrated that continuous ADC processing can be accomplished using single-pass tangential flow filtration (SPTFF), which can successfully separate unconjugated drug from ADCs. Bulk (conventional) diafiltration involves priming a tangential flow filtration (TFF) system with a first buffer A (the buffer that a product is initially in). The product is then added to a retentate vessel where it mixes with the prime volume. A feed pump for the retentate vessel pumps product from the retentate over the TFF membrane, where it is either retained (and returns to the retentate) or discarded to waste. Another pump (the diafiltration pump) would feed from the vessel to buffer B contained in a separate vessel (the buffer into which the product will be exchanged) with a feed line from the vessel into the retentate vessel. Both pumps are started and the product in the retentate vessel begins passing over the TFF membrane. As buffer is removed via the waste stream, the volume in the retentate is maintained by adding Buffer B (in equal volume) to the retentate vessel. As a result, the product slowly is exchanged into Buffer B.

SPTFF uses a related concept of exchanging the product initially in Buffer A into Buffer B. However, the product only ever makes a single-pass over the membrane so all of the appropriate volume of Buffer B to achieve complete buffer exchange must be achieved. To do this, SPTFF can add Buffer B over stacked stages. The product, therefore, passes through the membranes only once: entering in Buffer A and exiting the module in Buffer B.

Similarly, continuous ADC processing can be accomplished using countercurrent diafiltration.

Accordingly, continuous ADC processing methods provided herein (e.g., using SPTFF and/or countercurrent diafiltration) can reduce processing time, improve yield, and/or improve product consistency as compared to batch ADC processing. Continuous ADC processing methods provided herein (e.g., using SPTFF and/or countercurrent diafiltration) can also eliminate hold steps used in batch conjugation processes. Continuous ADC processing methods provided herein (e.g., using SPTFF and/or countercurrent diafiltration) can also allow for use of smaller equipment. SPTFF is also advantageous because antibodies that are sensitive to oxidation, potentially caused by shear forces, may be better suited for SPTFF.

Figure 1:
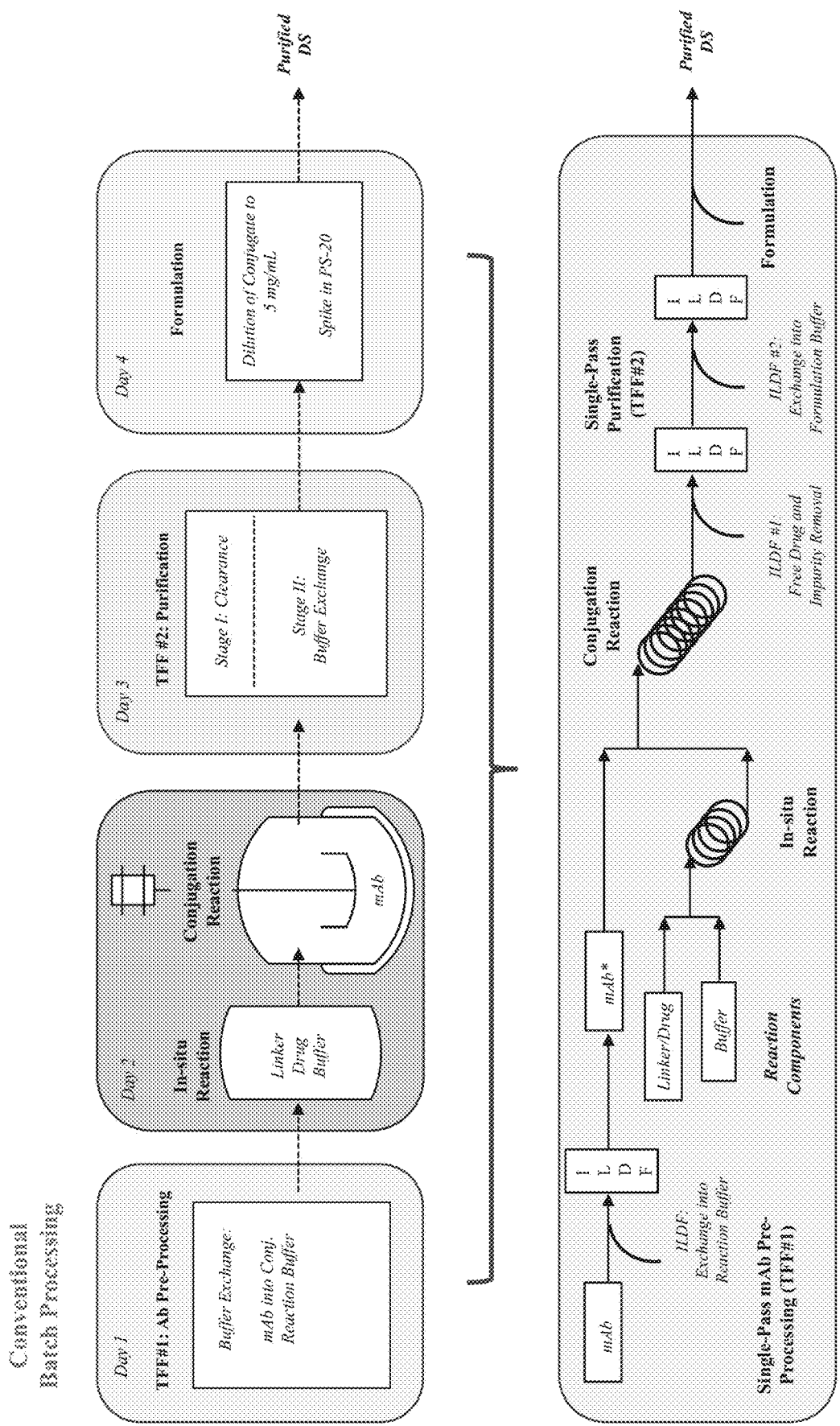
FIG. 1 shows a fully continuous antibody drug conjugate (ADC) manufacturing process with integrated feedback control mechanisms (bottom) and its relation to conventional batch processing (top).
Figure 2:
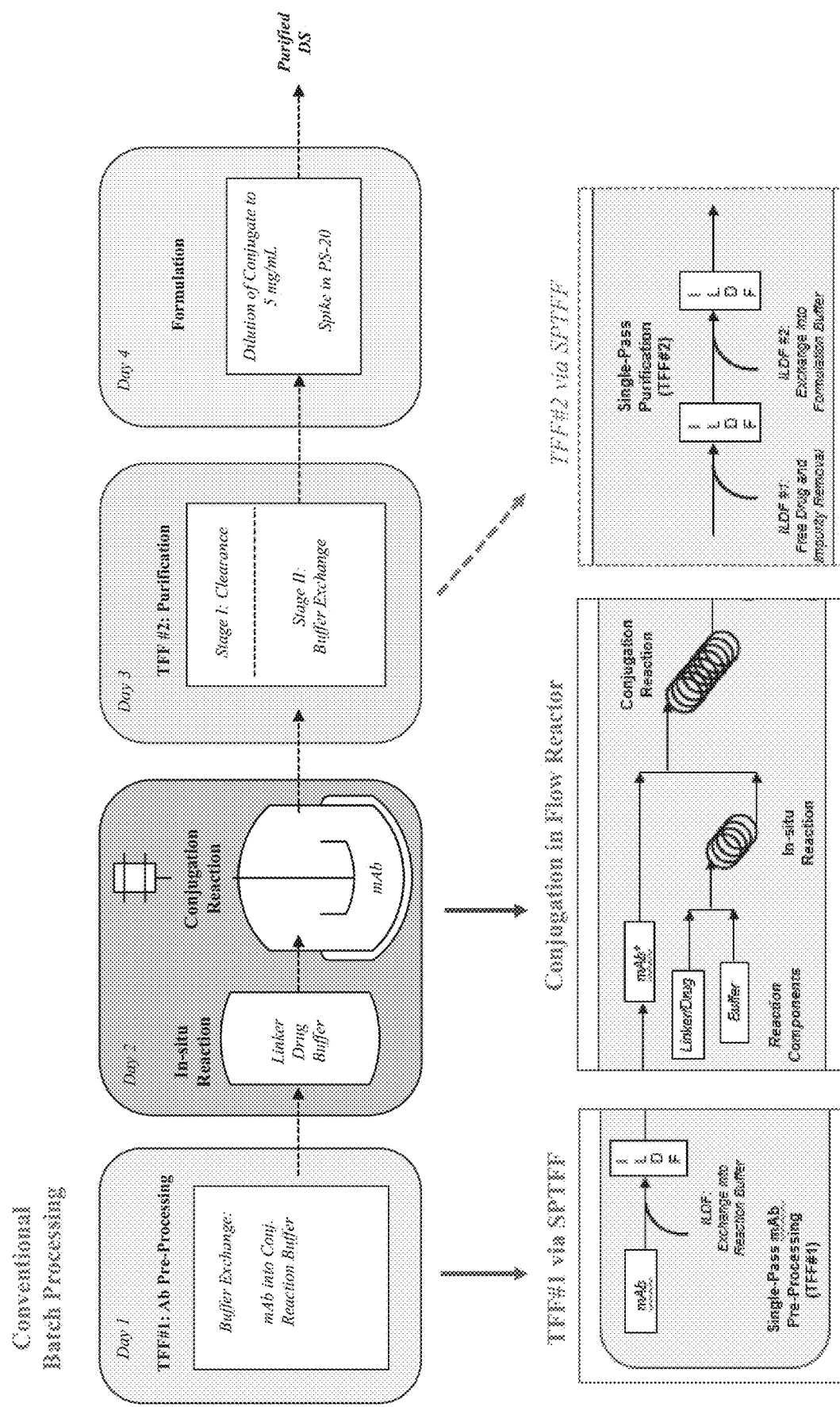
FIG. 2 is a flow diagram showing a semi-batch operation, incorporating continuous-enabling technologies (bottom) and its relation to conventional batch processing (top).
Figure 3:
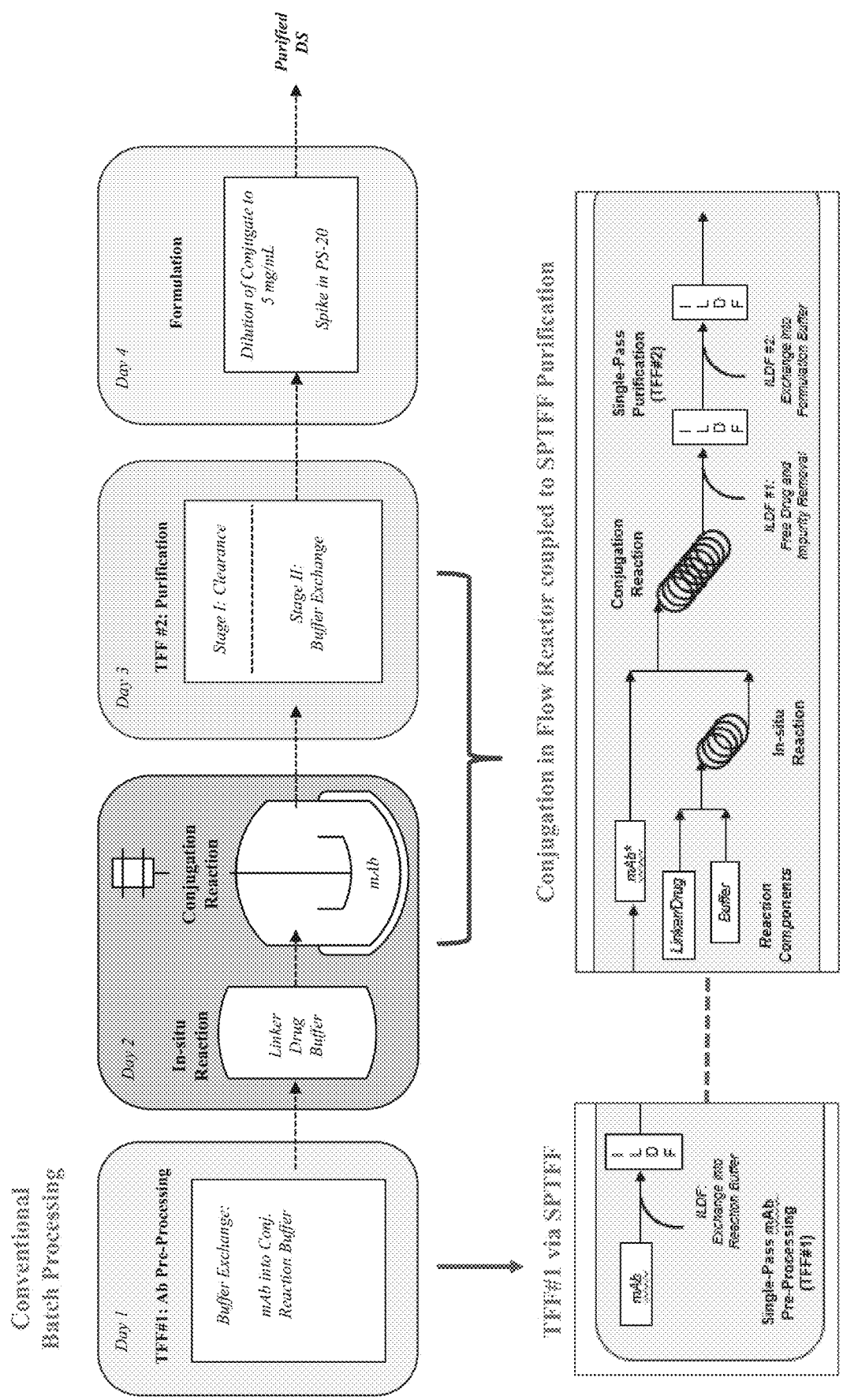
FIG. 3 is a flow diagram showing the coupling of semi-batch unit operations (bottom) and its relation to conventional batch processing (top).

ADC processing can involve conjugation (formation) of the ADC, concentration of the ADC, purification of the ADC, and/or formulation of the ADC. Although it is particularly useful for the entire process from ADC conjugation to formulation to be continuous (e.g., as shown in FIG. 1), it is also possible to combine continuous processing steps with batch processing steps (e.g., as shown in FIGS. 2 and 3). In addition, it is possible for upstream processing steps (e.g., the preparation of an antibody, linker, and/or drug) to be continuous and to feed continuously into the ADC conjugation.

Accordingly, in some methods provided herein the conjugation process for forming antibody drug conjugates (ADCs) is continuous. In a continuous conjugation process one or more conjugation reaction reagents continue to be added to a conjugation reaction while the conjugation reaction proceeds and after at least one conjugation reaction product (ADC) has formed. The conjugation reaction reagents can be put into the system while assembled ADCs are removed from the system. For example, in some continuous conjugation processes provided herein, a cell binding agent (e.g., antibody or antigen-binding fragment thereof), a drug attached to a linker, and a conjugation reaction buffer continue to be added to the conjugation reaction while the conjugation reaction proceeds and after at least one ADC is formed. In some continuous conjugation processes provided herein, a cell binding agent (e.g., antibody or antigen-binding fragment thereof) attached to a linker, a drug, and a conjugation reaction buffer continue to be added to the conjugation reaction while the conjugation reaction proceeds and after at least one ADC is formed. In some continuous conjugation processes provided herein, a cell binding agent (e.g., antibody or antigen-binding fragment thereof), a drug, a linker, and a conjugation reaction buffer continue to be added to the conjugation reaction while the conjugation reaction proceeds and after at least one ADC is formed. The reagents that continue to be added can be added together in a single feed stream or can be fed separately to a collection vessel or directly into a reaction vessel.

In some continuous conjugation processes provided herein, only one of a cell binding agent (e.g., an antibody or antigen-binding fragment thereof), a cell binding agent attached to a linker, a drug, a drug attached to a linker, a linker, or a conjugation reaction buffer continues to be added to the conjugation reaction while the conjugation reaction proceeds and after at least one ADC is formed. In some continuous conjugation processes provided herein, two reagents selected from the group consisting of: a cell binding agent (e.g., an antibody or antigen-binding fragment thereof), a cell binding agent attached to a linker, a drug, a drug attached to a linker, a linker, and a conjugation reaction buffer continue to be added to the conjugation reaction while the conjugation reaction proceeds and after at least one ADC is formed.

The use of SPTFF can allow for continuous addition and/or removal of components from the conjugation reaction. Thus, SPTFF can be used to prepare reagents for ADC conjugation and for processing assembled ADCs. SPTFF can enable continuous ADC processing so that all (or a subset) of the processing steps for a particular ADC (e.g., production, concentration, purification, and/or formulation) can be occur simultaneously. Countercurrent diafilatration can also be used to prepare reagents for ADC conjugation and for processing assembled ADCs.

According to the methods provided herein, SPTFF can be used to concentrate an ADC, to purify an ADC, and/or to formulate an ADC (e.g., by exchanging an ADC into a formulation buffer). SPTFF can be used to transfer an ADC from a first buffer to a second buffer. Countercurrent diafiltration can also be used to concentrate an ADC, to purify an ADC, and/or to formulate an ADC (e.g., by exchanging an ADC into a formulation buffer), and countercurrent diafiltration can also be used to transfer an ADC from a first buffer to a second buffer.

In some methods provided herein, SPTFF is used throughout ADC production, purification, and formulation, making the entire process from ADC production to formulation continuous. In some methods provided herein, countercurrent diafiltration is used throughout ADC production, purification, and formulation, making the entire process from ADC production to formulation continuous. Thus, the entire processes shown in exemplary FIGS. 4 and 10 can be continuous.

Figure 4:
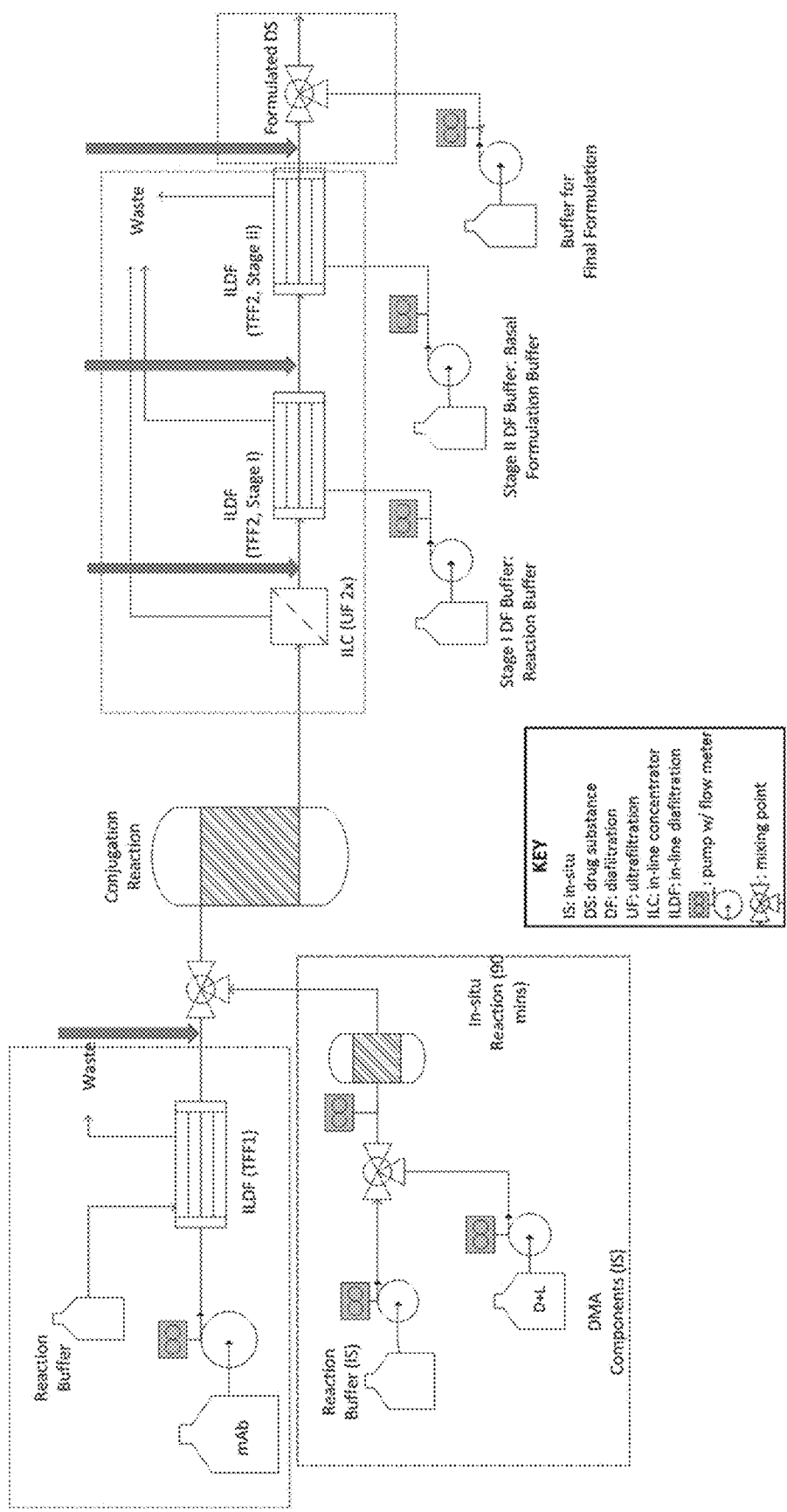
FIG. 4 is a flow diagram showing the continuous conjugation process for the conjugation of the antibody drug conjugate ADC "IMGN853" described in Example 1. "mAb" refers to monoclonal antibody (i.e., huMov19). "D" refers to drug (i.e., the maytansinoid DM4), and "L" refers to linker (i.e., sSPDB.)

In some methods provided herein, SPTFF is used in combination with conventional TFF such that some portions of the processes shown in exemplary FIGS. 4 and 10 are continuous, whereas other portions are performed in batches. For example, an antibody or antigen-binding fragment thereof can be buffer-exchanged prior to conjugation using conventional (batch) TFF (see e.g., TFF1 in FIG. 4)

and then fed into a continuous process, wherein SPTFF is used for downstream processes (see e.g., TFF2 Stage I and II in FIG. 4). Countercurrent diafiltration can be used in place of or in combination with SPTFF in such methods.

In FIGS. 4 and 10, each of the boxes shown in doted lines represents an individual portion of the process that can be conducted in either a batch or a continuous manner. For example, the process for putting an antibody in buffer for conjugation shown in the upper left hand box of FIG. 4 can use SPTFF and be performed in a continuous fashion or can use conventional TFF and be performed in a batch fashion. Regardless of whether the process for putting an antibody in buffer for conjugation is performed in a batch or continuous fashion, the ADC concentration and purification processes shown in the box downstream of the conjugation reaction can be use SPTFF and be performed in a continuous fashion or can use conventional TFF and be performed in a batch fashion. Similarly, regardless of whether the process for putting an antibody in buffer for conjugation is performed in a batch or continuous process, and regardless of whether the ADC is concentrated and purified using a batch or continuous process, the ADC can be formulated using SPTFF in a continuous fashion or using conventional TFF in a batch fashion. Ccountercurrent diafiltration can be used in place of or in combination with SPTFF in such methods.

In some embodiments, at least two steps in an ADC process are performed using SPTFF. For example, in some embodiments, SPTFF is used to transfer an antibody or antigen-binding fragment thereof into a conjugation buffer and used to concentrate and purify the ADC after it is formed, while either SPTFF or TFF is used to exchange the ADC into formulation buffer. In some embodiments, SPTFF is used to transfer an antibody or antigen-binding fragment thereof into a conjugation buffer and used to exchange a purified ADC into formulation buffer, while either SPTFF or TFF is used to concentrate and purify the ADC after it is formed. In some embodiments, SPTFF is used to concentrate and purify the ADC and used to exchange the concentrated and purified ADC into formulation buffer, wherein either SPTFF or TFF is used to transfer the antibody or antigen-binding fragment thereof into a conjugation buffer.

SPTFF can use an ultrafiltration membrane, e.g., in methods of concentrating an ADC. SPTFF can use a diafiltration membrane, e.g., in methods of purifying an ADC and/or in methods of transferring an ADC to a buffer (e.g., a formulation buffer).

In some embodiments, at least two steps in an ADC process are performed using SPTFF and/or countercurrent diafiltration. For example, in some embodiments, SPTFF and/or countercurrent diafiltration is used to transfer an antibody or antigen-binding fragment thereof into a conjugation buffer and used to concentrate and purify the ADC after it is formed, while SPTFF, countercurrent diafiltration, and/or TFF is used to exchange the ADC into formulation buffer. In some embodiments, SPTFF and/or countercurrent diafiltration is used to transfer an antibody or antigen-binding fragment thereof into a conjugation buffer and used to exchange a purified ADC into formulation buffer, while SPTFF, countercurrent diafiltration, and/or TFF is used to concentrate and purify the ADC after it is formed. In some embodiments, SPTFF and/or countercurrent diafiltration is used to concentrate and purify the ADC and used to exchange the concentrated and purified ADC into formulation buffer, wherein SPTFF, countercurrent diafiltration, and/or TFF is used to transfer the antibody or antigen-binding fragment thereof into a conjugation buffer.

Column chromatography can also be used in a flow-through mode in the continuous ADC processing methods provided herein (e.g., in combination with SPTFF and/or countercurrent diafiltration). For example, a conjugation reaction (e.g., a continuous conjugation reaction) can feed into flow-through column chromatography to remove unconjugated drug from a conjugation reaction (similar to the role of the TFF2, Stage ILDF step in FIG. 4). The ADCs purified via the flow-through column chromatography can then feed into an SPTFF process for buffer exchange into a formulation buffer (e.g., the TFF2, Stage II ILDF step in FIG. 5.) The ADCs purified via the flow-through column chromatography can also feed into a countercurrent diafiltration process for buffer exchange into a formulation buffer.

In some instances, the reaction parameters of the continuous flow conjugation processes provided herein can be rapidly changed or "pulsed". For example, in a continuous flow conjugation, temperature can be rapidly altered, e.g., by using a water bath, encapsulated reactor, heater, thermoelectric source, and/or insulating a section of coils and/or tubes through which the reaction flows. In addition, in a continuous flow conjugation, pH can be rapidly altered, e.g., by addition of an acid or base. Accordingly, in certain instances, a conjugation reaction is performed using a pulsed parameter. The use of a pulsed parameter can, for example, decrease reaction time (i.e., increase reaction speed), without compromising product quality, quench or stop a reaction temporarily by rapidly dropping the temperature, stabilize the conjugate in solution before another perturbation (e.g., addition of another chemical reagent) is introduced, whereas longer exposures to the same parameter can dramatically decrease product quality or product stability.

In certain instances, the conjugation reaction is exposed to an altered temperature (e.g., increased or decreased) for a specified time increment for a specified number of times. For example, in one instance, temperature is increased by at least 2° C., at least 3° C., at least 4° C., or at least 5° C. Accordingly, the temperature can be increased or decreased by at least 5° C., 10° C., 15° C., 20° C., 25° C., 30° C., or 35° C. For instance, the temperature can be increased or decreased by 5° C., 10° C., 15° C., 20° C., 25° C., 30° C., or 35° C. The temperature can also be increased or decreased by about 5° C. to about 10° C., by about 10° C. to about 15° C., by about 15° C. to about 20° C., by about 20° C. to about 25° C., by about 25° C. to about 30° C., or by about 30° C. to about 35° C. Thus, for example, temperature can be increased (e.g., from about 20° C.) to an elevated temperature of 25° C., 30° C., 35° C., 40° C., 45° C., 50° C., or 55° C. Temperature can be also increased (e.g., from about 25° C.) to an elevated temperature of 30° C., 35° C., 40° C., 45° C., 50° C., or 55° C. In certain instances, the temperature does not exceed 55° C. In certain instance, the temperature is increased (e.g., from about 20° C.) to an elevated temperature in the range of about 35° C. to about 55° C. or to an elevated temperature in the range of about 40° C. to about 50° C. In certain instances, the temperature is increased (e.g., from about 20° C.) to an elevated temperature of about 60° C., to about 70° C., to about 80° C., to about 90° C., or to about 100° C. (e.g., for a short time increment such as 10 seconds). In certain instances, the temperature is increased (e.g., from about 20° C.) to an elevated temperature in the range of 60° C. to 70° C., in the range of 70° C. to 80° C., in the range of 80° C. to 90° C., or in the range of 90° C. to 100° C. (e.g., for a short time increment such as 10 seconds). In certain instances, the time it takes to increase or decrease the temperature to the elevated or reduced temperature is no more than 2 minutes. In certain instances, the time it takes to increase or decrease the temperature to the elevated or reduced temperature is no more than 1 minute.

In certain instances, the conjugation reaction is exposed to an altered pH (e.g., increased or decreased) for a specified time increment for a specified number of times. For example, in one instance, pH is increased or decreased by about 1, about 2, about 3, about 4, or about 5. In one instance, pH is increased by about 1 to about 2, by about 2 to about 3, by about 3 to about 4, or by about 4 to about 5. Thus, for example, pH can be increased (e.g., from about 4) to about 5, about 6, about 7, about 8, or about 9. PH can also be increased (e.g., from about 5) to about 6, about 7, about 8, or about 9. PH can also be decreased (e.g., from about 9) to about 8, about 7, about 6, about 5, or about 4.

In certain instances, the pulse (e.g., exposure to altered temperature and/or pH) occurs for about 30 seconds, about 1 minute, about 2 minutes, about 3 minutes, about 4 minutes, about 5 minutes, about 6 minutes, about 7 minutes, about 8 minutes, about 9 minutes, about 10 minutes, about 15 minutes, about 30 minutes, about an hour, about 1.5 hours, or about 2 hours. The pulse (e.g., exposure to altered temperature and/or) can also occur, for example, for about 30 seconds to about 1 minute, for about 1 minute to about 2 minutes, for about 2 minutes to about 3 minutes, for about 3 minutes to about 4 minutes, for about 4 minutes to about 5 minutes, for about 6 minutes to about 7 minutes, for about 7 minutes to about 8 minutes, for about 8 minutes to about 9 minutes, or for about 9 minutes to about 10 minutes. The pulse (e.g., exposure to altered temperature and/or) can also occur, for example, for about 1 to 10 minutes, for about 1 to 15 minutes, for about 1 to 30 minutes, for about 1 minute to 1 hour, for about 1 minute to about 1.5 hours, or for about 1 minute to about 2 hours. The pulse (e.g., exposure to altered temperature and/or) can also occur, for example, for about 1 to 5 minutes, or about 5 to 10 minutes, about 10 to about 15 minutes, about 15 minutes to about 30 minutes, about 30 minutes to about 1 hour, about 1 hour to about 1.5 hours, or about 1.5 hours to about 2 hours. In certain instances, the pulse (e.g., exposure to altered temperature and/or pH) does not exceed 2 hours, 1 hour, 30 minutes, 20 minutes, or 15 minutes.

In certain instances, the pulse (e.g., exposure to altered temperature and/or pH) occurs once. In certain instances, the pulse (e.g., exposure to altered temperature and/or) is repeated twice, three times, four times, five times, six times, seven times, eight times, nine times, or ten times. In certain instances, the pulse (e.g., exposure to altered temperature and/or) occurs one to five times. In certain instances, the pulse (e.g., exposure to altered temperature and/or) occurs two to twenty times or five to ten times.

Continuous ADC processing methods (e.g., using SPTFF and/or countercurrent diafiltration) can be used with or without in-line monitoring processes (discussed below).

III. In-Line Process Automation Technology (in-Line PAT)

Provided herein are in-line process automation technologies used for forming and processing antibody drug conjugates (ADCs). Such technologies provide for direct measurements, which can eliminate off-line assays and decrease handling of materials by operators. In-line monitoring can be used to monitor ADC (protein) concentration as well as the removal of free drug. This can allow targeting a final ADC concentration based on data obtained from in-line readings instead of based on a specific volume or number of diavolumes used in the processes (e.g., purification processes). PAT implementation allows for increase control and detectability (e.g., changes during steady-state operation can be used to detect issues before product quality is impacted) and use of multiple PAT modules (e.g., FlowVPE, UV sensors, pH meter, conductivity meter, pressure sensors, or flow meters) can ensure robust process performance across individual unit operations.

In-line monitoring can be used, for example, to monitor the flow rates in a feed stream from any pump in, for example, an in-situ reaction and/or an ADC conjugation reaction (e.g., a continuous conjugation reaction or a batch conjugation reaction). In-line monitoring can be used, for example, to monitor the concentration of a component added to an in-situ reaction and/or an ADC conjugation reaction (e.g., a continuous conjugation reaction or a batch conjugation reaction). Such monitoring can ensure adequate control over the stoichiometry of the reactions. The in-line monitoring can monitor the flow rate or concentration of, for example, an antibody or antigen-binding fragment thereof, a drug, a linker, drug attached to a linker, an antibody or antigen-binding fragment thereof attached to a linker, and/or a conjugation buffer. The in-line monitoring can monitor the flow rate of concentration of an antibody or antigen-binding fragment thereof into a conjugation reaction buffer.

In-line monitoring can also be used, for example, to determine when to stop a conjugation reaction, e.g., by stopping to add conjugation buffer, by stopping the circulation of conjugation buffer, and/or starting to rinse or remove conjugation buffer. In some embodiments provided herein, in-line monitoring of an unconjugated drug or an unconjugated drug attached to a linker can be used. Measurements of unconjugated drug or unconjugated drug attached to a linker can be used to infer the average number of drugs per antibody (DAR) achieved in a conjugation reaction. Thus, a conjugation reaction can be stopped when the targeted DAR is reached.

In-line monitoring can also be used to monitor the concentration and/or purification of an ADC. For example, in-line monitoring can be used before or after the ILC and/or TFF2 ILDF processes shown in exemplary FIG. 4 or before or after the ILC or TFF3 ILDF processes shown in exemplary FIG. 10. The concentration and/or purification can use filtration (e.g., ultrafiltration, difiltration). The filtration can be tangential flow filtration, including single-pass tangential flow filtration (SPTFF). The filtration can be countercurrent diafiltration. When used to monitor filtration, in-line monitoring can be used to measure an analyte in either the retentate or the permeate. Thus, for example, in-line monitoring of an unconjugated drug or unconjugated drug attached to linker in a retentate can be used to assess the degree of purification of the ADC. Levels of unconjugated drug or unconjugated drug attached to a linker can be high in a retentate shortly after a conjugation reaction but low in a retentate after purification (see e.g., FIG. 12). In-line monitoring of an ADC in a retentate or a permeate can be used to assess ADC loss during concentration and/or purification processes (see e.g., FIG. 12).

The purification can also use chromatography (e.g., flow through column chromatography). In-line monitoring at the end of a chromatography column can, for example, measure ADC levels and can be used to determine when a column is overloaded or when there is ADC breakthrough.

In-line monitoring can also be used to measure pH, which can be used, for example, to determine the completeness of a buffer exchange (see e.g., FIG. 12).

Exemplary in-line monitoring technologies include the use of, for example, a Fourier Transform Infared (FTIR)

flow cell, High Performance Liquid Chromatography (HPLC), or Ultra Performance Liquid Chromatography (UPLC).

In-line monitoring technologies can use, for example, a FlowVPE or UV sensor. In some embodiments, FlowVPE is used to perform in-line monitoring. FlowVPE uses a flow cell for continuous monitoring.

The efficacy of tangential flow filtration (e.g., single-pass tangential flow filtration (SPTFF) can be monitored in-line using FlowVPE, a UV sensor, a pH meter, a conductivity meter, a pressure sensor, a flow meter, etc. The efficacy of countercurrent diafiltration can also be monitored in-line using FlowVPE, a UV sensor, a pH meter, a conductivity meter, a pressure sensor, a flow meter, etc.

In-line monitoring processes can be used in combination with continuous conjugation processes (discussed above), e.g., using single-pass tangential flow filtration and/or countercurrent diafiltration, or with batch conjugation processes (which are known in the art).

IV. Antibody Drug Conjugates (ADCs)

As provided herein, antibody drug conjugates (ADCs) can comprise a cell-binding agent, a linker, and a drug.

The cell-binding agent can be an antibody or antigen-binding fragment thereof, e.g., a monoclonal antibody or antigen-binding fragment thereof. The cell-binding agent (e.g., antibody or antigen-binding fragment thereof) can be humanized. The cell-binding agent (e.g., antibody or antigen-binding fragment thereof) can be human.

The cell-binding agent (e.g., antibody or antigen-binding fragment thereof) can specifically bind to human CD37, CD33, FOLR1, CD123, CD19, cMET, ADAMS, or HER2.

The cell-binding agent (e.g., antibody or antigen-binding fragment thereof) can comprise the six CDRs of an antibody provided in Table 1.

TABLE 1

Antibody Complementarity Determining Region Sequences

| Name | CDR Sequence |
|---|---|
| huMov19 VH CDR1 | GYFMN (SEQ ID NO: 1) |
| huMov19 VH CDR2 | RIHPYDGDTFYNQKFQG (SEQ ID NO: 2) |
| huMov19 VH CDR3 | YDGSRAMDY (SEQ ID NO: 3) |
| huMov19 VL CDR1 | KASQSVSFAGTSLMH (SEQ ID NO: 4) |
| huMov19 VL CDR2 | RASNLEA (SEQ ID NO: 5) |
| huMov19 VL CDR3 | QQSREYPYT (SEQ ID NO: 6) |
| Z4681A VH CDR1 | SYYIH (SEQ ID NO: 7) |
| Z4681A VH CDR2 | VIYPGNDDISYNQKFQG (SEQ ID NO: 8) |
| Z4681A VH CDR3 | EVRLRYFDV (SEQ ID NO: 9) |
| Z4681A VL CDR1 | KSSQSVFFSSSQKNYLA (SEQ ID NO: 10) |
| Z4681A VL CDR2 | WASTRES (SEQ ID NO: 11) |
| Z4681A VL CDR3 | HQYLSSRT (SEQ ID NO: 12) |
| G4723A VH CDR1 | SSIMH (SEQ ID NO: 13) |
| G4723A VH CDR2 | YIKPYNDGTKYNEKFKG (SEQ ID NO: 14) |
| G4723A VH CDR3 | EGGNDYYDTMDY (SEQ ID NO: 15) |

TABLE 1-continued

Antibody Complementarity Determining Region Sequences

| Name | CDR Sequence |
|---|---|
| G4723A VL CDR1 | RASQDINSYLS (SEQ ID NO: 16) |
| G4723A VL CDR2 | RVNRLVD (SEQ ID NO: 17) |
| G4723A VL CDR3 | LQYDAFPYT (SEQ ID NO: 18) |
| huCMET-27 VH CDR1 | SYDMS (SEQ ID NO: 19) |
| huCMET-27 VH CDR2 | TINSNGVSIYYPDSVKG (SEQ ID NO: 20) |
| huCMET-27 VH CDR3 | EEITTEMDY (SEQ ID NO: 21) |
| huCMET-27 VL CDR1 | RASESVDSYGNSFIH (SEQ ID NO: 22) |
| huCMET-27 VL CDR2 | RASNLES (SEQ ID NO: 23) |
| huCMET-27 VL CDR3 | QQSNEEPLT (SEQ ID NO: 24) |
| huB4 VH CDR1 | SNWMH (SEQ ID NO: 25) |
| huB4 VH CDR2 | EIDPSDSYTN (SEQ ID NO: 26) |
| huB4 VH CDR3 | GSNPYYYAMDY (SEQ ID NO: 27) |
| huB4 VL CDR1 | SASSGVNYMH (SEQ ID NO: 28) |
| huB4 VL CDR2 | DTSKLAS (SEQ ID NO: 29) |
| huB4 VL CDR3 | HQRGSYT (SEQ ID NO: 30) |
| huADAM9 VH CDR1 | SYWMH (SEQ ID NO: 31) |
| huADAM9 VH CDR2 | EIIPIFGHTNYNEKFKS (SEQ ID NO: 32) |
| huADAM9 VH CDR3 | GGYYYYFNSGTLDY (SEQ ID NO: 33) |
| huADAM9 VL CDR1 | KASQSVDYSGDSYMN (SEQ ID NO: 34) |
| huADAM9 VL CDR2 | AASDLES (SEQ ID NO: 35) |
| huADAM9 VL CDR3 | QQSHEDPFT (SEQ ID NO: 36) |

The cell-binding agent (e.g., antibody or antigen-binding fragment thereof) can comprise the variable heavy chain and/or variable light chain of an antibody provided in Table 2. In some embodiments, the cell-binding agent (e.g., antibody or antigen-binding fragment thereof) comprises the CDRs of (e.g., the Kabat-defined, AbM-defined, or Chothia-defined CDRs) a variable heavy and variable light chain of an antibody provided in Table 2.

TABLE 2

Antibody Variable Heavy and Variable Light Sequences

| Name | Variable Heavy or Variable Light Sequence |
|---|---|
| huMov19 VH | QVQLVQSGAEVVKPGASVKISCKASGYTFTGYFMN WVKQSPGQSLEWIGRIHPYDGDTFYNQKFQGKATL TVDKSSNTAHMELLSLTSEDFAVYYCTRYDGSRAM DYWGQGTTVTVSS (SEQ ID NO: 37) |
| huMov19 VL version 1.00 | DIVLTQSPLSLAVSLGQPAIISCKASQSVSFAGTS LMHWYHQKPGQQPRLLIYRASNLEAGVPDRFSGSG SKTDFTLNISPVEAEDAATYYCQQSREYPYTFGGG TKLEIKR (SEQ ID NO: 38) |

TABLE 2-continued

Antibody Variable Heavy and Variable Light Sequences

| Name | Variable Heavy or Variable Light Sequence |
|---|---|
| huMov19 VL version 1.60 | DIVLTQSPLSLAVSLGQPAIISCKASQSVSFAGTS LMHWYHQKPGQQPRLLIYRASNLEAGVPDRFSGSG SKTDFTLTISPVEAEDAATYYCQQSREYPYTFGGG TKLEIKR (SEQ ID NO: 39) |
| Z4681A VH | QVQLQQPGAEVVKPGASVKMSCKASGYTFTSYYIH WIKQTPGQGLEWVGVIYPGNDDISYNQKFQGKATL TADKSSTTAYMQLSSLTSEDSAVYYCAREVRLRYF DVWGQGTTVTVSS (SEQ ID NO: 40) |
| Z4681A VL | EIVLTQSPGSLAVSPGERVTMSCKSSQSVFFSSSQ KNYLAWYQQIPGQSPRLLIYWASTRESGVPDRFTG SGSGTDFTLTISSVQPEDLAIYYCHQYLSSRTFGQ GTKLEIKR (SEQ ID NO: 41) |
| G4723A VH | QVQLVQSGAEVKKPGASVKVSCKASGYIFTSSIMH WVRQAPGQGLEWIGYIKPYNDGTKYNEKFKGRATL TSDRSTSTAYMELSSLRSEDTAVYYCAREGGNDYY DTMDYWGQGTLVTVSS (SEQ ID NO: 42) |
| G4723A VL | DIQMTQSPSSLSASVGDRVTITCRASQDINSYLSW FQQKPGKAPKTLIYRVNRLVDGVPSRFSGSGSGND YTLTISSLQPEDFATYYCLQYDAFPYTFGQGTKVE IKR (SEQ ID NO: 43) |
| huCMET-27 VH | EVQLVESGGGLVQPGGSLRLSCAASGFTFSSYDMS WVRQAPGKGLEWVATINSNGVSIYYPDSVKGRFTI SRDNAKNSLYLQMNSLRAEDTAVYYCAREEITTEM DYWGQGTLVTVSS (SEQ ID NO: 44) |
| huCMET-27 VL | EIVLTQSPATLSLSPGERATLSCRASESVDSYGNS FIHWYQQKPGQAPRLLIYRASNLESGIPARFSGSG SGTDFTLTISSLEPEDFAVYYCQQSNEEPLTFGQG TKVELKR (SEQ ID NO: 45) |
| huB4 VH | QVQLVQPGAEVVKPGASVKLSCKTSGYTFTSNWMH WVKQAPGQGLEWIGEIDPSDSYTNYNQNFQGKAKL TVDKSTSTAYMEVSSLRSDDTAVYYCARGSNPYYY AMDYWGQGTSVTVSS (SEQ ID NO: 46) |
| huB4 VL | EIVLTQSPAIMSASPGERVTMTCSASSGVNYMHWY QQKPGTSPRRWIYDTSKLASGVPARFSGSGSGTDY SLTISSMEPEDAATYYCHQRGSYTFGGGTKLEIKR (SEQ ID NO: 47) |
| huADAM9 VH | EVQLVESGGGLVKPGGSLRLSCAASGFTFSSYWMH WVRQAPGKGLEWVGEIIPIFGHTNYNEKFKSRFTI SLDNSKNTLYLQMGSLRAEDTAVYYCARGGYYYYF NSGTLDYWGQGTTVTVSS (SEQ ID NO: 48) |
| huADAM9 VL | DIVMTQSPDSLAVSLGERATISCKASQSVDYSGDS YMNWYQQKPGQPPKLLIYAASDLESGIPARFSGSG SGTDFTLTISSLEPEDFATYYCQQSHEDPFTFGQG TKLEIK (SEQ ID NO: 49) |

The cell-binding agent (e.g., antibody or antigen-binding fragment thereof) can comprise the heavy chain and/or light chain of an antibody provided in Table 3.

TABLE 3

Antibody Heavy and Light Sequences

| Name | Heavy or Light Sequence |
|---|---|
| huMov19 Heavy | QVQLVQSGAEVVKPGASVKISCKASGYTFTGYFMN WVKQSPGQSLEWIGRIHPYDGDTFYNQKFQGKATL TVDKSSNTAHMELLSLTSEDFAVYYCTRYDGSRAM DYWGQGTTVTVSSASTKGPSVFPLAPSSKSTSGGT AALGCLVKDYFPEPVTVSWNSGALTSGVHTFPAVL QSSGLYSLSSVVTVPSSSLGTQTYICNVNHKPSNT KVDKKVEPKSCDKTHTCPPCPAPELLGGPSVFLFP PKPKDTLMISRTPEVTCVVVDVSHEDPEVKFNWYV DGVEVHNAKTKPREEQYNSTYRVVSVLTVLHQDWL NGKEYKCKVSNKALPAPIEKTISKAKGQPREPQVY TLPPSRDELTKNQVSLTCLVKGFYPSDIAVEWESN GQPENNYKTTPPVLDSDGSFFLYSKLTVDKSRWQQ GNVFSCSVMHEALHNHYTQKSLSLSPG (SEQ ID NO: 50) |
| huMov19 Light 1.00 | DIVLTQSPLSLAVSLGQPAIISCKASQSVSFAGTS LMHWYHQKPGQQPRLLIYRASNLEAGVPDRFSGSG SKTDFTLNISPVEAEDAATYYCQQSREYPYTFGGG TKLEIKRTVAAPSVFIFPPSDEQLKSGTASVVCLL NNFYPREAKVQWKVDNALQSGNSQESVTEQDSKDS TYSLSSTLTLSKADYEKHKVYACEVTHQGLSSPVT KSFNRGEC (SEQ ID NO: 51) |
| huMov19 Light 1.60 | DIVLTQSPLSLAVSLGQPAIISCKASQSVSFAGTS LMHWYHQKPGQQPRLLIYRASNLEAGVPDRFSGSG SKTDFTLTISPVEAEDAATYYCQQSREYPYTFGGG TKLEIKRTVAAPSVFIFPPSDEQLKSGTASVVCLL NNFYPREAKVQWKVDNALQSGNSQESVTEQDSKDS TYSLSSTLTLSKADYEKHKVYACEVTHQGLSSPVT KSFNRGEC (SEQ ID NO: 52) |
| Z4681A Heavy | QVQLQQPGAEVVKPGASVKMSCKASGYTFTSYYIH WIKQTPGQGLEWVGVIYPGNDDISYNQKFQGKATL TADKSSTTAYMQLSSLTSEDSAVYYCAREVRLRYF DVWGQGTTVTVSSASTKGPSVFPLAPSSKSTSGGT AALGCLVKDYFPEPVTVSWNSGALTSGVHTFPAVL QSSGLYSLSSVVTVPSSSLGTQTYICNVNHKPSNT KVDKKVEPKSCDKTHTCPPCPAPELLGGPSVFLFP PKPKDTLMISRTPEVTCVVVDVSHEDPEVKFNWYV DGVEVHNAKTKPREEQYNSTYRVVSVLTVLHQDWL NGKEYKCKVSNKALPAPIEKTISKAKGQPREPQVY TLPPSRDELTKNQVSLTCLVKGFYPSDIAVEWESN GQPENNYKTTPPVLDSDGSFFLYSKLTVDKSRWQQ GNVFSCSVMHEALHNHYTQKSLSLSPG (SEQ ID NO: 53) |
| Z4681A Light | EIVLTQSPGSLAVSPGERVTMSCKSSQSVFFSSSQ KNYLAWYQQIPGQSPRLLIYWASTRESGVPDRFTG SGSGTDFTLTISSVQPEDLAIYYCHQYLSSRTFGQ GTKLEIKRTVAAPSVFIFPPSDEQLKSGTASVVCL LNNFYPREAKVQWKVDNALQSGNSQESVTEQDSKD STYSLSSTLTLSKADYEKHKVYACEVTHQGLSSPV TKSFNRGEC (SEQ ID NO: 54) |
| G4723A Heavy | QVQLVQSGAEVKKPGASVKVSCKASGYIFTSSIMH WVRQAPGQGLEWIGYIKPYNDGTKYNEKFKGRATL TSDRSTSTAYMELSSLRSEDTAVYYCAREGGNDYY DTMDYVVGQGTLVTVSSASTKGPSVFPLAPSSKST SGGTAALGCLVKDYFPEPVTVSWNSGALTSGVHTF PAVLQSSGLYSLSSVVTVPSSSLGTQTYICNVNHK PSNTKVDKKVEPKSCDKTHTCPPCPAPELLGGPSV FLFPPKPKDTLMISRTPEVTCVVVDVSHEDPEVKF NWYVDGVEVHNAKTKPREEQYNSTYRVVSVLTVLH QDWLNGKEYKCKVSNKALPAPIEKTISKAKGQPRE PQVYTLPPSRDELTKNQVSLTCLVKGFYPSDIAVE WESNGQPENNYKTTPPVLDSDGSFFLYSKLTVDKS RWQQGNVFSCSVMHEALHNHYTQKSLCLSPG (SEQ ID NO: 55) |
| G4723A Light | DIQMTQSPSSLSASVGDRVTITCRASQDINSYLSW FQQKPGKAPKTLIYRVNRLVDGVPSRFSGSGSGND YTLTISSLQPEDFATYYCLQYDAFPYTFGQGTKVE IKRTVAAPSVFIFPPSDEQLKSGTASVVCLLNNFY PREAKVQWKVDNALQSGNSQESVTEQDSKDSTYSL SSTLTLSKADYEKHKVYACEVTHQGLSSPVTKSFN RGEC (SEQ ID NO: 56) |

In certain embodiments, an anti-FOLR1 antibody is encoded by the plasmids deposited with the American Type Culture Collection (ATCC), located at 10801 University Boulevard, Manassas, Va. 20110 on Apr. 7, 2010 under the terms of the Budapest Treaty and having ATCC deposit nos. PTA-10772 and PTA-10773 or 10774.

The cell-binding agent (e.g., antibody or antigen-binding fragment thereof) can be CD37-3, huMov19, Z4681A, G4732A, huB4, huCMET-27, huADAM9, or Herceptin (trastuzumab).

The drug can be a cytotoxic agent. The cytotoxic agent can be any compound that results in the death of a cell, or induces cell death, or in some manner decreases cell viability, and includes, for example, maytansinoids, maytansinoid analogs, benzodiazepines (e.g. an indolino-benzodiazepine (IGN) or a pyrrolobenzodiazepine (PBD)), taxoids, CC-1065 and CC-1065 analogs, duocarmycins and duocarmycin analogs, enediynes, such as calicheamicins, dolastatin and dolastatin analogs including auristatins, tomaymycin derivaties, leptomycin derivaties, methotrexate, cisplatin, carboplatin, daunorubicin, doxorubicin, vincristine, vinblastine, melphalan, mitomycin C, chlorambucil and morpholino doxorubicin. In one embodiment, the maytansinoid can be DM1. In another embodiment, the maytansinoid can be DM4. In one embodiment, the indolino-benzodiazepine can be DGN462. In another embodiment, the indolino-benzodiazepine can be DGN549. In other embodiments, the pyrrolobenzodiazepine can be talirine, tesirine, SJG136, or SGD1882.

Suitable linking groups are well known in the art and include, for example, disulfide groups, thioether groups, acid labile groups, photolabile groups, peptidase labile groups and esterase labile groups. Linker molecules include, for example, N-succinimidyl 3-(2-pyridyldithio) propionate (SPDP) (see, e.g., Carlsson et al., *Biochem. J.,* 173: 723-737 (1978)), N-succinimidyl 4-(2-pyridyldithio)butanoate (SPDB) (see, e.g., U.S. Pat. No. 4,563,304), N-succinimidyl 4-(2-pyridyldithio)2-sulfobutanoate (sulfo-SPDB) (see US Publication No. 20090274713), N-succinimidyl 4-(2-pyridyldithio) pentanoate (SPP) (see, e.g., CAS Registry number 341498-08-6), 2-iminothiolane, or acetylsuccinic anhydride. The linker can be, SMCC, sSPDB, or a peptide linker.

An ADC can contain multiple drugs per antibody. The number of drugs per antibody is often referred to as the drug antibody ratio (DAR). In one aspect, the number of drug molecules that can be attached to a cell binding agent can average from about 2 to about 8. Thus, by way of example, the processes provided herein can target a DAR of about 3 to about 4.

In some embodiments, the ADC is "IMGN853." As used herein "IMGN853" refers to an ADC containing the huMov19 antibody, the sulfoSPDB linker, and the DM4 maytansinoid. HuMov19 (M9346A) contains a heavy chain comprising the same amino acid sequence as the amino acid sequence of the heavy chain encoded by the plasmid deposited with the American Type Culture Collection (ATCC) as PTA-10772 and (ii) a light chain comprising the same amino acid sequence as the amino acid sequence of the light chain encoded by the plasmid deposited with the ATCC as PTA-10774. IMGN853 is described in WO2011/106528, which is herein incorporated by reference in its entirety.

In some embodiments, the ADC is "IMGN779." As used herein, "IMGN779" refers to an ADC containing the Z4681A antibody, the sulfoSPDB linker, and the indolino-benzodiazepine DGN462.

In some embodiments, the ADC is "IMGN632." As used herein, "IMGN632" refers to the ADC composition shown in FIG. 11. The ADC composition comprises ADCs comprising an average of 1.5 to 2.1 DGN549-C cytotoxic agents per huCD123-6Gv4.7 ("G4723A") antibody in a sulfonated version (FIG. 11, top panel). The ADC composition can also comprise the unsulfonated ADC (the mono-imine structure shown in FIG. 11, bottom panel).

Exemplary ADCs that bind to ADAM9 are disclosed in PCT/US2017/067823 (published as WO2018119196), which is herein incorporated by reference in its entirety. Exemplary ADCs that bind to ADAM9 are also disclosed in U.S. Application No. 62/691,342, filed Jun. 28, 2018, which is herein incorporated by reference in its entirety. Exemplary ADCs that bind to cMET are disclosed in PCT/US2018/012168 (published as WO2018129029), which is herein incorporated by reference in its entirety. Exemplary ADCS that bind to CD19 are disclosed in WO2012156455, which is herein incorporated by reference in its entirety.

V. EXAMPLES

Example 1: A Continuous Conjugation Process for the Conjugation of IMGN853

To reduce processing time and improve yields for large-scale manufacturing of antibody drug conjugates (ADCs), a continuous conjugation process was developed. In continuous conjugation, the processing steps happen simultaneously. Recirculation of the conjugate during purification and buffer exchange steps, as well as intermediate hold steps that were used during batch conjugation were eliminated using continuous conjugation. In this manner, the process ran continuously for 4-5 days, and the conjugate was formulated directly after passing out of the TFF purification steps. In addition, in-line process analytical technology (PAT) systems were used to allow for direct measurements of the conjugate, so off-line assays and handling of material by operators was eliminated. Further, because processing time was reduced, the requirement for large equipment to produce large quantities of conjugates was not necessary: smaller equipment and shorter processing times were sufficient to produce large amounts of product. In addition, for a given quantity of final conjugate produced, the product quality profile was more consistent when generated using continuous processing. By contrast, the requirement for multiple batches in bulk conjugation introduces the potential for increased batch-to-batch variability in product quality.

The continuous conjugation process for the conjugation of the ADC "IMGN853" is detailed in the flow diagram represented in FIG. 4. IMGN853 contains an anti-FOLR1 antibody ("huMov19") conjugated to DM4 maytansinoid drugs through sulfo-SPDB linkers. IMGN853 is described in WO 2011/106528, which is herein incorporated by reference in its entirety.

Example 1A: Flow Chemistry Studies

Conventional IMGN853 conjugation involves an in-situ reaction between the maytansinoid drug DM4 and the N-succinimidyl 4-(2-pyridyldithio)-2-sulfobutanoate (sSPDB) linker in 70% N,N-dimethylacetamide (DMA). Appropriate volumes of DM4 and sSPDB stock solution are added to the in-situ reaction vessel. Additional DMA (solvent) is added to the in-situ vessel to target 70% DMA by volume. The final reactant added to the in-situ reaction vessel is reaction buffer. After the reaction buffer is added, the in-situ reaction initiates and mixes for 60-120 minutes. The in-situ components are then added to a conjugation vessel containing the M9346A (huMov19) antibody that has been diafiltered into reaction buffer. All of the components are mixed, and the conjugation reaction proceeds with gentle mixing overnight to generate the desired conjugate with a target drug-antibody ratio (DAR) of 3.4.

In this study, a continuous conjugation of IMGN853 was performed. The continuous conjugation reaction used all of the same stoichiometric IMGN853 parameters with one notable exception. The pH of the reaction buffer for the conjugation reaction was increased from 7.6 to 8.7. The pH of the in-situ reaction buffer was not changed and remained at 7.6. The increase in pH was instituted to increase the conjugation reaction kinetics. Instead of targeting 18 hours for the conjugation reaction, the higher pH buffer generated the conjugate in approximately 4 hours to allow for a faster readout and more flexible experimental protocols.

For the continuous conjugation experiments, syringe pumps were used to continuously add reagents. The set up shown in FIG. 5. Three syringe pumps were used. The first syringe pump controlled the addition of the in-situ components dissolved in DMA. These included the DM4 (payload), sSPDB (linker), and DMA (additional solvent). These three components were combined in stoichiometric ratios and then drawn into a 2.5 mL Hamilton Gastight syringe. The second syringe pump metered the addition of in-situ reaction buffer. A 5 mL plastic BD syringe was used. 1/16" PEEK tubing was used for the continuous conjugation studies. The in-situ reaction buffer and DMA component feed lines were fed into an in-line static mixer to ensure adequate mixing of the two reagents. These two feed streams combined and exited through a single piece of tubing from the static mixer of the same tubing material. The flow rates for the in-situ buffer and DMA components were 952.9 nL/min and 2.2233 µL/min, respectively. Targeting a 90 minute in-situ reaction required 18.6 centimeters of PEEK tubing based on the flow rate for the two inlet streams and the cross-sectional area of the tubing used. This length of PEEK tubing where the in-situ reaction occurred was fed into a second in-line static mixer. The other inlet for the second static mixer was from the third syringe pump. The third syringe controlled the addition of the antibody and conjugation reaction buffer (pH 8.7). The antibody and conjugation reaction buffer were combined and drawn into a 30 mL plastic BD syringe. The same PEEK tubing was used to feed the antibody and conjugation reaction buffer at a flow rate of 24.615 µL/min. Similar to the in-situ static mixer, the second static mixer ensured the conjugation reaction components were well mixed and combined into a single exiting stream. The conjugation reactants left the static mixer in a piece of the same PEEK tubing that was 4.3 meters long to achieve the target conjugation reaction duration of 4 hours.

The studies were performed by filling all three of the syringes prior to the start of any flow. First, the in-situ reaction buffer (syringe 2) and DMA components (syringe 1) pumps were started at the same time. After approximately 90 minutes, pump three (antibody and conjugation reaction buffer) was started. Approximately five hours from starting the first two pumps, conjugate eluted from the 4.3 meter long piece of PEEK tubing. Sample analysis was performed by collecting directly from the end (i.e. pooled samples were collected from the well-mixed conjugate pool). To measure the flow rates of the in-situ and conjugation feed steams (from any pump), flow meters can further be used. Flow meters serve as a process analytical technology (PAT) mechanism to ensure adequate control over the stoichiometry of the reactions.

The results of a first IMGN853 continuous conjugations study are shown in Table 4.

TABLE 4

Results of a first IMGN853 continuous conjugation study.

| Sample | SEC | | | | Free Drug | | | |
| --- | --- | --- | --- | --- | --- | --- | --- | --- |
|  | DAR | HMW | Monomer | LMW | DM4-S-TBA | DM4 | DM4-S-Py | Total FM |
| Control (Batch) PC-002 | 3.52 | 1.04% | 98.93% | 0.04% | 17.35% | 4.09% | 2.38% | 24.72% |
| In-Line (Early), unfiltered | 3.23 | 1.19% | 98.71% | 0.11% |  |  |  |  |
| In-Line (End), unfiltered | 3.56 | 1.13% | 98.82% | 0.06% | 19.33% | 5.49% | 2.89% | 29.54% |
| Continuous Pooled (PC-002) | 3.58 | 1.20% | 98.75% | 0.06% | 18.17% | 4.52% | 1.95% | 25.92% |

The study showed that the continuous conjugation product quality was comparable to control (batch) product quality performed side-by-side. The product quality took some time to reach steady-state as evidenced by the lower drug-antibody ratio (DAR) at the "early" time point. This was consistent in a second study where the 30 minute sample also had a slightly lower DAR. By 3 hours in the second study, the product quality had achieved steady-state at the target DAR (as compared to the side-by-side batch control). In addition to DAR, the product quality was also comparable in terms of monomer and free drug levels. Together, these results indicate the continuous conjugation process performed well and was comparable to side-by-side batch control in terms of product quality.

The results of a second study are shown in Table 5.

TABLE 5

Results of a second IMGN853 continuous conjugation study.

| Sample | SEC | | | | Free Drug | | | |
| --- | --- | --- | --- | --- | --- | --- | --- | --- |
|  | DAR | HMW | Monomer | LMW | DM4-S-TBA | DM4 | DM4-S-Py | Total FM |
| NG006_Control PC002 | 3.71 | 1.05 | 98.95 | 0.00 | 18.81% | 4.82% | 2.55% | 27.06% |
| NG006_In-line (30 min) | 3.21 | 1.09 | 98.91 | 0.00 | 15.56% | 3.53% | 0.74% | 21.07% |

TABLE 5-continued

Results of a second IMGN853 continuous conjugation study.

| Sample | SEC | | | | Free Drug | | | |
| --- | --- | --- | --- | --- | --- | --- | --- | --- |
| | DAR | HMW | Monomer | LMW | DM4-S-TBA | DM4 | DM4-S-Py | Total FM |
| NG006_In-line (3 h) | 3.68 | 0.95 | 99.05 | 0.00 | 18.78% | 5.13% | 3.18% | 28.54% |
| NG006_In-Line (16 h) | 3.68 | 0.89 | 99.11 | 0.00 | 18.95% | 5.77% | 2.66% | 29.02% |
| NG006_In-Line (24 h) | 3.73 | 0.93 | 99.07 | 0.00 | 18.72% | 4.84% | 2.81% | 27.01% |
| NG006_In-Line (40 h) | 3.70 | 1.13 | 98.87 | 0.00 | 18.37% | 4.43% | 2.69% | 26.91% |
| NG006_Pooled, filtered | 3.83 | 1.25 | 98.75 | 0.00 | 21.64% | 4.03% | 2.92% | 29.38% |

The same parameters were used in this study as the study above, but the process was run continuously for 40 hours to show that 100 mg equipment setup could be used to generate 10× more product by running the process longer. The results showed that between 30 minutes and 3 hours of eluting conjugate, the conjugate reached steady-state and was comparable to the side-by-side batch control by SEC and free drug analysis. The product quality at three hours was nearly identical to the conjugate eluting at 40 hours indicating the continuous process performed consistently as long as the feed reagents were supplied to the reaction tubing.

In a manufacturing setting, pumps for each individual reagent can be used to keep stock solutions separate. Instead of combining DM4, sSPDB, or DMA into a single feed stream, each of the stock solutions can be fed separately to a collection vessel or directly into the in-situ reaction. The same can be applied for the antibody and conjugation reaction buffer. The stock solution of antibody can be fed using a designated pump while a separate pump controls the addition of conjugation reaction buffer at the appropriate volumetric ratio to the other conjugation reaction components.

Other PAT mechanisms can be used to monitor either the in-situ or conjugation reaction as it proceeds. A Fourier Transform Infared (FTIR) flow cell can be used in-line to monitor the in-situ or conjugation reaction performance. Additionally, multiple FTIR flow cells or a similar PAT tool can be placed at intermediate locations along the in-situ and conjugation reaction tubing to monitor the reaction as it occurs. The formation of the desired conjugate can be measured from the start of the reaction all the way to the end. Any significant change in the PAT signal can then be used to identify where in either the in-situ or conjugation reaction (beginning, middle, or end) an error has occurred. For the conjugate, an alternative PAT mechanism can be a rapid High Performance Liquid Chromatography (HPLC)-based instrument (Ultra Performance Liquid Chromatography (UPLC)) with or without a UV sensor. The HPLC-based analysis can be used to measure the DAR while UV sensors placed in-line can monitor the antibody concentration in the conjugation reaction.

Example 1B: Single-Pass Tangential Flow Filtration Studies

Conventional tangential flow filtration (TFF) is used twice during the IMGN853 drug substance process. First, TFF is performed to buffer-exchange the formulated antibody into conjugation reaction buffer, prior to the conjugation reaction (TFF1). After the conjugation reaction, TFF is used to remove residual impurities from the crude-reaction mixer and buffer-exchange the conjugate from conjugation reaction buffer into basal formulation buffer (TFF2). A continuous process was developed to replace both of these conventional TFF steps with single-pass TFF (SPTFF) method. Continuous SPTFF utilized the in-line concentration (ILC) and in-line diafiltration (ILDF) technologies from Pall Life Sciences.

For TFF1, the antibody was diafiltered for 8 diavolumes at 30 mg/mL during conventional processing. The incoming antibody was formulated at 60 mg/mL and was diluted prior to diafiltering during conventional TFF1 processing. During continuous processing, the formulated antibody at 60 mg/mL was fed into a T-connector, where another pump added conjugation reaction buffer to dilute the antibody to the target concentration of 30 mg/mL. After the T-connector, a single-feed stream of 30 mg/mL antibody was fed into the ILDF module. The ILDF diafiltration buffer pump controlled the addition of conjugation reaction buffer to the ILDF module so that the buffer-exchange was achieved in a single pass. The antibody exiting the ILDF was at 30 mg/mL in the conjugation reaction buffer.

PAT control can be implemented at various places to monitor and control this unit operation. A FlowVPE or UV sensor can be placed on the formulated antibody feed stream (60 mg/mL), diluted antibody feed steam (30 mg/mL), and/or on the buffer-exchanged antibody in conjugation reaction buffer. The FlowVPE or UV sensor can be used to measure the concentration of the antibody in the different feed steams. Additionally, flow meters on all of the feed steams can be used to monitor and adjust the flow rate of any component to ensure the buffer-exchange in the ILDF is occurring at 30 mg/mL. Furthermore, a conductivity or pH probe after the ILDF can be used to ensure that the buffer-exchange of the antibody into the conjugation reaction buffer was complete.

After the conjugation, conventional TFF2 is typically performed in three steps which all occur in a single unit operation. The post-conjugation crude reaction mixture is first concentrated via ultrafiltration to 30 mg/mL (from 15 mg/mL post-conjugation reaction). The conjugate is then diafiltered for 4 diavolumes against conjugation reaction buffer in what is referred to as Stage I of TFF2. During Stage I, residual impurities are removed from the crude-reaction mixture. Directly after Stage I, Stage II is performed by diafiltering the conjugate against 8 diavolumes of basal formulation buffer. Stage II is designed as strictly a buffer-exchange step but does contribute to additional clearance of residual impurities.

For a continuous process utilizing SPTFF, three separate steps were evaluated. First, the ILC module for concentrating was used. The ILC followed the conjugation reaction tubing. In a single pass, the conjugate entering the ILC at 15 mg/mL was concentrated to 30 mg/mL with the volume removed being diverted to waste. The concentration factor used for IMGN853 and described in this instance was two (2), but other concentration factors could be used in place to achieve the same result of concentrating the conjugate before diafiltration.

After the ILC, the 30 mg/mL conjugate feed stream was fed into the first ILDF (ILDF1) which was meant to emulate Stage I. The diafiltration buffer feed for ILDF1 was conjugation reaction buffer, and it was added at the appropriate volume to achieve the desired number of diavolumes in a single pass. For IMGN853, Stage I was achieved in four conventional diavolumes. Proof of concept studies evaluated the removal of residual impurities as a function of number of diavolumes by adjusting the flow rate of the diafiltration buffer feed pump.

After ILDF1, the conjugate remained at 30 mg/mL but had significantly lower concentrations of impurities present. The exit stream from ILDF1 fed ILDF2 where the diafiltration buffer was basal formulation buffer. The conjugate entered ILDF at 30 mg/mL in conjugation reaction buffer (pH 7.6 to 8.7) and exited the ILDF2 at 30 mg/mL in pH 5.0 buffer.

Initial proof of concept studies performed using Pall Life Sciences ILDF modules used a T01 module which has a membrane area of 0.11 $m^2$. The module was evaluated at flow rates between 1-4 mL/min for the conjugate feed. The diafiltration buffer feed rates were varied such that the number of diavolumes varied. Processing of between one and thirteen diavolumes were evaluated using the ILDF. For all of the studies, conjugate material was generated using conventional batch processing and frozen into aliquots. Free maytansinoid species were quantified prior to freezing and again after thawing (prior to processing). The crude-reaction mixture was fed into the ILC. The flow rate of the retentate stream was measured using a flow meter to calculate the concentration factor achieved over the module. The IMGN853 process and all studies were performed using a target concentration factor of two.

A first study with ILDF was conducted to evaluate clearance of residual impurities from IMGN853 conjugation reaction. A bulk conjugation was performed to generate material for the study using target reaction conditions. The post-conjugation crude reaction mixture was filtered, aliquotted, and frozen prior to use. After thawing, the crude reaction mixture was concentrated using the single pass ILC module targeting a concentration factor of two. The crude reaction mixture was at 15 mg/mL, and the target retentate concentration of the conjugate post-ILC was 30 mg/mL. The post-ILC conjugate was then diluted to 10 mg/mL using conjugation reaction buffer to test the ILDF module at a low starting concentration. The dilution from 30 mg/mL to 10 mg/mL prior to the ILDF effectively reduced the load of free drug impurities in the conjugate feed. This is evident in FIG. 6 showing free drug impurity levels for the four main impurity species before and after the ILC. The post-conjugation crude reaction mixture has high impurity levels. After concentrating over the ILC and then diluting to 10 mg/mL, the concentration of impurities were reduced to approximately ⅓ of the starting concentration.

The 10 mg/mL conjugate was fed to the T01 ILDF module at 4 mL/min targeting 7 diavolumes of processing for stage I. The Stage I diafiltration buffer was conjugation reaction buffer (15 mM potassium phosphate, 2 mM EDTA, pH 8.7). Samples were taken from the retentate line and analyzed for protein concentration to determine when the conjugate eluted from the system. After the concentration reached a steady-state, samples were collected from the retentate line and analyzed by RP-HPLC to quantify free drug impurity levels and calculate clearance over the ILDF. FIG. 6 shows the results for three samples taken from the ILDF1 step: early, late, and pooled. The early sample was taken shortly after steady-state was achieved on the ILDF. The impurity levels in all three samples were well below specification limits. The reduction in free drug levels over the ILDF was significant and acceptable in terms of process performance.

After the first pass over the ILDF against conjugation reaction buffer to mimic Stage I of TFF2, the resulting pooled conjugate was then passed through the module again to emulate Stage II. Prior to Stage II, the module was flushed and then prepped for diafiltration against basal formulation buffer (10 mM acetate, 9% sucrose, pH 5.0). The conjugate was fed at 4 mL/min and the diafiltration buffer feed flow rate was set to target 13 diavolumes across the ILDF. This number was chosen to match eight diavolumes for conventional TFF processing.

Similar to ILDF1, samples were collected from the retentate line and analyzed to measure concentration of the antibody. When the protein concentration was detected, the product was collected and samples were taken periodically from the retentate line. After the system reached steady-stage, the samples collected from the retentate line were analyzed by RP-HPLC to quantify residual impurity levels and to calculate clearance over ILDF2. After the product had been passed over the ILDF and collected, the pooled material was filtered and then analyzed by SEC and RP-HPLC. The results for all samples from ILDF2, emulating the Stage II buffer-exchange during conventional TFF2 processing, are shown in FIG. 6. Free drug levels were all <1% which is well below the final specification for purified drug substance (DS). These results demonstrate continuous purification of IMGN853 conjugate by SPTFF is feasible and capable of generating purified conjugate with acceptable product quality as measured by SEC and RP-HPLC.

The next study examined the clearance capacity of the ILDF to remove residual impurities at a feed concentration of 15 mg/mL. This concentration was chosen after the first study showed adequate clearance at 10 mg/mL. During this study, the conjugate was not processed by the ILC. Crude conjugate reaction mixture from a bulk conjugation was thawed and fed directly to the ILDF. A T01 ILDF module was used and the feed flow rate was 4 mL/min. Conjugation reaction buffer was used for the diafiltration buffer and the feed flow rate was set to initially target one diavolume. When the conjugate was detected in the retentate by measuring concentration, samples were collected from the retentate line and analyzed by RP-HPLC to quantify free drug levels. The results are shown in FIG. 7. The post-conjugation crude reaction mixture had high starting levels that were in line with previous conjugations. After a single pass equivalent to one diavolume of processing, the total free drug levels dropped from approximately 26% in the feed to 7% in the retentate.

The diafiltration feed flow rate was then increased to target seven diavolumes, which is comparable to the target four diavolumes for conventional TFF processing. After the system reached steady-state, the free drug levels were measured in the retentate. As shown in FIG. 4, the free drug levels dropped significantly after a single pass under these processing conditions. The final total free drug levels were below 1%, which is within the acceptance range for final product quality. These results indicate the ILDF performs well at 15 mg/mL feed conjugate concentration and removes impurities to levels below specification limits when processed for seven diavolumes.

For comparison, free drug impurity clearance values from a batch TFF2 purification process are shown in FIG. 8. After 4 diavolumes of conventional TFF2 batch processing (solid bars), the total free drug impurity level was 3.4%. After 7 diavolumes of SPTFF processing (striped bars), which is equivalent to 4 conventional diavolumes, the total free drug level was 0.7%. One important difference between these two studies was the concentration of the conjugate during purification. For the continuous processing study, the conjugate feed to the ILDF module was 15 mg/mL. The conventional batch TFF processing was performed at 30 mg/mL.

The ILDF performed well at 15 mg/mL with no concerns of pressure or product quality, so the conjugate concentration of the feed was increased to optimize yield from the ILDF in a follow up study. The target feed conjugate concentration was 30 mg/mL. Crude reaction mixture was first passed through the ILC targeting a concentration factor of two. The conjugate entered the ILC at 15 mg/mL and was concentrated to a target of 30 mg/mL. The resulting conjugate at 30 mg/mL was collected before feeding to the ILDF. The diafiltration buffer for the ILDF was conjugation reaction buffer, and the feed flow rate was set to target seven diavolumes. The feed flow rate for the conjugate at 30 mg/mL was 4 mL/min on a T01 ILDF module. After protein was detected in the retentate stream, the conjugate was collected and samples were collected. The system was allowed to reach a steady-state before a sample was analyzed by RP-HPLC to quantify free drug levels and to calculate clearance over the ILDF. The results are shown in FIG. 9. The post-ILDF free drug levels were compared to samples taken prior to the ILC (15 mg/mL of crude reaction mixture) and post-ILC (30 mg/mL). The post-ILC free drug levels increased slightly which was attributed to slightly overconcentrating the conjugate. The post-ILC conjugate was measured at 31 mg/mL indicating a concentration factor of 2.1 was used. The resulting free drug levels were slightly higher, but to accurately assess the ILDF, the conjugate was diluted to 30 mg/mL by adding the appropriate volume of conjugation reaction buffer to the pooled material prior to feeding the ILDF.

The sample collected and analyzed by RP-HPLC from the ILDF at 4 mL/min showed clearance of free drug species from the pre-ILDF/post-ILC sample. However, the concentration of conjugate in the retentate was measured at approximately 20 mg/mL. It was posited that the drop in conjugate concentration was attributed to aggregation and accumulation of product on the membrane in the cassette. To alleviate any clogging and reduce the pressure in the system, the feed flow rate was reduced to 3 mL/min. Accordingly, the diafiltration buffer feed pump flow rate was also decreased such that seven diavolumes was targeted for processing. After reducing the inlet flow rates for the ILDF, a sample was collected from the retentate and analyzed for concentration and free drug levels. The concentration of the sample was determined to be 22.5 mg/mL, and the free drug levels were comparable to the sample measured at 4 mL/min. Collectively, this indicates 7 diavolumes of processing is sufficient to purify the conjugate but a maximum of 23 mg/mL conjugate concentration in the retentate was observed.

Example 2: A Continuous Conjugation Process for the Conjugation of IMGN632

The continuous conjugation process for the conjugation of the ADC IMGN632 is detailed in flow diagram represented in FIG. 10. IMGN632 contains an anti-CD123 antibody ("G4732A") linked to the cytotoxic payload DGN549-C. IMGN632 is shown in FIG. 11.

Example 2A: Flow Chemistry Studies

The reaction set up is similar to the set up shown in FIG. 5. The first syringe contains the DNA-alkylating IGN payload "DGN549C" dissolved in DMA. The second syringe contains bisulfite stock solution and 50 mM succinate pH 3.3 at appropriate volumetric ratios. Both of these feed streams mix in the static in-line mixer to initiate the sulfonation reaction. The DGN549C targets a final concentration of 1 mM in the mixed stream. The resulting mixture is 50 mM succinate pH 3.3 and 50% DMA with a 1.4 molar excess of bisulfite to DGN ratio. The two feed streams exit the static in-line mixer in a single stream. The length of the tubing is determined based on volumetric flow rates such that the residence time of the reactants in the tubing targets 3 hours. The temperature of the sulfonation reaction is 25° C. and is maintained by submerging the tubing into a temperature controlled water bath. The third syringe (Ab+Buffer syringe from FIG. 5), contains reoxidized anti-CD123 antibody ("G4723") that has been adjusted to pH 6.0 with 5% succinic acid. Appropriate volumes of DMA and 50 mM potassium phosphate are added to the reoxidized antibody mixture. The homogeneous mixture is drawn up in a single syringe to be combined in-line with the sulfonation reaction.

The sulfonation feed stream enters a second static mixer where it mixes with the pH adjusted reoxidized antibody. The volumetric flow rates are adjusted such that the final conjugation stream exiting the second static mixer achieves the desired reaction conditions of 2.0 mg/mL antibody concentration, 15% DMA, and a 3.5 molar ratio of DGN to antibody. The conjugate tubing coil length is chosen such that the residence time targets a conjugation reaction duration of 20 hours. Similar to the sulfonation tubing, the conjugation tubing is submerged in a temperature controlled water bath set at 25° C.

Example 2B: Single-Pass Tangential Flow Filtration Studies

The pH adjusted crude conjugate mixture at pH 4.2 is fed into the ILC at a concentration of 2 mg/mL targeting a concentration factor of four so that the retentate is approximately 8 mg/mL. The resulting conjugate material at 8 mg/mL is fed to an ILDF SPTFF module. The diafiltration buffer for the first ILDF is 10 mM succinate, 50 µM bisulfite pH 4.2 with 10% (v/v) DMA. The flow rates of the ILDF are adjusted to target 7 diavolumes, matching the four diavolumes used during conventional batch processing.

After the first ILDF, the material is fed at the same concentration to a second ILDF module where the diafiltration buffer is 10 mM succinate 50 µM bisulfite pH 4.2. The flow rates of the diafiltration buffer feed and product feed are set such that the target number of diavolumes is 15 to achieve a similar buffer-exchange to the 10 diavolumes targeted during conventional batch TFF processing.

Example 3: Pulse Treatment Improves Conjugation of IMGN853

The present inventors have discovered that continuous flow conjugation allows for a pulsing change of a parameter (e.g., temperature or pH). The pulsing is possible in a continuous flow conjugation process where reactions take place as reagents pass through coils and tubing with small volumes. For example, short sections of the coils or tubing can be rapidly heated (e.g., by insulation) or cooled to create a short temperature excursion or "pulse." (See e.g., FIG. 12).

The inventors have further discovered that pulsing changes in reaction parameters is advantageous, for example, where longer exposure to the altered parameter may damage the process or result in negative impacts to product quality. For instance, increasing the temperature of a conjugation reaction for an extended period of time can result in increased aggregation. In contrast, as demonstrated herein, increasing the temperature of a conjugation reaction in only short pulses of time can increase reaction speed without significantly increasing aggregate formation.

Conjugation of IMGN853 was performed in vials with temperature pulsing, which involved placing a vial containing the conjugation reaction components at 20° C. for about 30 minutes and then pulsing by placing the vial into a water bath at a higher temperature for a specified pulse time and then returning the vial to 20° C. The vial recovered at 20° C. until the next pulse occurred, and the process was repeated for a specified number of pulses. Four different pulse conditions were assessed: 4 pulses at 40° C. for 7 minutes each; 4 pulses at 42.5° C. for 7 minutes each; 5 pulses at 50° C. for 1 minute each, and 5 pulses at 60° C. for 1 minute each. A control reaction was performed with a steady 20° C. temperature.

The extent of reaction completion (%) was used to determine the reaction rate. At a steady 20° C. temperature, an IMGN853 conjugation reaction requires about 8 hours to reach completion. (See FIG. 14, left panel). All pulse conditions tested decreased reaction time (i.e., reach 100% completion in less time). (See FIG. 14, left panel). Pulsing (5 times) at 60° C. for 1 minute per pulse dramatically increased the occurrence of high molecular weigh (HMW; aggregate) species. (See FIG. 14, right panel). In contrast, all of the other pulsing conditions tested had little impact on the occurrence of HWM (aggregate) species.

This data demonstrate that reaction conditions enabled by continuous flow conjugation can improve reaction kinetics and productivity without compromising product quality.

Example 4: Single-Step Preparation of Antibody for Conjugation

In Example 2, the IMGN632 drug substance process involves two steps to prepare the G4723A antibody for conjugation: reduction and reoxidation (FIG. 10, top left box). The reduction of the G4723A antibody reduces interchain disulfides between native cysteines and removes capping groups on the C442 engineered cysteine residues. This step involves addition of 25 molar equivalents of TCEP to the G4723A antibody. After the reduction reaction, the reduced antibody mixture is buffer-exchanged to remove any residual TCEP and prepare the antibody for the reoxidation reaction. The reoxidation step involves addition of 8 molar equivalents of DHAA to reduced G4723A antibody to reform the interchain disulfides of the antibody. The reaction leaves the C442 engineered cysteines residues as free thiols that can be conjugated to the payload via a maleimide function group.

To demonstrate the feasibility of performing these reactions in a continuous format, small-scale studies were performed using a micro-scale flow reactor.

Example 4A: Reduction Reaction

The reduction reaction was performed to demonstrate that the formulated G4723A antibody could be reduced in a flow reactor and yield antibody with consistent product quality as a side-by-side batch reaction.

A 150 mg reduction scale based on G4723A antibody was performed to demonstrate continuous reduction in a flow reactor. The formulated G4723A antibody at 51.1 mg/mL was used as one feed stream. The antibody solution was drawn into a syringe. The TCEP-HCl stock solution, prepared at 100 mM in 50 mM potassium phosphate, pH 7.5 was combined with additional 50 mM potassium phosphate, pH 7.5 as the second feed stream for the continuous reaction. This was done due to the low flow rates and volumetric ratios of TCEP-HCl stock solution to the 50 mM potassium phosphate, pH 7.5 buffer feed streams if they were kept separate. The additional 50 mM potassium phosphate, pH 7.5 buffer is required to dilute the formulated G4723A antibody to 5 mg/mL for the reduction reaction.

The reaction was setup using Harvard Apparatus syringe pumps and $\frac{1}{16}^{th}$ PEEK tubing. The volumetric ratio of the two feed streams were chosen such that the final reaction stoichiometry after mixing was at the target reaction conditions –25 molar equivalents of TCEP-HCl to antibody, 5 mg/mL antibody. The combined volumetric flow rate of the two feed streams was used to calculate the length of PEEK tubing required so that the reaction duration, or residence time in the flow reactor, was 16 hours. For this experiment, both the side-by-side batch control and the continuous reactions were performed at ambient temperature.

A side-by-side batch control reduction reaction was setup at a 20 mg G4723A antibody scale. All reaction parameters were matched. After the 16 hour reaction duration, the control and continuous reactions were sampled and labeled for analysis. The continuous reduction reaction was sampled from the outlet of the flow reactor. The bulk control batch reaction was sampled for analysis.

To characterize the reduction reaction, the samples were labeled with Alexa-MAL 488 fluorophore, which reacts with free thiols on the antibody and can be detected by UV spectrometry. The samples were reacted with the Alexa-MAL 488 and analyzed by SE-HPLC to calculate the Alexa-Antibody ratio. The results for the continuous and side-by-side control reactions are shown in Table 6.

TABLE 6

| Batch vs. Continuous Reduction Reaction | |
|---|---|
| Sample | Alexa-Antibody Ratio |
| Alexa-Labeled, Reduced (Control) | 7.50 |
| Alexa-Labeled, Reduced (Continuous) | 7.92 |

The data shown in Table 6 indicate the G4723A antibody was reduced by traditional batch and continuous processing. For the formulated G4723A antibody prior to reduction, no Alexa labeling has been observed. After the interchain disulfides are reduced to form free thiols during the reduction reaction, the Alexa-MAL 488 is able to react with and conjugate the free thiol. Complete reduction of the engineered cysteines and native cysteines of the antibody would result in 10 labels.

Approximately 7-8 Alexa-MAL 488 labels were detected in both samples, indicating the G4723A antibody was reduced. These results were consistent with previous development studies on smaller scale where 8 Alexa-MAL 488 labels are identified after the reduction reaction. The difference from the theoretical target of 10 labels is likely due to some reoxidation that occurs on small scale, driven by air in the reaction vessel, causing free thiols to reform disulfides and decrease the number of available free thiols on the antibody for conjugation with Alexa-MAL 488.

Subsequent studies were repeated on larger scales and targeting shorter reduction times of approximately 3 hours. Similarly, the antibodies generated from these studies were labeled with Alexa-MAL 488 and characterized by SE-HPLC to compare the reaction efficiency. The product quality data from a subsequent study in which the reduction reaction time was targeted for 3 hours by increasing the volumetric flow rates of the two feed stream are shown in Table 7.

TABLE 7

Product Quality Evaluation of Continuous Reduction Reaction

| Sample | Alexa:Ab Ratio | HMW (%, SEC) | Monomer (%, by SEC) |
|---|---|---|---|
| Control_post-reduction | 8.50 | 0.57 | 99.17 |
| Continuous_post-reduction | 8.14 | 0.11 | 99.58 |

In addition to the Alexa:Ab ratio comparing the extent of the reduction reaction for the batch control and continuous reaction, the Monomer and HMW values for the two reaction products were measured. The data in Table 7 show that at a larger scale with higher volumetric flow rates, a continuous reduction reaction is comparable to the batch control. Additionally, there is a slight increase in the Monomer for the antibody produced by the continuous reaction.

These results demonstrate that the reduction reaction can be successfully performed in a continuous format using flow chemistry.

Example 4B: Reoxidation Reaction

The reoxidation reaction was performed to demonstrate the reduced G4723A antibody can be reoxidized in a continuous format.

Due to the scale of the reactions and flow reactor equipment, the reduced antibodies used to supply the reoxidation studies were NAP purified. During IMGN632 manufacturing, the reduced antibody is TFF purified to remove any residual TCEP-HCl from the reaction solution. After the TCEP-HCl is removed, DHAA is added to the reaction pool to reform the interchain disulfides of the antibody while leaving the two engineered C442 cysteine residues free for conjugation.

For the reoxidation studies, the G4723A antibody was first reduced using a batch reaction because of the need to setup the flow reactor equipment for the reoxidation reaction conditions. The reduction reaction was performed at 37° C. for 1 hour to completely reduce the antibody using the same 25 molar equivalents of TCEP-HCl relative to antibody at an antibody concentration of 5 mg/mL. After the reduction reaction, a sample of the reaction was Alexa-labeled to confirm the reduction of the antibody.

The reduced antibody was then NAP purified to remove residual TCEP-HCl from the solution prior to the addition of DHAA. The NAP purified material was measured for concentration to ensure the reoxidation reaction setup targeted the appropriate stoichiometric ratios. The NAP purified reduced antibody was split so that a side-by-side batch control reaction could be setup as a control with the continuous reoxidation sample.

For the continuous reoxidation reaction, three feed streams were used. The first was the reduced antibody that was NAP purified. The second was the 100 mM DHAA stock solution in DMA combined with additional DMA as required to target the final 5% (v/v) target for the reaction. The third was the 50 mM potassium phosphate pH 7.5 buffer that dilutes the NAP purified reduced antibody to the target 2.5 mg/mL antibody concentration for the reaction. The volumetric ratios of these three feed streams were determined based on the NAP purified reduced antibody concentration. The ratios were adjusted so that the combined feed streams gave the final target reoxidation reaction conditions after mixing. The volumetric flow rates were also used to calculate the amount of $\frac{1}{16}^{th}$ PEEK tubing required to target a reaction duration of 6 hours. The side-by-side reoxidation reaction and continuous reoxidation reaction were both setup at ambient temperature.

A 50 mg reoxidation reaction was setup for the continuous and control reactions. A total of 19.9 feet of $\frac{1}{16}^{th}$ PEEK tubing was required to target 6 hours based on the volumetric flow rates of the three feed streams. The continuous reoxidation reaction was sampled intermittently from the outlet of the flow reactor starting at 6.5 hours after the start of the reaction. The additional time was given to ensure the reaction reached steady-state based on potential backpressure within the flow reactor. Samples taken from the outlet of the flow reactor or from the bulk of the batch reoxidation reaction were all labeled with Alexa-MAL 488 fluorophore and characterized by SE-HPLC. The reoxidation reaction was sampled over time to ensure a steady-state was achieved. Additionally, the reduced antibody that was contained within the syringe and fed as one of the feed streams for the continuous reoxidation reaction was also labeled after the end of the study. This sample was tested to ensure the reduced antibody did not reoxidize while sitting in the syringe over the duration of the study. This sample was compared with the sample after reduction to understand any changes in the reduced antibody potentially caused by ambient conditions. The results of this continuous reoxidation study are shown in Table 8.

TABLE 8

Continuous Reoxidation Reaction Product Quality

| Sample | Alexa:Ab Ratio |
|---|---|
| NAP Purified, Post-Reduction T0 | 8.15 |
| Alexa-Labeled, Continuous Reoxidized (T = 7 h) | 2.37 |
| Alexa-Labeled, Continuous Reoxidized (T = 8 h) | 2.36 |
| Continuous Reoxidized (T = 9 h) | 2.35 |
| Control Reoxidized | 2.22 |
| Reduced Antibody from Syringe (End) | 7.36 |

These data indicate that the reoxidation reaction can be successfully performed using continuous processing. The reoxidized reaction performed in the flow reactor exhibited successful reoxidation with approximately 2.4 Alexa-MAL 488 labels. The data from the batch control reaction was comparable with approximately 2.2 Alexa-MAL 488 labels. The reduced antibody prior to reoxidation had approximately 8 labels which demonstrates the addition of the DHAA caused the reformation of disulfides. The remaining labels that were conjugated with Alexa-MAL 488 are the engineered cysteine residues that would be available for conjugation. Additionally, the data shown in Table 8 indicate the reduced antibody undergoes very minimal reoxidation under ambient conditions. The reduced antibody started with 8.15 labels and after the duration of the reoxidation study only decreased to 7.36. This data indicates the reoxidation was driven by the reaction with DHAA and not by air present in the reaction vessel or buffers.

Collectively, these results show the reoxidation reaction can be successfully achieved using continuous processing in a flow reactor.

It is to be appreciated that the Detailed Description section, and not the Summary and Abstract sections, is intended to be used to interpret the claims. The Summary and Abstract sections may set forth one or more but not all exemplary embodiments of the present invention as contemplated by the inventor(s), and thus, are not intended to limit the present invention and the appended claims in any way.

The present invention has been described above with the aid of functional building blocks illustrating the implementation of specified functions and relationships thereof The boundaries of these functional building blocks have been arbitrarily defined herein for the convenience of the description. Alternate boundaries can be defined so long as the specified functions and relationships thereof are appropriately performed.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present invention should not be limited by any of the above-described exemplary embodiments, but should be defined only in accordance with the following claims and their equivalents.

The claims in the instant application are different than those of the parent application or other related applications. The Applicant therefore rescinds any disclaimer of claim scope made in the parent application or any predecessor application in relation to the instant application. The Examiner is therefore advised that any such previous disclaimer and the cited references that it was made to avoid, may need to be revisited. Further, the Examiner is also reminded that any disclaimer made in the instant application should not be read into or against the parent application.

What is claimed is:

1. A continuous method for producing an antibody drug conjugate (ADC) composition comprising (i) conjugating an antibody or antigen-binding fragment thereof to a drug to form an ADC in a flow reactor, wherein one or more conjugation reagents are continuously added to the flow reactor, (ii) removing unconjugated drug, and (iii) exchanging the ADC into a stable buffer, wherein (i) to (iii) are performed continuously, and wherein single-pass tangential flow filtration (SPTFF), flow-through column-chromatography and/or countercurrent diafiltration is used to remove the unconjugated drug, wherein the ADC composition has an average drug-to-antibody ratio from 2 to 8; and wherein the ADC comprises an IgA, IgD, IgE, IgG, or IgM antibody or antigen-binding fragment thereof.

2. The method of claim 1, wherein flow-through column chromatography is used to remove the unconjugated drug and SPTFF and/or countercurrent diafiltration is used to exchange the ADC into the stable buffer.

3. The method of claim 1, further comprising pre-processing the antibody or antigen-binding fragment thereof or pre-processing the drug for conjugation, wherein the pre-processing is performed continuously with (i) to (iii) or is performed in bulk prior to (i) to (iii).

4. The method of claim 1, further comprising pre-processing an antibody or antigen-binding fragment thereof wherein the pre-processing and (i) to (iii) are performed continuously.

5. The method claim 3, wherein the pre-processing of the antibody or antigen-binding fragment thereof comprises exchanging the antibody or antigen-binding fragment thereof into a buffer for conjugation.

6. The method claim 3, wherein the pre-processing of the antibody or antigen-binding fragment thereof comprises reducing the antibody or antigen-binding fragment thereof and/or oxidizing the antibody or antigen-binding fragment thereof.

7. A method for producing an antibody drug conjugate (ADC) composition in a continuous conjugation process, comprising (i) continuously adding one or more conjugation reaction reagents to an ADC conjugation reaction while the conjugation reaction proceeds and after at least one ADC has formed, wherein the conjugation reaction occurs in a flow reactor and (ii) continuously removing unconjugated drug using countercurrent diafiltration, wherein the ADC composition has an average drug-to-antibody ratio from 2 to 8; and wherein the ADC comprises an IgA, IgD, IgE, IgG, or IgM antibody or antigen-binding fragment thereof.

8. The method of claim 7 wherein the conjugation reaction reagent comprises an antibody or antigen-binding fragment thereof, a linker, or an antibody or antigen-binding fragment thereof attached to a linker.

9. The method of claim 7, further comprising pre-processing an antibody or antigen-binding fragment thereof.

10. The method of claim 3, wherein the pre-processing of the antibody or antigen-binding fragment thereof is performed continuously with (i) to (iii) and wherein the ADC is concentrated using single-pass tangential flow filtration and/or countercurrent diafiltration, the ADC is purified using single-pass tangential flow filtration and/or countercurrent diafiltration, and/or the ADC is transferred to a formulation buffer using single-pass tangential flow filtration and/or countercurrent diafiltration.

11. The method of claim 1, wherein the method improves the consistency of the ADC production, decreases the time for ADC production, improves the consistency of the ADC production, decreases the time for ADC concentration, purification, or transfer and/or decreases the amount of buffer used.

12. The method of claim 1, wherein the method further comprises in-line monitoring of an analyte.

13. The method of claim 1, wherein the ADC is IMGN853 and the method comprises (i) mixing an antibody comprising a variable heavy chain comprising the amino acid sequence of SEQ ID NO:37 and a variable light chain comprising the amino acid sequence of SEQ ID NO:39 and N(2')-deacetyl-N(2')-(4-mercapto-4-methyl-1-oxopentyl) maytansine (DM4)-linked to N-succinimidyl 4-(2-pyridyldithio)-2-sulfobutanoate (sulfo-SPDB) in a continuous conjugation process to form IMGN853 (ii) concentrating IMGN853 using single-pass tangential flow filtration and/or countercurrent diafiltration, (iii) removing unconjugated drug from IMGN853 using single-pass tangential flow filtration and/or countercurrent diafiltration, and (iv) exchanging the IMGN853 into a formulation buffer using single-pass tangential flow filtration and/or countercurrent diafiltration.

14. The method of claim 1, wherein the ADC is IMGN779 and the method comprises (i) mixing an antibody comprising a variable heavy chain comprising the amino acid sequence of SEQ ID NO:40 and a variable light chain comprising the amino acid sequence of SEQ ID NO:41 and DGN462-linked to sulfo-SPDB in a continuous conjugation process to form IMGN779, (ii) concentrating IMGN779 using single-pass tangential flow filtration and/or countercurrent diafiltration, (iii) removing unconjugated drug from IMGN779 using single-pass tangential flow filtration and/or countercurrent diafiltration, and (iv) exchanging the IMGN779 into a formulation buffer using single-pass tangential flow filtration and/or countercurrent diafiltration.

15. The method of claim 1, wherein the ADC is IMGN632 and the method comprises (i) mixing an antibody comprising a variable heavy chain comprising the amino acid sequence of SEQ ID NO:42 and a variable light chain comprising the amino acid sequence of SEQ ID NO:43 and sulfonated DGN549C in a continuous conjugation process to form IMGN632, (ii) concentrating IMGN632 using single-pass tangential flow filtration and/or countercurrent diafiltration, (iii) removing unconjugated drug from IMGN632 using single-pass tangential flow filtration and/or countercurrent diafiltration, and (iv) exchanging the IMGN632 into a formulation buffer using single-pass tangential flow filtration and/or countercurrent diafiltration.

16. The method of claim 1, wherein the method comprises increasing a first temperature of a conjugation process by at least 5° C. to an elevated temperature, wherein the elevated temperature is maintained for no more than 20 minutes.

17. The method of claim 1, wherein the ADC comprises an antibody or antigen-binding fragment thereof that binds to FOLR1.

18. The method of claim 1, wherein the ADC comprises an antibody or antigen-binding fragment thereof that binds to CD33.

19. The method of claim 1, wherein the ADC comprises an antibody or antigen-binding fragment thereof that binds to CD123.

20. The method of claim 1, wherein the ADC comprises an antibody or antigen-binding fragment thereof that binds to FOLR1, CD33, CD123, CD37, CD19, cMET, ADAM9, or HER2.

21. The method of claim 7, wherein the ADC comprises an antibody or antigen-binding fragment thereof that binds to FOLR1.

22. The method of claim 7, wherein the ADC comprises an antibody or antigen-binding fragment thereof that binds to CD33.

23. The method of claim 7, wherein the ADC comprises an antibody or antigen-binding fragment thereof that binds to CD123.

24. The method of claim 7, wherein the ADC comprises an antibody or antigen-binding fragment thereof that binds to FOLR1, CD33, CD123, CD37, CD19, cMET, ADAM9, or HER2.

25. The method of claim 1, wherein the drug is a maytansinoid, a maytansinoid analog, a benzodiazepine, a pyrrolobenzodiazepine, a taxoid, CC-1065, a CC-1065 analog, a duocarmycin, a duocarmycin analog, a enediyne, a dolastatin, a dolastatin analog, a tomaymycin derivative, a leptomycin derivative, methotrexate, cisplatin, carboplatin, daunorubicin, doxorubicin, vincristine, vinblastine, melphalan, mitomycin C, chlorambucil, or a morpholino doxorubicin.

26. The method of claim 1, wherein the ADC comprises a linker that is a disulfide linker, a thioether linker, an acid labile linker, a photolabile linker, a peptidase labile linker, or a esterase labile linker.

27. The method of claim 25, wherein the ADC comprises a linker that is a disulfide linker, a thioether linker, an acid labile linker, a photolabile linker, a peptidase labile linker, or a esterase labile linker.

28. The method of claim 25, wherein the ADC binds to FOLR1, CD33, CD123,_CD37, CD19, cMET, ADAM9, or HER2.

29. The method of claim 27, wherein the ADC binds to FOLR1, CD33, CD123, CD37, CD19, cMET, ADAM9, or HER2.

30. The method of claim 6, wherein the reducing and/or the oxidizing are achieved without using SPTFF or countercurrent diafiltration.

31. The method of claim 6, wherein the reducing and/or the oxidizing are achieved using only one SPTFF or countercurrent diafiltration step.

32. The method of claim 13, wherein in-line monitoring is used to measure the concentration of the antibody added to the conjugation reaction, to measure the concentration of unconjugated drug in the retentate, to measure the concentration of unconjugated drug in the retentate, and/or to measure the concentration of impurities in the retentate.

33. The method of claim 7, wherein the drug is a maytansinoid, a maytansinoid analog, a benzodiazepine, a pyrrolobenzodiazepine, a taxoid, CC-1065, a CC-1065 analog, a duocarmycin, a duocarmycin analog, a enediyne, a dolastatin, a dolastatin analog, a tomaymycin derivative, a leptomycin derivative, methotrexate, cisplatin, carboplatin, daunorubicin, doxorubicin, vincristine, vinblastine, melphalan, mitomycin C, chlorambucil, or a morpholino doxorubicin.

34. The method of claim 7, wherein the ADC comprises a linker that is a disulfide linker, a thioether linker, an acid labile linker, a photolabile linker, a peptidase labile linker, or a esterase labile linker.

35. The method of claim 33, wherein the ADC comprises a linker that is a disulfide linker, a thioether linker, an acid labile linker, a photolabile linker, a peptidase labile linker, or a esterase labile linker.

36. The method of claim 33, wherein the ADC comprises an antibody or antigen-binding fragment thereof that binds to FOLR1, CD33, CD123, CD37, CD19, cMET, ADAM9, or HER2.

37. The method of claim 35, wherein the ADC comprises an antibody or antigen-binding fragment thereof that binds to FOLR1, CD33, CD123, CD37, CD19, cMET, ADAM9, or HER2.

38. The method of claim 7, wherein the conjugation reaction reagent is a drug attached to a linker or a drug.

39. A method for producing an antibody drug conjugate (ADC) composition in a continuous conjugation process, comprising (i) continuously adding one or more conjugation reaction reagents to an ADC conjugation reaction while the conjugation reaction proceeds and after at least one ADC has formed, wherein the conjugation reaction occurs in a flow reactor and (ii) continuously removing unconjugated drug using single-pass tangential flow filtration (SPTFF), wherein the ADC composition has an average drug-to-antibody ratio from 2 to 8; and wherein the ADC comprises an IgA, IgD, IgE, IgG, or IgM antibody or antigen-binding fragment thereof.

* * * * *